(12) United States Patent
Nelson et al.

(10) Patent No.: US 10,668,268 B2
(45) Date of Patent: Jun. 2, 2020

(54) MEDICAL CONNECTOR

(71) Applicant: ICU MEDICAL, INC., San Clemente, CA (US)

(72) Inventors: David Nelson, Irvine, CA (US); Thomas F. Fangrow, Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 308 days.

(21) Appl. No.: 15/721,297

(22) Filed: Sep. 29, 2017

(65) Prior Publication Data

US 2018/0021561 A1 Jan. 25, 2018

Related U.S. Application Data

(62) Division of application No. 14/195,602, filed on Mar. 3, 2014, now Pat. No. 9,775,981.

(60) Provisional application No. 61/914,680, filed on Dec. 11, 2013, provisional application No. 61/884,913, filed on Sep. 30, 2013, provisional application No. 61/793,511, filed on Mar. 15, 2013.

(51) Int. Cl.
*A61M 39/22* (2006.01)
*A61B 5/15* (2006.01)

(52) U.S. Cl.
CPC ..... *A61M 39/225* (2013.01); *A61B 5/150992* (2013.01); *A61M 39/223* (2013.01); *A61B 5/15003* (2013.01); *A61B 5/150221* (2013.01)

(58) Field of Classification Search
CPC .............. A61M 39/225; A61M 39/223; A61B 5/150992

USPC .......................................................... 600/573
See application file for complete search history.

(56) References Cited

U.S. PATENT DOCUMENTS

| | | |
|---|---|---|
| 3,780,736 A | 12/1973 | Chen |
| 3,952,729 A | 4/1976 | Libman et al. |
| 4,219,021 A | 8/1980 | Fink |
| 4,353,243 A | 10/1982 | Martin |
| 4,566,480 A | 6/1986 | Parham |
| 4,950,230 A | 8/1990 | Kendall |
| 4,981,140 A | 1/1991 | Wyatt |
| 5,417,673 A | 5/1995 | Gordon |
| 5,462,255 A | 10/1995 | Rosen et al. |
| 5,578,016 A | 11/1996 | Zinger |

(Continued)

FOREIGN PATENT DOCUMENTS

| | | |
|---|---|---|
| CN | 101045176 A | 10/2007 |
| JP | 2004-105574 | 4/2004 |

(Continued)

OTHER PUBLICATIONS

European Extended Search Report, re EP Application No. 14767772, dated Nov. 22, 2016.

(Continued)

*Primary Examiner* — Daniel L Cerioni
(74) *Attorney, Agent, or Firm* — Knobbe, Martens, Olson & Bear, LLP

(57) ABSTRACT

A medical connector for use in a fluid pathway. A valve member with sealing rings helps preclude undesired accumulation of fluid within the connector. A branched connector includes a fluid diverter extending away from a port of the branched connector. The fluid diverter is configured to divert fluid flowing through the branched connector and into a medical connector attached thereto, flushing a distal portion of the medical connector.

11 Claims, 60 Drawing Sheets

(56) References Cited

U.S. PATENT DOCUMENTS

| | | |
|---|---|---|
| 5,694,686 A | 12/1997 | Lopez |
| 5,695,466 A | 12/1997 | Lopez et al. |
| 5,730,418 A | 3/1998 | Feith et al. |
| 5,772,608 A | 6/1998 | Dhas |
| 5,782,816 A | 7/1998 | Werschmidt et al. |
| 5,788,215 A | 8/1998 | Ryan |
| 5,954,313 A | 9/1999 | Ryan |
| 6,029,946 A | 2/2000 | Doyle |
| 6,106,502 A | 8/2000 | Richmond |
| 6,106,512 A | 8/2000 | Cochran et al. |
| 6,158,467 A | 12/2000 | Loo |
| 6,168,137 B1 | 1/2001 | Paradis |
| 6,299,131 B1 | 10/2001 | Ryan |
| 6,364,861 B1 | 4/2002 | Feith et al. |
| 6,457,488 B2 | 10/2002 | Loo |
| 6,997,917 B2 | 2/2006 | Niedospial, Jr. et al. |
| 7,033,339 B1 | 4/2006 | Lynn |
| 7,160,272 B1 | 1/2007 | Eyal et al. |
| 7,232,428 B1 | 6/2007 | Inukai et al. |
| 7,520,489 B2 | 4/2009 | Ruschke et al. |
| 7,600,530 B2 | 10/2009 | Truitt et al. |
| 7,645,274 B2 | 1/2010 | Whitley |
| 7,651,481 B2 | 1/2010 | Raybuck |
| 7,722,576 B2 | 5/2010 | Lopez |
| 7,766,304 B2 | 8/2010 | Phillips |
| 7,771,383 B2 | 8/2010 | Truitt et al. |
| 7,909,056 B2 | 3/2011 | Truitt et al. |
| 7,984,730 B2 | 7/2011 | Ziv et al. |
| 7,993,328 B2 | 8/2011 | Whitley |
| 8,096,525 B2 | 1/2012 | Ryan |
| 8,162,914 B2 | 4/2012 | Kraushaar et al. |
| 8,177,760 B2 | 5/2012 | Rome et al. |
| 8,197,452 B2 | 6/2012 | Harding et al. |
| 8,197,466 B2 | 6/2012 | Yokota et al. |
| 8,241,268 B2 | 8/2012 | Whitley |
| 8,277,424 B2 | 10/2012 | Pan |
| 8,287,518 B2 | 10/2012 | Kitani et al. |
| 8,298,195 B2 | 10/2012 | Peppel |
| 8,337,483 B2 | 12/2012 | Harding et al. |
| 8,361,408 B2 | 1/2013 | Lynn |
| 8,366,676 B2 | 2/2013 | Harding et al. |
| 8,377,010 B2 | 2/2013 | Harding et al. |
| 8,403,894 B2 | 3/2013 | Lynn et al. |
| 8,403,905 B2 | 3/2013 | Yow |
| 8,408,226 B2 | 4/2013 | Raines et al. |
| 8,409,165 B2 | 4/2013 | Niedospial, Jr. et al. |
| 8,454,579 B2 | 6/2013 | Fangrow, Jr. |
| 8,522,832 B2 | 9/2013 | Lopez et al. |
| 8,529,524 B2 | 9/2013 | Newton et al. |
| 8,636,720 B2 | 1/2014 | Truitt et al. |
| 8,640,725 B2 | 2/2014 | Truitt et al. |
| 8,671,964 B2 | 3/2014 | Py |
| 8,684,994 B2 | 4/2014 | Lev et al. |
| 8,702,675 B2 | 4/2014 | Imai |
| 8,715,222 B2 | 5/2014 | Truitt et al. |
| 8,715,247 B2 | 5/2014 | Mansour et al. |
| 8,721,627 B2 | 5/2014 | Alpert |
| 8,801,678 B2 | 8/2014 | Panian et al. |
| 8,834,432 B2 | 9/2014 | Winsor et al. |
| 8,840,577 B1 | 9/2014 | Zollinger et al. |
| 8,870,846 B2 | 10/2014 | Davis et al. |
| 8,876,784 B2 | 11/2014 | Coete, Sr. et al. |
| 8,882,742 B2 | 11/2014 | Dikeman et al. |
| 8,910,919 B2 | 12/2014 | Bonnal et al. |
| 8,951,233 B2 | 2/2015 | Mansour |
| 8,968,261 B2 | 3/2015 | Kimball et al. |
| 8,968,271 B2 | 3/2015 | Guala |
| 8,974,425 B2 | 3/2015 | Tachizaki et al. |
| 8,979,804 B2 | 3/2015 | Ho et al. |
| 8,986,272 B2 | 3/2015 | Young et al. |
| 9,017,295 B2 | 4/2015 | Pan |
| 9,032,997 B2 | 5/2015 | Abura et al. |
| 9,039,047 B2 | 5/2015 | Imai |
| 9,044,585 B2 | 6/2015 | Masuda et al. |
| 9,061,130 B2 | 6/2015 | Truitt et al. |
| 9,067,049 B2 | 6/2015 | Panian et al. |
| 9,089,680 B2 | 7/2015 | Ueda et al. |
| 9,089,681 B2 | 7/2015 | Ueda et al. |
| 9,114,244 B2 | 8/2015 | Yeh et al. |
| 9,119,950 B2 | 9/2015 | Mansour et al. |
| 9,138,572 B2 | 9/2015 | Zeytoonian et al. |
| 9,144,672 B2 | 9/2015 | Mansour et al. |
| 9,162,029 B2 | 10/2015 | Zollinger |
| 9,198,831 B2 | 12/2015 | Rogers |
| 9,212,762 B2 | 12/2015 | Duncan |
| 9,212,772 B2 | 12/2015 | Ho et al. |
| 9,220,882 B2 | 12/2015 | Belley et al. |
| 9,234,616 B2 | 1/2016 | Carrez et al. |
| 9,238,128 B2 | 1/2016 | Yamaguchi et al. |
| 9,289,588 B2 | 3/2016 | Chen |
| 9,314,604 B2 | 4/2016 | Bonnal et al. |
| 9,345,641 B2 | 5/2016 | Kraus et al. |
| 9,370,651 B2 | 6/2016 | Zollinger et al. |
| 9,375,561 B2 | 6/2016 | Mansour et al. |
| 9,409,007 B2 | 8/2016 | Yeh |
| 9,433,708 B2 | 9/2016 | Eddy |
| 2001/0049508 A1 | 12/2001 | Fangrow, Jr. et al. |
| 2002/0000253 A1 | 1/2002 | Fillmore et al. |
| 2002/0156431 A1 | 10/2002 | Feith et al. |
| 2004/0243069 A1 | 12/2004 | Feith et al. |
| 2005/0261637 A1 | 11/2005 | Miller |
| 2006/0089603 A1 | 4/2006 | Truitt et al. |
| 2008/0067462 A1 | 3/2008 | Miller et al. |
| 2009/0182309 A1 | 7/2009 | Muffly |
| 2009/0299300 A1 | 12/2009 | Truitt et al. |
| 2010/0059702 A1 | 3/2010 | Mansour et al. |
| 2010/0063482 A1 | 3/2010 | Mansour et al. |
| 2010/0241088 A1 | 9/2010 | Ranalletta et al. |
| 2010/0249723 A1 | 9/2010 | Fangrow, Jr. |
| 2010/0256573 A1 | 10/2010 | Mansour et al. |
| 2010/0292673 A1 | 11/2010 | Korogi et al. |
| 2011/0028914 A1 | 2/2011 | Mansour et al. |
| 2011/0152787 A1 | 6/2011 | Truitt et al. |
| 2011/0257606 A1 | 10/2011 | Truitt et al. |
| 2011/0282302 A1 | 11/2011 | Lopez et al. |
| 2011/0308651 A1 | 12/2011 | Ziv et al. |
| 2011/0319859 A1 | 12/2011 | Zeytoonian et al. |
| 2012/0109077 A1 | 5/2012 | Ryan |
| 2012/0130305 A1 | 5/2012 | Bonnal et al. |
| 2012/0153201 A1 | 6/2012 | Larose et al. |
| 2012/0220955 A1 | 8/2012 | Maseda et al. |
| 2012/0220984 A1 | 8/2012 | Christensen et al. |
| 2012/0316536 A1 | 12/2012 | Carrez et al. |
| 2013/0053815 A1 | 2/2013 | Mucientes et al. |
| 2013/0060205 A1 | 3/2013 | Mansour et al. |
| 2013/0066293 A1 | 3/2013 | Garfield et al. |
| 2013/0079730 A1 | 3/2013 | Mosler et al. |
| 2014/0018746 A1 | 1/2014 | Ueda et al. |
| 2014/0031765 A1 | 1/2014 | Siopes et al. |
| 2014/0155837 A1 | 6/2014 | Masuda et al. |
| 2014/0174578 A1 | 6/2014 | Bonnal et al. |
| 2014/0180219 A1 | 6/2014 | Ho et al. |
| 2014/0180258 A1 | 6/2014 | Ho et al. |
| 2014/0207117 A1 | 7/2014 | Ueda et al. |
| 2014/0261860 A1 | 9/2014 | Heath et al. |
| 2014/0276215 A1 | 9/2014 | Nelson |
| 2014/0276455 A1 | 9/2014 | Yeh et al. |
| 2014/0276456 A1 | 9/2014 | Eddy |
| 2014/0276458 A1 | 9/2014 | Mansour et al. |
| 2014/0276459 A1 | 9/2014 | Yeh et al. |
| 2014/0276460 A1 | 9/2014 | Zollinger et al. |
| 2014/0276463 A1 | 9/2014 | Mansour et al. |
| 2014/0276466 A1 | 9/2014 | Yeh et al. |
| 2014/0296794 A1 | 10/2014 | Li |
| 2014/0316350 A1 | 10/2014 | Yamaguchi et al. |
| 2014/0332091 A1 | 11/2014 | Ueda et al. |
| 2014/0358033 A1 | 12/2014 | Lynn |
| 2014/0371686 A1 | 12/2014 | Sano et al. |
| 2015/0008664 A1 | 1/2015 | Tachizaki |
| 2015/0013807 A1 | 1/2015 | Ueda |
| 2015/0045746 A1 | 2/2015 | Macy, Jr. et al. |
| 2015/0126942 A1 | 5/2015 | Lopez et al. |
| 2015/0148756 A1 | 5/2015 | Lynn |
| 2015/0157799 A1 | 6/2015 | Chen et al. |

(56) References Cited

U.S. PATENT DOCUMENTS

| | | |
|---|---|---|
| 2015/0157800 A1 | 6/2015 | Chen et al. |
| 2015/0157848 A1 | 6/2015 | Wu et al. |
| 2015/0190627 A1 | 7/2015 | Ueda et al. |
| 2015/0196749 A1 | 7/2015 | Ziv et al. |
| 2015/0196750 A1 | 7/2015 | Ueda et al. |
| 2015/0202424 A1 | 7/2015 | Harton |
| 2015/0258325 A1 | 9/2015 | Panian et al. |
| 2015/0265829 A1 | 9/2015 | Truitt et al. |
| 2015/0283373 A1 | 10/2015 | Yeh et al. |
| 2015/0297817 A1 | 10/2015 | Guala |
| 2015/0297880 A1 | 10/2015 | Ogawa et al. |
| 2015/0313523 A1 | 11/2015 | Chelak et al. |
| 2016/0001057 A1 | 1/2016 | Lopez et al. |
| 2016/0004364 A1 | 1/2016 | Mendels et al. |
| 2016/0015958 A1 | 1/2016 | Ueda et al. |
| 2016/0015961 A1 | 1/2016 | Mansour et al. |
| 2016/0022977 A1 | 1/2016 | Ueda et al. |
| 2016/0022978 A1 | 1/2016 | Ueda |
| 2016/0030730 A1 | 2/2016 | Mosler et al. |
| 2016/0038730 A1 | 2/2016 | Zollinger |
| 2016/0136051 A1 | 5/2016 | Lavi |
| 2016/0144110 A1 | 5/2016 | Ueda |
| 2016/0158524 A1 | 6/2016 | Quach et al. |
| 2016/0235961 A1 | 8/2016 | Maffei |

FOREIGN PATENT DOCUMENTS

| | | |
|---|---|---|
| WO | WO 99/61093 | 12/1999 |
| WO | WO 2006/025054 | 3/2006 |
| WO | WO 2013/036854 | 3/2013 |

OTHER PUBLICATIONS

MicroClave Connector Brochure. The MicroClave was available before Mar. 25, 2008.

International Search Report and Written Opinion, re PCT Application No. PCT/US2014/019628, dated Aug. 8, 2014.

International Preliminary Report on Patentability, re PCT Application No. PCT/US2014/019628, dated Sep. 24, 2015.

MEDICAL CONNECTOR

CROSS-REFERENCE TO RELATED APPLICATIONS

Any and all applications for which a foreign or domestic priority claim is identified in the Application Data Sheet as filed with the present application, are hereby incorporated by reference under 37 CFR 1.57. This application is a divisional of U.S. patent application Ser. No. 14/195,602, filed Mar. 3, 2014, and entitled "MEDICAL CONNECTOR," which claims the benefit of U.S. Provisional Patent Application No. 61/793,511, filed Mar. 15, 2013, and entitled "MEDICAL CONNECTOR"; U.S. Provisional Patent Application No. 61/884,913, filed Sep. 30, 2013, and entitled "MEDICAL CONNECTOR"; and U.S. Provisional Patent Application No. 61/914,680, filed Dec. 11, 2013, and entitled "MEDICAL CONNECTOR," the entire disclosure of each being hereby incorporated by reference herein and made a part of this disclosure.

BACKGROUND OF THE INVENTION

Field of the Disclosure

The present disclosure relates in general to the field of medical connectors, and in particular to selectively sealed medical connectors.

Description of the Related Art

A variety of devices and techniques exist for the manipulation of fluids in hospitals and medical settings, and in particular the selective facilitation of fluid movement to or from patients. Fluid flow lines rely on a variety of connectors to help develop preferred flow characteristics or access points.

Current fluid flow systems and medical connectors have various limitations and disadvantages and a need exists for further improvement.

SUMMARY OF THE DISCLOSURE

A variety of fluid flow lines and systems are used in hospitals and medical settings for the selective facilitation of fluid movement to or from patients. For example, central venous catheters can be used to administer IV fluids, various medications or blood products, and/or parenteral nutrition. Because such flow lines provide access to a patient's blood stream, they inherently generate risks of blood stream infections, as pathogens can make their way into the fluid flow lines at different access points. Generally, risks of infection or other complications can be minimized by limiting the number of times that flow lines need to be established, which limits the opportunities for pathogens to enter the system. Risks of infection can also be minimized by eliminating residual blood in a fluid flow line.

Various embodiments described herein provide techniques and devices that can be used to minimize the risk of infection or other complications. For example, in some fluid flow lines branched connectors, such as three or four-port stopcocks, y-sites, and other ports can be used to provide access to the flow line. Access can be used, for example, to withdraw samples or introduce medicine or other products. Blood can accumulate in ports when they are not in use, and the ports can clot and cause problems in the line, requiring it to be reestablished. Various embodiments described herein allow for flushing of stopcock ports, helping prevent accumulated fluid. In some embodiments, flushing can be achieved with a fluid diverter, which can divert fluid flow into a port of the stopcock beyond a base of the port. In some embodiments, fluid can be directed to a distal portion of the port.

Various embodiments described herein relate to needleless connectors and valves that can also help prevent risks of infection or the need to reestablish fluid flow lines. For example, some needleless connectors described herein can have minimal internal or priming volumes, making them easier and more efficient to flush. Some embodiments of needleless connectors described herein can have elements designed to prevent accumulation of blood during and after the connector is used to access the fluid flow line.

Additionally, when working with a fluid flow line to selectively facilitate flow of fluid to or from a patient, it can be desirable to monitor hemodynamic status. Various embodiments described herein can allow for effective monitoring of hemodynamic status.

In various embodiments, a three-way stopcock adapted for flushing a needleless connector on one port of the stopcock can include a stopcock body having a first port, a second port, a third port, and a connecting region connecting the first port, the second port, and the third port. The third port can be positioned between first and second ports.

The stopcock can also include a fluid director positioned at least partially within the connecting region. The fluid director can be configured to selectively place one or more of the first port, the second port, and the third port in fluid communication with another of the first port, the second port, and/or the third port. The stopcock can also include a fluid diverter extending away from the connecting region at the third port and having a proximal end and a distal end positioned further from the third port than the proximal end. The stopcock can also include a needleless connector attached to the third port and at least partially surrounding the fluid diverter.

The needleless connector can have a connector housing and a compressible seal positioned at least partially within the connector housing and having an interior cavity and a slit on a top of the seal that extends through the top and into the interior cavity. In some embodiments, the needleless connector can also have an internal projection member positioned at least partially within the compressible seal, the internal projection member having walls that define an internal cavity that encompasses the fluid diverter, an opening at a proximal end of the internal projection member, an interior height from the opening to a most distal surface of the walls that define the internal cavity, and at least one distal opening at or near a distal end of the internal projection member, the at least one distal opening having a proximal surface. In some embodiments, the at least one distal opening can also have a distal surface. In some embodiments, the fluid diverter and the internal projection member can be integrally formed.

In some embodiments, the fluid diverter is adjacent the walls of the internal cavity of the internal projection member to substantially bifurcate the internal cavity of the internal projection member at the proximal end of the internal projection member. In some embodiments, the fluid diverter bifurcates the internal cavity of the internal projection member at the proximal end of the internal projection member.

In some embodiments, the fluid diverter substantially bifurcates at least about half of the internal cavity of the internal projection member. In some embodiments, the fluid diverter substantially bifurcates at least about three quarters of the internal cavity of the internal projection member. In some embodiments, the fluid diverter can have a distal tip that extends within the internal projection member to at least the proximal surface of the at least one distal opening.

In some embodiments, the compressible seal can have a plurality of sealing rings on an interior surface thereof, and the plurality of sealing rings can be configured to contact and seal against the internal projection member. In some embodiments, at least one sealing ring of the plurality of sealing rings can contact the internal projection member above the at least one distal opening, and at least one sealing ring of the plurality of sealing rings can contact the internal projection member below the at least one distal opening.

In some embodiments, a height of the internal projection member from the distal surface of the at least one distal opening to an upper tip of the internal projection member can be greater than or equal to a height in the cavity of the compressible seal from an uppermost sealing ring to an uppermost surface of the cavity.

In various embodiments, a multi-port branched medical connector adapted for flushing a needleless connector on one port of the branched connector can include a body having a first port, a second port, a third port, and a connecting region connecting the first port, the second port, and the third port, wherein the third port is positioned between the first and second ports. The connector can include a fluid diverter extending away from the connecting region at the third port and having a proximal end and a distal end positioned further from the third port than the proximal end.

The branched medical connector can also include a needleless connector attached to the third port and at least partially surrounding the fluid diverter. The needleless connector can have a connector housing, a compressible seal positioned at least partially within the connector housing and having an interior cavity and a slit on a top of the seal that extends through the top and into the interior cavity. In some embodiments, the connector can also include an internal projection member positioned at least partially within the compressible seal, the internal projection member having walls that define an internal cavity that encompasses the fluid diverter, an opening at a proximal end of the internal projection member, and at least one distal opening at a distal end of the internal projection member. In some embodiments, the at least one distal opening includes a proximal surface and a distal surface. In some embodiments the fluid diverter extends from the proximal end of the internal projection member to at least the proximal surface of the at least one distal opening.

In some embodiments, the fluid diverter can extend from the proximal end of the internal projection member to a position past the proximal surface of the at least one distal opening. In some embodiments, the fluid diverter can substantially bifurcate at least half of the internal projection member. In some embodiments, the fluid diverter can substantially bifurcate at least three quarters of the internal projection member. In some embodiments, the fluid diverter and the internal projection member can be integrally molded.

In some embodiments, the compressible seal can have a plurality of sealing rings on an interior surface thereof, the plurality of sealing rings configured to contact and seal against the internal projection member. In some embodiments, at least one sealing ring of the plurality of sealing rings contacts the internal projection member above the at least one distal opening and at least one sealing ring of the plurality of sealing rings contacts the internal projection member below the at least one distal opening. In some embodiments, a height of the internal projection member from the distal surface of the at least one distal opening to an upper tip of the internal projection member is greater than or equal to a height in the cavity of the compressible seal from an uppermost sealing ring to an uppermost surface of the interior cavity.

In some embodiments, a system for accessing a fluid flow path with a medical connector that can be flushed with fluid includes a stopcock housing having a first port, a second port, a third port, and a connecting region connecting the first port, the second port, and the third port. A fluid diverter can extend away from the connecting region at the third port and have a proximal end and a distal end positioned further from the third port than the proximal end. The fluid diverter can also have a proximal tip at its proximal end and a distal tip at its distal end.

The system can also include a first line connected to the first port and configured to fluidly communicate with a patient, a second line connected to the second port and configured to fluidly communicate with a fluid source, and a medical connector attached to the third port and at least partially surrounding the fluid diverter, the medical connector having a height from the proximal tip of the fluid diverter to a top surface of the medical connector. In some embodiments, the fluid diverter can be integrally molded with a portion of the medical connector.

In some embodiments, the distal tip of the fluid diverter extends into the distal two thirds of the height of the medical connector. In some embodiments, the distal tip of the fluid diverter extends into the distal one half of the height of the medical connector. In some embodiments, the distal tip of the fluid diverter extends into the distal one quarter of the height of the medical connector. In some embodiments, the system can also include a syringe positioned in-line between the second port and a fluid source.

In some embodiments, a method for withdrawing a blood sample from a fluid line delivering fluid from a fluid source to a patient can include: blocking a flow of fluid between a fluid source and a stopcock positioned in the fluid line between a patient and the fluid source, the stopcock including a first port connected to the patient, a second port connected to the fluid source, and a third port that has a needleless connector encompassing a fluid diverter that substantially bifurcates at least about half of the needleless connector, wherein the stopcock is in a first position in which the first, second, and third ports are in fluid communication with each other; priming the stopcock with blood; moving the stopcock to a second position wherein the second port is fluidly block from the first and third ports; withdrawing blood through the needleless connector; moving the stopcock to the first position; and opening the flow of fluid between the fluid source and the stopcock, wherein opening the flow of fluid flushes the blood in the stopcock with fluid from the fluid source.

In some embodiments, an access connector for a fluid line can include a housing, an internal projection member, and a seal. The connector can selectively prevent fluid flow therethrough. In some embodiments, the seal can be compressed to facilitate fluid flow to the distal end of the housing.

In some embodiments, a multi-port branched medical connector adapted for flushing a needleless connector on one port of the branched connector can include a body comprising a first port, a second port, a third port, wherein the third port is positioned between the first and second ports, a fluid diverter extending into the third port, and a needleless connector attached to the third port and at least partially surrounding the fluid diverter. The needleless connector can include a connector housing having a proximal end and a distal end. The connector can also include a resilient member positioned at least partially within the connector housing and configured to impede flow through the distal end when in a first position. In some embodiments, the fluid diverter can extend into the resilient member a substantial distance. In some embodiments, the needleless connector when at least partially surrounding the fluid diverter has a flushable volume that is less than approximately 0.02 milliliters. In some embodiments, the flushable volume is between approximately 0.01 milliliters and approximately 0.02 milliliters. In some embodiments, the flushable volume is approximately 0.015 milliliters.

In some embodiments, a multi-port branched medical connector adapted for flushing a needleless connector on one port of the branched connector can include a body comprising a first port, a second port, a third port, and a connecting region connecting the first port, the second port, and the third port, wherein the third port is positioned between the first and second ports. In some embodiments, a fluid director can be positioned at least partially within the connecting region and configured to selectively place one or more of the first port, the second port, and the third port in fluid communication with another of the first port, the second port, and the third port. The fluid director can include a fluid flow guide with an opening. In some embodiments a fluid diverter can extend away from the connecting region at the third port and can have a proximal end and a distal end positioned further from the third port than the proximal end. A medical connector attached to the third port can at least partially surrounding the fluid diverter. In some embodiments, when the first port, the second port, and the third port are in fluid communication with each other and a fluid flows from the first port to the second port, the fluid flow guide can be configured to direct a first portion of the fluid flow into the third port and allow a second portion of the fluid flow to pass through the opening to the second port. In some embodiments, the opening can be a notch.

In various embodiments, a needleless medical connector can include a connector housing and an internal projection member positioned at least partially within the connector housing, the internal projection member having walls that define an internal cavity, at least one proximal opening at a proximal end of the internal projection member, and at least one distal opening at a distal end of the internal projection member, the at least one distal opening having a proximal surface and a distal surface and a height therebetween. The needleless medical connector can also include a compressible seal positioned at least partially within the connector housing, the compressible seal including a body wall that defines an interior cavity and that has an inner surface surrounding at least part of the internal projection member, an upper section positioned above the distal surface of the at least one distal opening of the internal projection member, and a slit on a top of the seal that extends through the top of the seal and into the interior cavity.

In some embodiments, the upper section of the compressible seal can have an interference fit with the internal projection member. In some embodiments, a width of a segment of the internal projection member at its distal end is greater than a width of a corresponding segment of the interior cavity of the compressible seal.

In some embodiments, a portion of the inner surface of the body wall of the compressible seal at the upper section of the compressible seal can have surface roughenings. In some embodiments, the portion of the inner surface with surface roughenings is scalloped.

In some embodiments, a thickness of the body wall adjacent the base is less than any other thickness of the body wall below the at least one sealing ring. In some embodiments, the thickness of the body wall adjacent the base is less than any other thickness of the body wall above the at least one sealing ring. In some embodiments, the compressible seal further comprises a shoulder, and the thickness of the body wall adjacent the base is less than any other thickness of the body wall below the shoulder. In some embodiments, the base of the cylinder can be generally cylindrical and has a diametrical width and a thickness. In some embodiments, the ratio of the width to the thickness can be between approximately 3 and approximately 4.5. In some embodiments, the ratio of the width to the thickness can be between approximately 3.5 and approximately 4

In some embodiments, the connector housing has a distal end configured to mate with a medical device. In some embodiments, the upper section of the compressible seal is configured to substantially eliminate the accumulation of fluid between the upper section and the internal projection member above the distal surface of the at least one distal opening when the connector is in a first, closed configuration.

In some embodiments, the internal projection member includes a projection tip between the distal surface of the at least one distal opening and a distal most end of the internal projection member. The projection tip can have a height. In some embodiments, the height of the projection tip is approximately equal to the height of the at least one distal opening. In some embodiments, the height of the projection tip is approximately equal to three quarters of the height of the at least one distal opening. In some embodiments, the height of the projection tip is approximately equal to one quarter of the height of the at least one distal opening. In some embodiments, the needleless connector includes a gap between a bottom interior surface of a top of the valve member and the projection tip.

In some embodiments, the needless connector can be attached to a first port of a branched connector. In some embodiments, the branched connector can be a stopcock. In some embodiments, the branched connector can include a connecting region that connects the ports of the branched connector, and a fluid diverter extending away from the connecting region at the first port. The needleless connector can at least partially surround the fluid diverter. In some embodiments, the fluid diverter can be adjacent the walls of the internal cavity of the internal projection member to substantially bifurcate the internal cavity of the internal projection member at the proximal end of the internal projection member.

In various embodiments, a method of manufacturing a valve member of a medical connector with an injection molding process can include injection molding a valve member around a core pin and at least partially within a sleeve. The core pin can include a proximal section and a distal section, and the distal section can include at least one indent configured to define scalloped sections on the valve member. The indent can have a width and a depth, and the ratio of the width to the depth can be between approximately 10 and approximately 30. In some embodiments, the ratio can be between approximately 15 and approximately 25. The core pin can then be withdrawn from the valve member, and the valve member can be separated from the sleeve.

In some embodiments, the at least one indent can be a plurality of indents. In some embodiments, at least two of the plurality of indents can have different widths and depths. In some embodiments, the at least one indent can extend circumferentially around the core pin. In some embodiments, the cross section of the at least one indent can form an arc of a circle. In some embodiments, the circle can have a radius between approximately 0.05 inches and approximately 0.2 inches.

In various embodiments, a needleless medical connector can include a connector housing comprising an inner cavity and a compressible seal positioned at least partially within the inner cavity of the connector housing, the compressible seal having: a body wall that defines an interior space; an upper section, a lower section, and a shoulder between the upper section and the lower section; and a slit on a top of the seal that extends through the top of the seal and into the interior space. The compressible seal can have a first position in which the slit is generally closed to prevent fluid from passing through the slit and a second position in which the compressible seal has been pushed downward by a medical implement and the slit is open to allow fluid to pass through the slit and into the interior space of the compressible seal. At least a portion of the upper section of the compressible seal can have an outer diameter that is greater than an inner diameter of the inner cavity that is aligned with the portion of the upper section when the compressible seal is in the first position, thereby minimizing fluid that can pass between the portion of the upper section of the compressible seal and the connector housing. Such portions of the upper section of the compressible seal can also be configured to remain in contact with walls of the inner cavity as the seal moves from the second position to the first position to ensure that fluid that may be on the walls of the inner cavity, even if outside of the typical fluid path, is directed out of the inner cavity through an upper opening to the inner cavity.

DETAILED DESCRIPTION OF THE PREFERRED EMBODIMENTS

With reference to the attached figures, certain embodiments and examples of fluid flow systems and medical connectors will now be described. Various embodiments described herein are with reference to a three-port stopcock, but they are not so limited. In some aspects, they can be applied to four-port stopcocks, other branched connectors including y-site connectors, or any device that has a flow of fluid and a component such that it can be beneficial to make sure that fluid flushes through the component. Various embodiments relating to a needleless access port can also be applied to any access port within or at the end of a fluid line, for example, a closed female luer connector with an open or closed male luer opposite end. As used herein, the term "fluid" refers to either gases or liquids.

Figure 1:
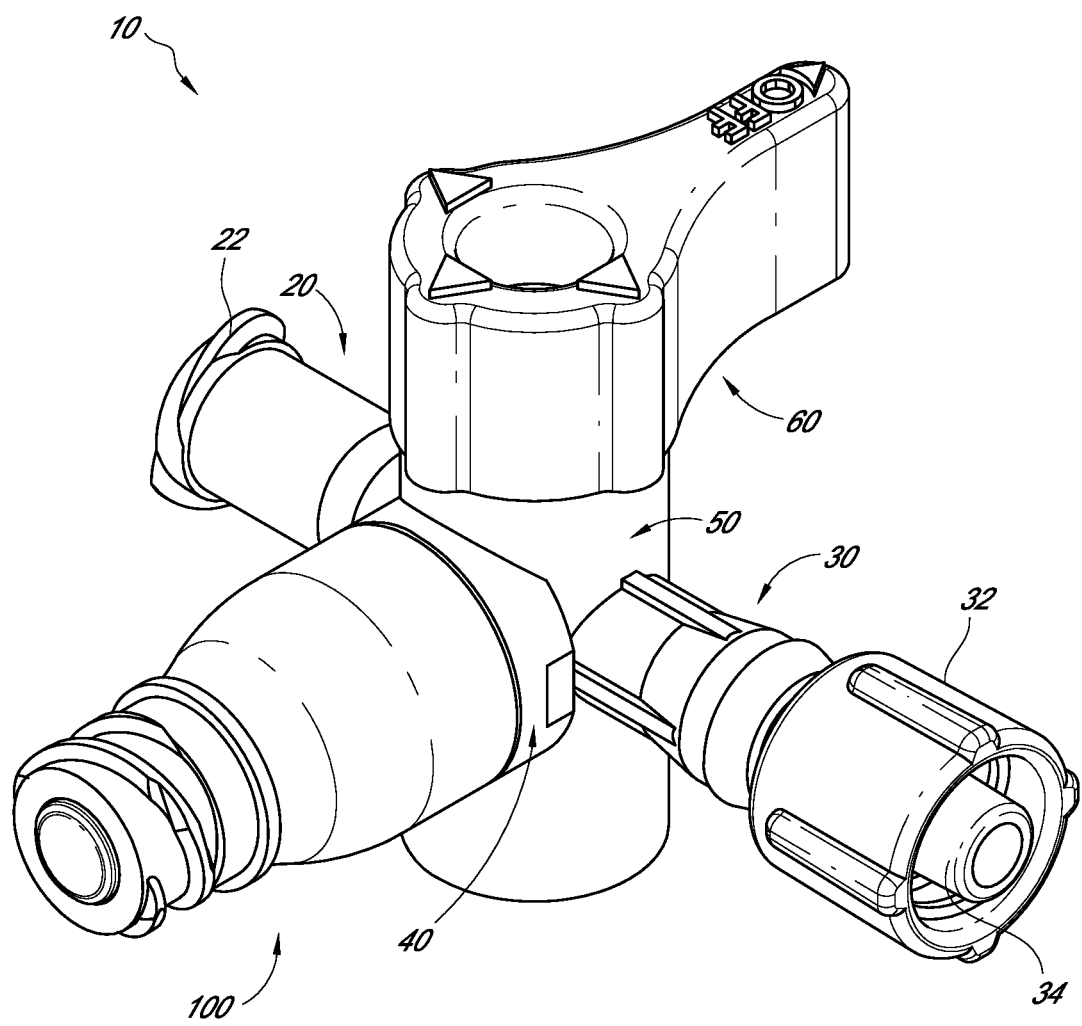
FIG. 1 is a perspective view of one embodiment of a three-way stopcock.

FIG. 1 illustrates one embodiment of a stopcock 10 that can be used within a fluid flow line. The stopcock can include a first port 20, a second port 30 opposite the first port, and a third port 40 between the first and second ports. The ports can be joined by a central connecting portion 50, which can allow fluid to flow from one port to another. A fluid director 60 can be used to adjust the connections between the ports according to the desires of an operator. Thus, depending on the position of the fluid director one or more ports can be in fluid communication with each other or can be blocked from fluid communication with each other. Though shown opaque, in some embodiments one or more components can be translucent, transparent, and/or clear such that the fluid flow path through the components is visible.

In various embodiments, different ports can generally be configured to accommodate any standard medical connector or implement, and can be configured to conform with ANSI (American National Standards Institute, Washington, D.C.) or other applicable standards. The term "medical implement" is used herein to denote any medical device commonly used in the medical field that can be connected or joined with any embodiments of the connectors disclosed herein. Examples of medical implements that are contemplated include, without limitation, tubing, luers, conduits, syringes, intravenous devices (both peripheral and central lines), closable male luer connectors (both integrally formed with a syringe or independent connectors), pumps, piggyback lines, and other components which can be used in connection with a medical valve or connector. Different ports can also be configured to have non-standard connections.

In some embodiments, a first port 20 can have a threaded end 22 that can be used to connect to a threaded medical connector. In some embodiments, the second port 30 can have a male luer lock 32, including a tapered cannula 34. In some embodiments, one or more of the ports can be configured to attach to or be formed with a needleless access port, such as needleless connector 100. In the illustrated embodiment, a needleless connector is attached to the third port, between the first and second ports. In some embodiments, a portion of the needleless connector can be integrally formed with the connecting portion 50. In some embodiments, more than one needleless connector can attach to the stopcock, or a needleless connector can attach to a different port than the third port. In some embodiments, a stopcock 10 can have more than three ports.

When the needleless connector 100 is positioned between the first and second ports, it can be used to access a flow of fluid between the first port 20 and second port 30. The needleless connector can be used to draw fluid from the flow between the first and second ports, from one of either the first or second ports, or the needleless connector can be used to inject a fluid, such as a medicine, into the flow. In some embodiments, it can be desirable for the stopcock to be configured such that a fluid that flows from the first port 20 to the second port 30 can also flow at least partially into the third port and/or a needleless connector attached to the third port. This can help flush a majority of any fluid located within the third port and/or the needleless connector attached to the third port, such as the needleless connector 100. Although various embodiments described herein are with respect to a needleless connector including an internal projection member, any needleless connector may be flushed according to the embodiments described herein.

Figure 2:
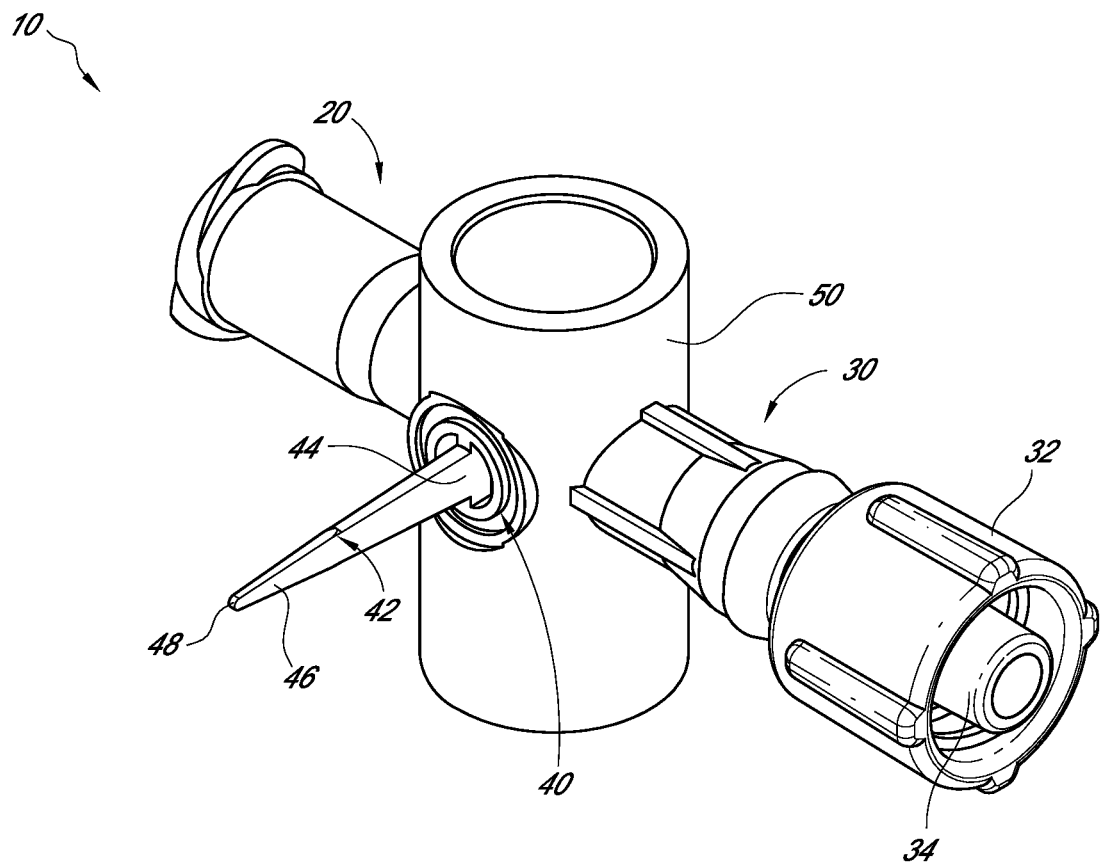
FIG. 2 is a perspective view of the embodiment of FIG. 1 with a needleless connector removed.

FIG. 2 illustrates one aspect of a stopcock 10 that can be used to flush fluid out of a device attached to the third port 40. FIG. 2 is a perspective view of a stopcock 10 with the fluid director 60 and needleless connector 100 both not drawn for the sake of clarity. As illustrated in FIG. 2, the third port 40 can include a fluid diverter 42 that extends away from the connecting central portion 50 of the stopcock. The fluid diverter 42 may be integrally formed with the connection portion 50. In some embodiments, the fluid diverter may be separately formed and subsequently heat staked, RF welded, snap-fit, or otherwise connected to the connecting portion 50.

Though illustrated as a portion of the stopcock 10, fluid diverter 42 may be integrally molded with a portion of the needleless connector. In some embodiments, fluid diverter 42 may be integrally molded with an internal projection, such as internal projection 170 described in greater detail below. In some embodiments, fluid diverter 42 may include more than one portion, and a first portion of the fluid diverter can be connected to the needleless connector and a second portion of the fluid diverter can be connected to the stopcock 50.

A needleless connector attached to the third port may be positioned over the fluid diverter. The fluid diverter can be used to help direct fluid that flows from the first port 20 to the second port 30 into the needleless connector to flush the needleless connector at a distal end thereof. Similarly, the fluid diverter can be used to help direct fluid that flows from the second port 30 to the first port 20 into the needleless connector to flush the needleless connector at a distal end thereof.

The fluid diverter can have a proximal end nearest the connecting portion 50 and a distal end that includes a distal or upper tip 48. The fluid diverter can have a variety of different profiles and can be sized according to the particular needless connector attached to the port with the fluid diverter. In some embodiments, the fluid diverter is widest at its proximal end and narrows toward the distal tip. In some embodiments it can narrow at a constant rate. In some embodiments, the fluid diverter can have a first section 44 that narrows at a constant rate and a second section 46 that narrows at a constant rate different from the rate of the first section. In some embodiments, the second section can narrow at a rate that is greater than the narrowing of the first section. In some embodiments, one or more sections of the diverter can narrow at variable rates. In some embodiments, the profile of the fluid diverter is adapted to track the internal profile of an internal projection member or a valve or seal member of the needleless connector along a substantial portion thereof to direct fluid toward a distal portion of the projection member to effect flushing of the projection member at a distal end thereof. An exemplary internal projection member is described in more detail below.

Figure 3A:
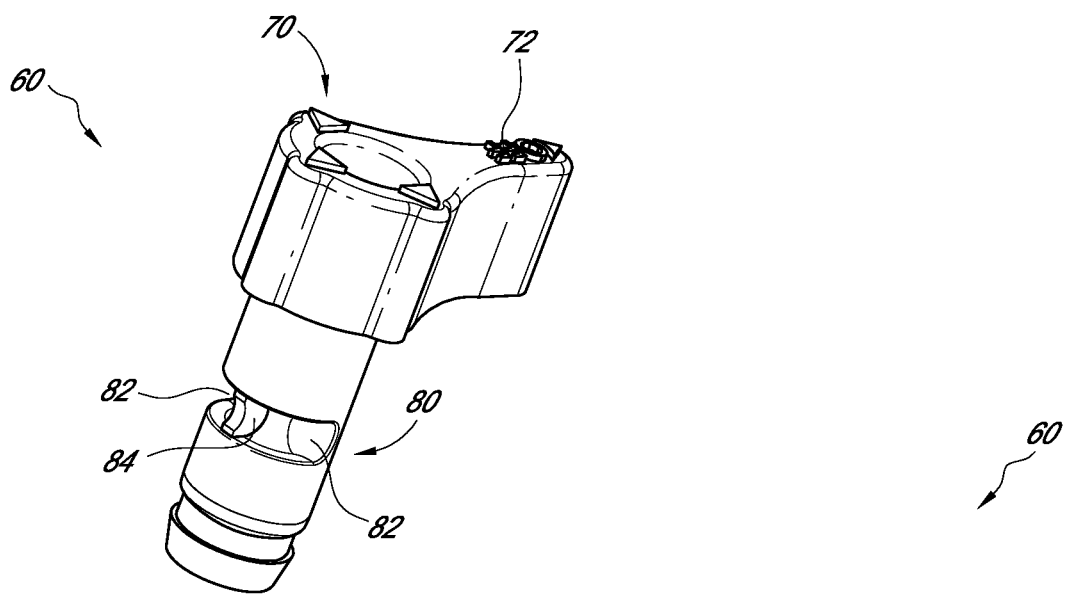
FIG. 3A is a perspective view of a fluid director.
Figure 3B:
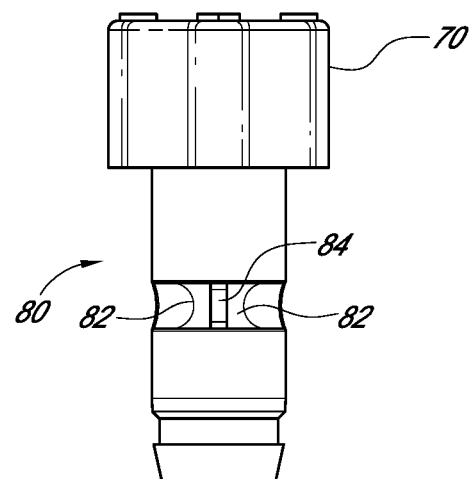
FIG. 3B is a front view of the fluid director of FIG. 3A.
Figure 3C:
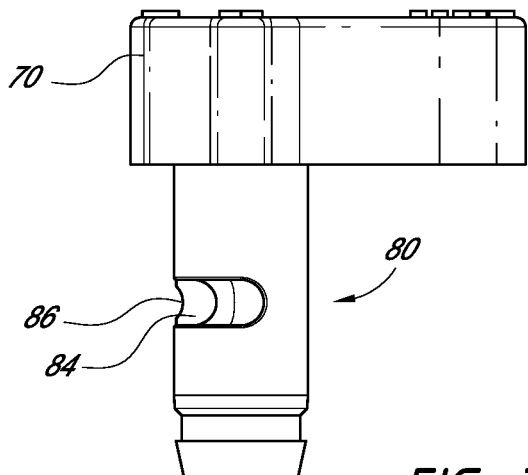
FIG. 3C is a side view of the fluid director of FIG. 3A.

FIGS. 3A through 3C illustrate one embodiment of a fluid director 60 of a stopcock. FIG. 3A illustrates a perspective view of the fluid director, and FIGS. 3B and 3C illustrate front and side views, respectively. As illustrated, a fluid director can comprise an actuator 70, such as a handle. This can be used to move the fluid director and adjust the connections and/or the flow of fluid between the various ports of a stopcock. The actuator can have a variety of informational features 72, such as decals or raise markings, which can be used to inform a user which ports are connected to which ports.

The fluid director 60 can also have a fluid directing section 80 attached to the actuator 70. The fluid directing section can have one or more circumferential recesses 82, which can serve as channels that connect ports to each other when the fluid director is positioned within a stopcock. A flow guide 84 can be positioned between two recesses. As best illustrated in FIG. 3C, in some embodiments the flow guide can comprise a fluid bypass 86 such as a notch or cutout, such that the entire flow guide does not extend all the way to an outer surface of the fluid directing section 80. Though illustrated as a semi-circular depression on the flow guide, other configurations are also possible. For example, such fluid bypass could be angular in some embodiments. In some embodiments, fluid bypass 86 could be a hole extending through the fluid diverter with a smaller cross-sectional area than the cross-sectional area of the fluid path or channel created by the recess 82.

Figure 3D:
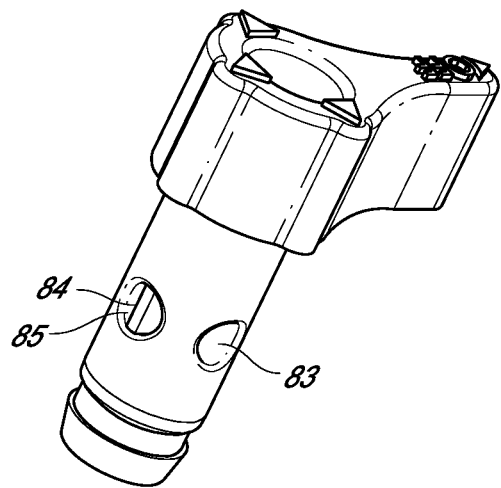
FIG. 3D is a perspective view of a fluid director.
Figure 3E:
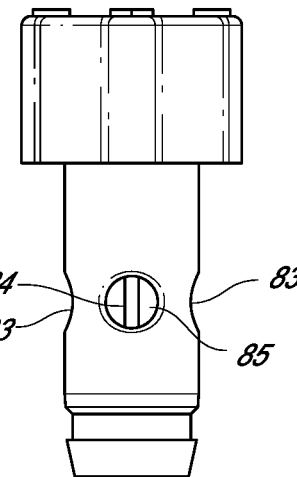
FIG. 3E is a front view of the fluid director of FIG. 3D.
Figure 3F:
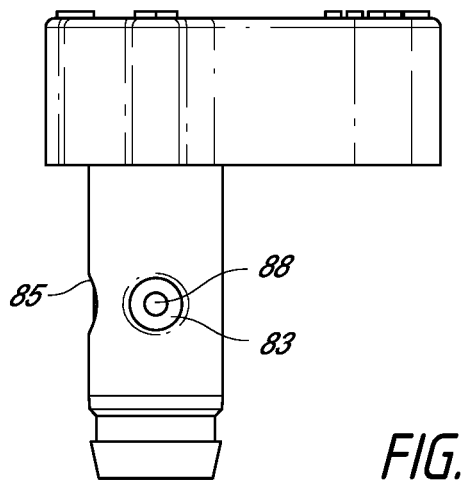
FIG. 3F is a side view of the fluid director of FIG. 3D.

The fluid director can have a variety of configurations other than or in addition to recesses 82 to create flow channels that can be used to selectively connect the first, second, and third ports. For example, in some embodiments the fluid directing section 80 can incorporate holes or passageways therethrough. An example of a fluid director with passageways 83, 85 extending therethrough is shown in FIGS. 3D-3F. In some embodiments, a generally linear primary passageway 83 is configured to extend generally along or parallel to the diameter of the fluid diverter to connect the first and third ports when the fluid director is in the first and fourth position described in greater detail below. In some embodiments a generally perpendicular, secondary passageway 85 can extend from a mid-point of the primary passageway 83 to direct flow toward the third port when the fluid diverter is in the first position. Primary passageway 83 may be substantially bifurcated by a flow guide 84 configured to direct fluid down secondary passageway 85 and into a connector formed at the third port to enhance flushing therein. Flow guide 84 can have a hole 86. In some embodiments, the hole can have a smaller cross-sectional area than the cross-sectional area of the primary passageway 83. In some embodiments, the hole can be centered about a diameter of the fluid director 60. In some embodiments, the hole can be offset from a diameter of the fluid director.

Figure 4A:
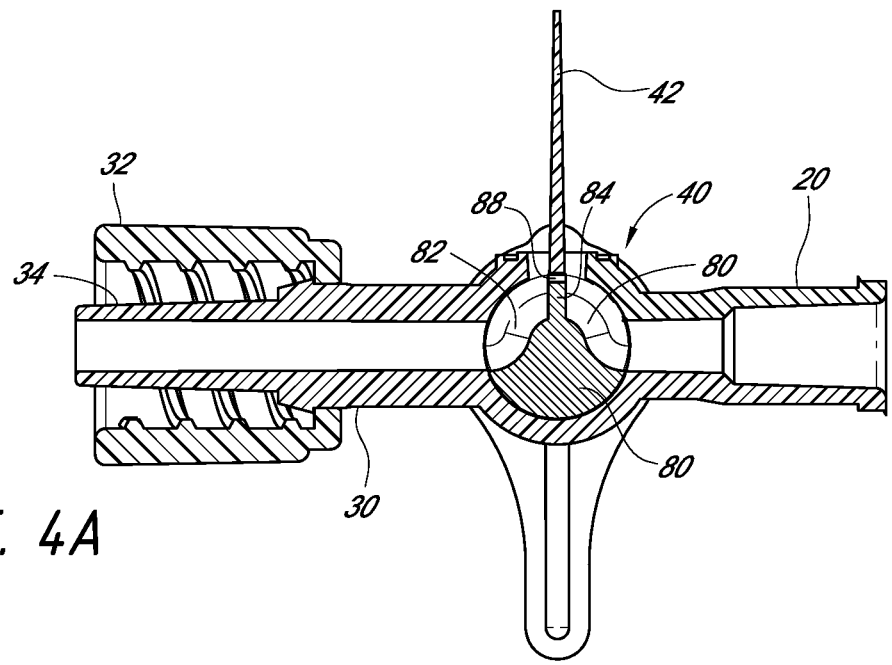
FIGS. 4A-4D are cross-sectional views of a stopcock with a needleless connector removed and with a fluid director rotated to varying positions.

FIGS. 4A through 4D illustrate how different positions of the fluid director can connect different ports of a stopcock. FIGS. 4A through 4D are cross-sectional views of the stopcock. FIG. 4A illustrates the stopcock when the fluid director 60 is in a first position. In the first position, a recess 82 creates a fluid flow channel between the first port 20 and the third port 40. Similarly, a recess 82 creates a flow channel between the second port 30 and the third port 40. Additionally, in embodiments where the flow guide 84 has a fluid bypass 86 that does not extend all the way to an outer surface of the fluid directing section 80, a gap 88 exists between the flow guide 84 and the fluid diverter 42. Thus, the first port 20 and second port 30 are fluidly connected through the gap 88 without having to pass into the third port 40. As discussed above, part of a fluid bypass can also or alternatively extend through the fluid diverter 42. As described in more detail below, the fluid diverter can direct at least part of the flow into the third port.

In some embodiments, the area of the gap 88 can vary as a function of the cross-sectional area of the recesses 82, which defines a cross-sectional area of the fluid flow path within the fluid director 60. For example, in some embodiments the area of the gap can be can be greater than or equal to about 5 percent and/or less than or equal to about 15 percent of the area of the recesses. In some embodiments, the area of the gap can be greater than or equal to about 10 percent and/or less than or equal to about 30 percent of the area of the recesses. In some embodiments, the recesses may not have the same cross-sectional area, or they may not have a constant cross-sectional area. Thus, the area of the gap can also be viewed as a function of the area of the flow guide 84 if it lacked the bypass 86 (i.e., the sum of the cross-sectional area of the flow guide and the bypass). In some embodiments, the area of the gap can be greater than or equal to about 5 percent and/or less than or equal to about 15 percent of the area of the flow guide if it lacked the bypass. In some embodiments, the area of the gap can be greater than or equal to about 10 percent and/or less than or equal to about 30 percent of the area of the flow guide if it lacked the bypass.

Figure 4B:
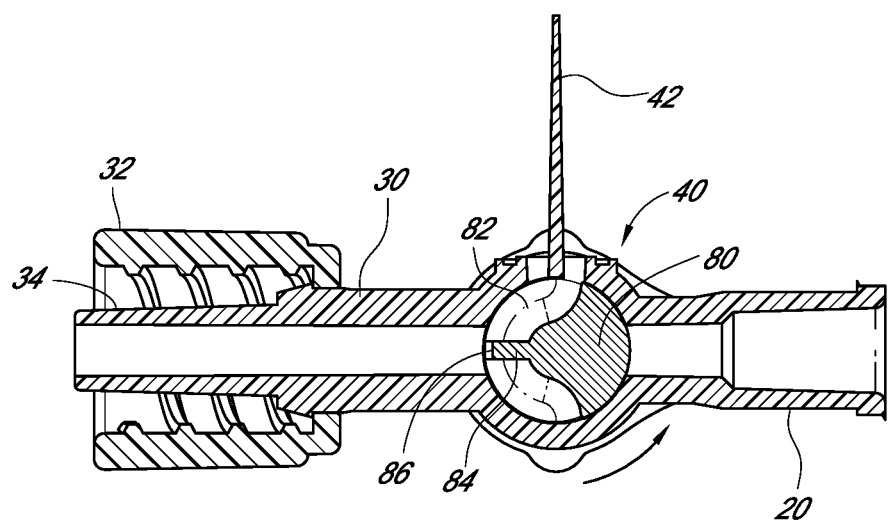

In FIG. 4B, the fluid director has been rotated to a second position such that the flow guide 84 generally points toward the second port 30. In the second position, a recess 82 can form a flow channel between the second port 30 and the third port 40. The fluid directing section 80 blocks fluid flow between the first port 20 and the second and third ports, such that only the second and third ports are fluidly connected.

Figure 4C:
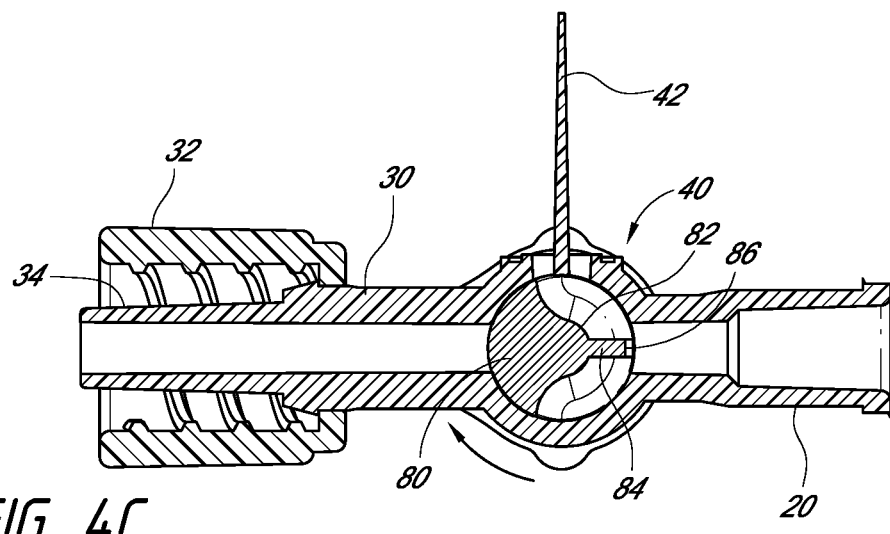

FIG. 4C illustrates a third position, in which the fluid director has been rotated such that the flow guide 84 points generally toward the first port 20. In the third position, a recess 82 creates a fluid flow path between the first port 20 and the third port 40. The fluid directing section 80 blocks the second port 30, such that only the first and third ports are in fluid communication with each other.

Figure 4D:
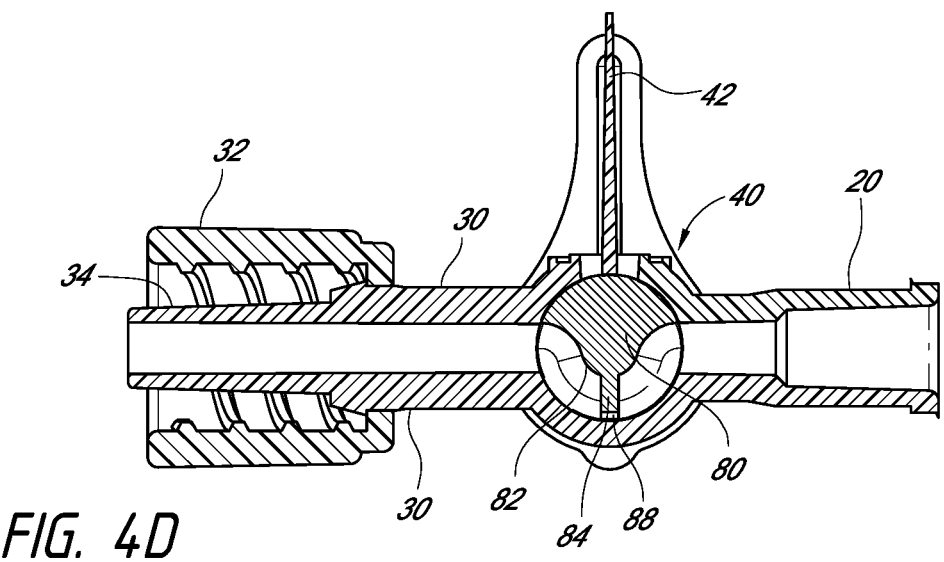

FIG. 4D illustrates a fourth position, in which the flow guide 84 points generally away from the third port 40. In the fourth position, only the first and second ports are in fluid communication with each other and the third part is blocked. Fluid can flow between the first and second ports through the gap 88. The fluid flow guide can also have a variety of positions between the first, second, third, or fourth positions. Though illustrated as a circumferential recess 82, as described above other features and designs can be used, such as holes or passageways, to create flow channels. Additionally, other designs for a fluid bypass can be used, also as described above.

Figure 5A:
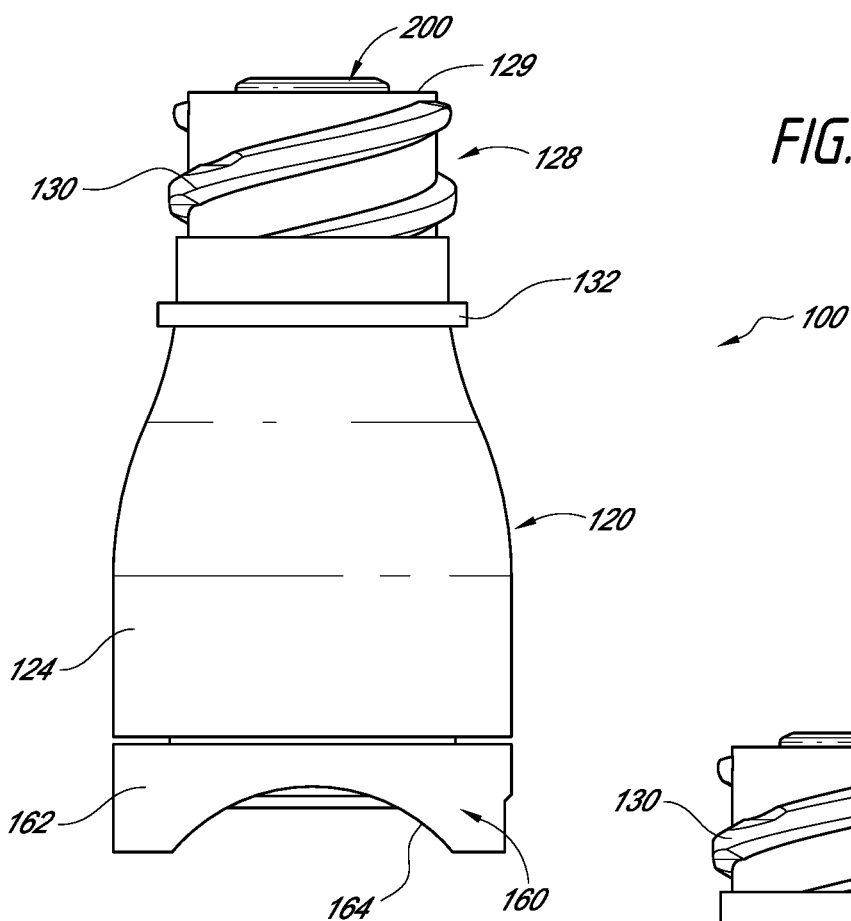
FIG. 5A is a front view of one embodiment of a needleless connector assembly.

FIG. 5A illustrates a front view of one embodiment of a needleless connector 100. The various embodiments of needleless connectors described herein can be positioned on a stopcock port with or without a fluid diverter. The various embodiments of needleless connectors described herein can also be positioned on other branched connectors, as part of other elements within a fluid flow line, or they can be positioned independently within a fluid flow line.

The needleless connector 100 can comprise a base section 160, a housing or body 120, and a seal or valve member 200 positioned at least partially within the body. In some embodiments, the valve member can be generally flush against the top of the body to facilitate aseptic procedures thereon, such as swabbing it with alcohol prior to accessing the connector.

The connector body 120 can include a proximal or lower portion 124 and a distal or upper portion 128 with a distal surface 129. In some embodiments, the upper portion can have threads 130 and can connect to a threaded medical implement, such as a luer connector. In some embodiments, the upper portion can have a shoulder or radial collar 132 that, for example, can be used as a stop for any medical implement attached to the connector. In some embodiments, the base section 160 can be configured to attach to a stopcock. For example, it can have a base portion 162 with a bottom or most proximal surface 168 and a cutout 164 configured to mate with a corresponding section of the port of a stopcock.

The upper portion 128 of the connector body 120 can generally be configured to accommodate any standard medical connector or implement, as described above, including any connector or implement that conforms with ANSI or other applicable standards. In some embodiments, the upper portion can be configured to accommodate nonstandard connections.

In some embodiments, the base section 160 of the connector 100 can similarly be configured to accommodate any standard medical connector or implement. In some embodiments, the connector can attach to a stopcock with such standard connections. In some embodiments, either the upper portion 128 of the connector and/or the base section 160 of the connector can be configured to accommodate non-standard connections.

Figure 5B:
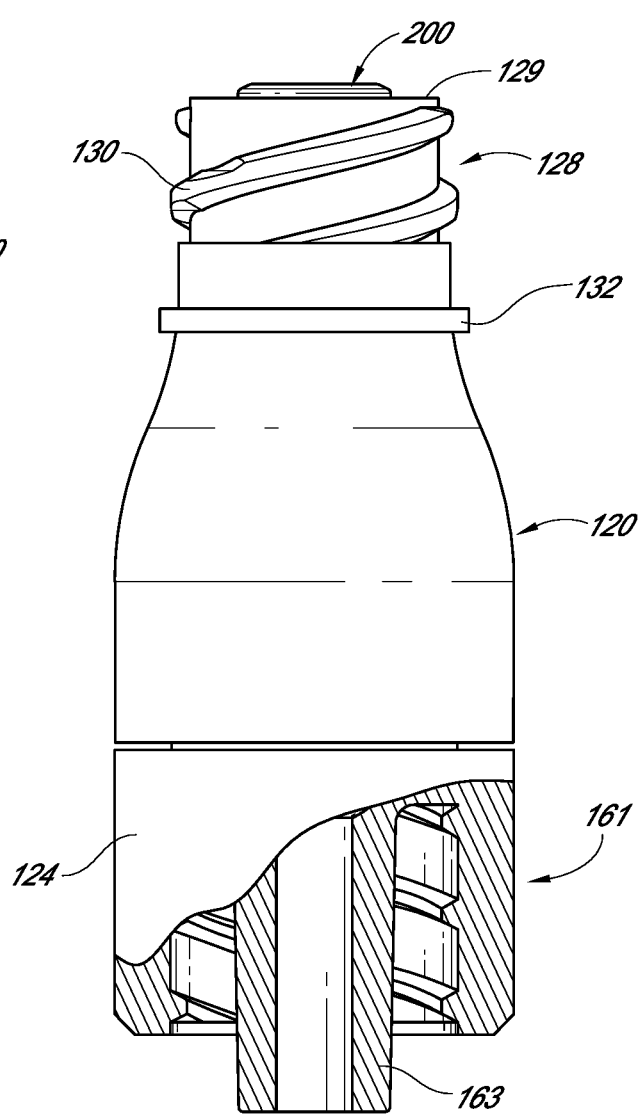
FIG. 5B is a partial cross section of a front view of one embodiment of a needleless connector assembly.

FIG. 5B illustrates one embodiment of a needleless connector 100' that has a base section 160' configured to accommodate a standard medical connector or implement. FIG. 5B is a front view of the needless connector with a partial cross-section that illustrates a male luer lock 161 and cannula 163. Except for having a different type of connection on its base, the needleless connector 100' can otherwise function according to any embodiment described herein and may or may not include an internal fluid diverter.

Figure 6:
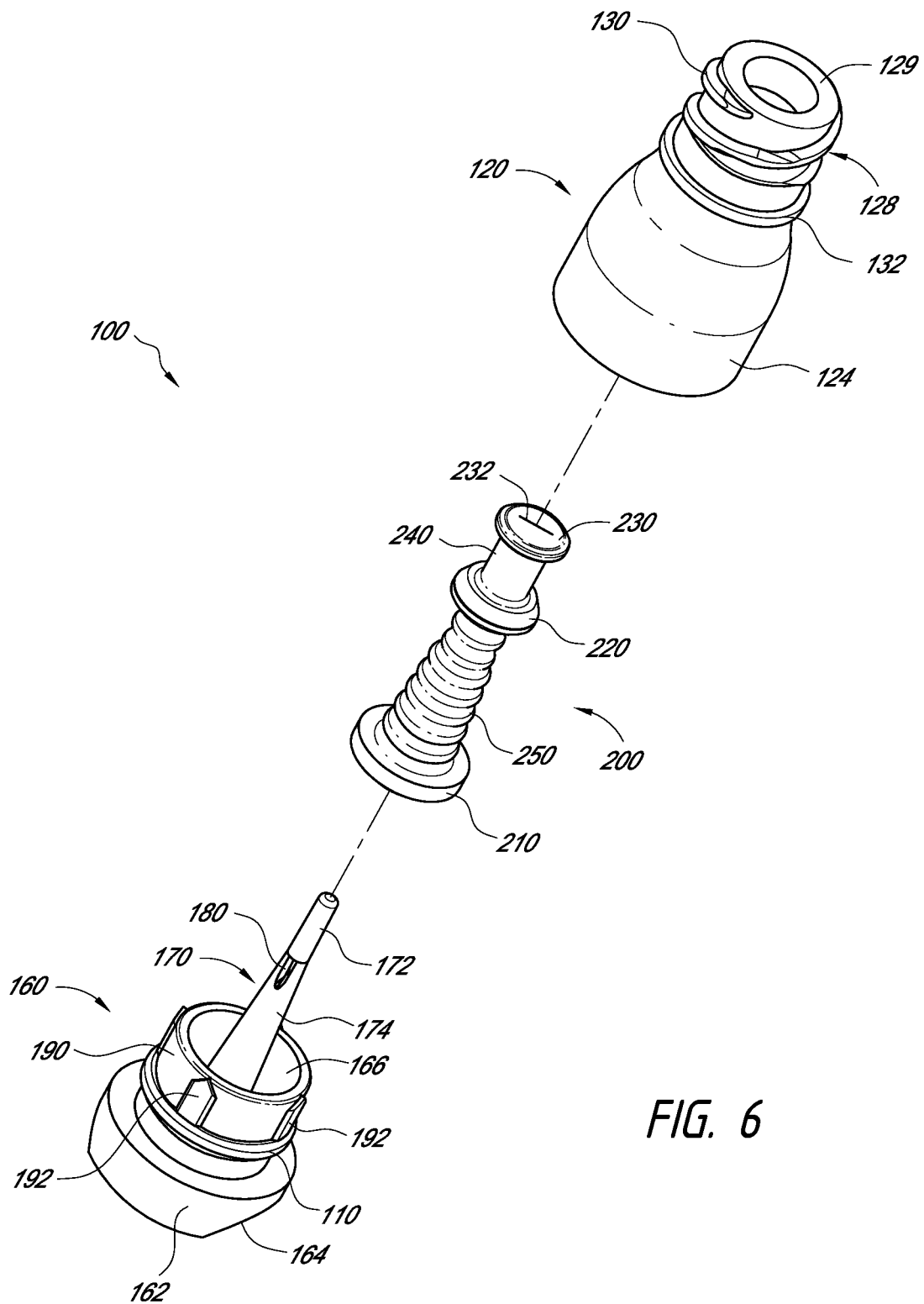
FIG. 6 is an exploded perspective view of a needleless connector assembly.

FIG. 6 illustrates a perspective exploded view of a needleless connector 100. As illustrated, the valve member 200 can include a valve base 210, a ribbed section 250 with a plurality of outer ribs 252, a shoulder 220, a neck portion 240, and a top 230. A slit 232 on the top can be used to provide access to an interior of the valve member. This is described in more detail below.

Figure 8A:
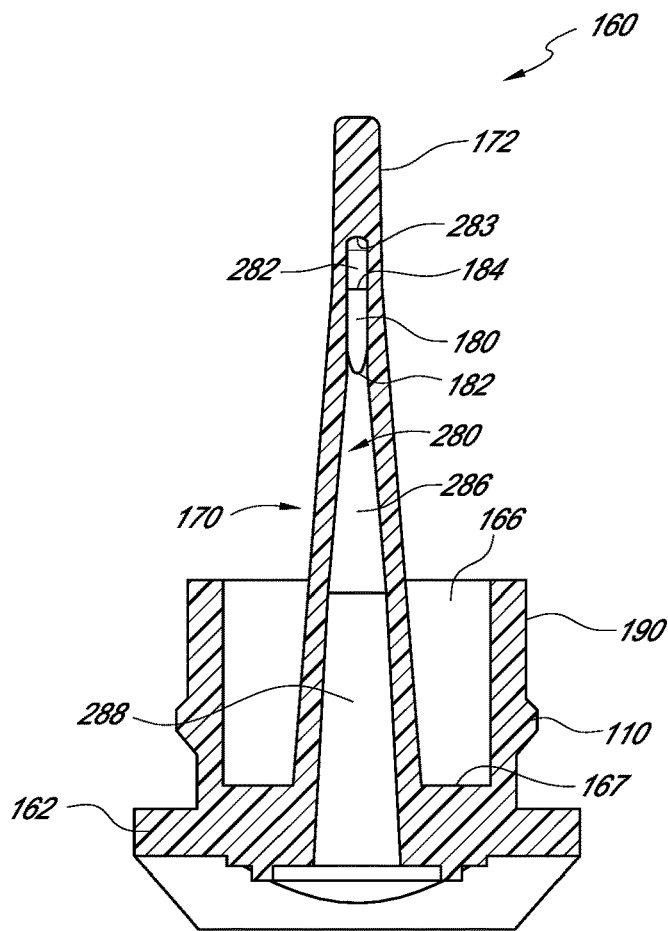
FIG. 8A is a cross-sectional view of a base of a needleless connector taken along the line 8A-8A of FIG. 7A.

The base 160 of the needleless connector can include a collar 190 that defines a cavity 166 with a bottom surface 167 (see, e.g., FIG. 8A). Extending through the collar and out of the cavity is post or internal projection member 170. The projection member can have a projection body 174 and a tip 172. The walls of the projection member can define a hollow interior 280 (see, e.g., FIG. 8A), and one or more openings or windows 180 can extend through an outer wall of the projection and into the interior 280 of the projection. When the needleless connector is assembled, the valve member 200 can be positioned over the projection 170 and the base 210 of the valve can be positioned at least partially within the cavity 166. In some embodiments, base 210 can rest on bottom surface 167 of cavity 166.

In some embodiments, the base 160 of the needleless connector can also include a circumferential projection 110 which can be configured to fit within a corresponding circumferential recess in the body 120 of the needleless connector when the connector is assembled. The base can also have a plurality of vertical projections 192 positioned on at least a portion of the collar. These are described in more detail below.

Figure 7A:
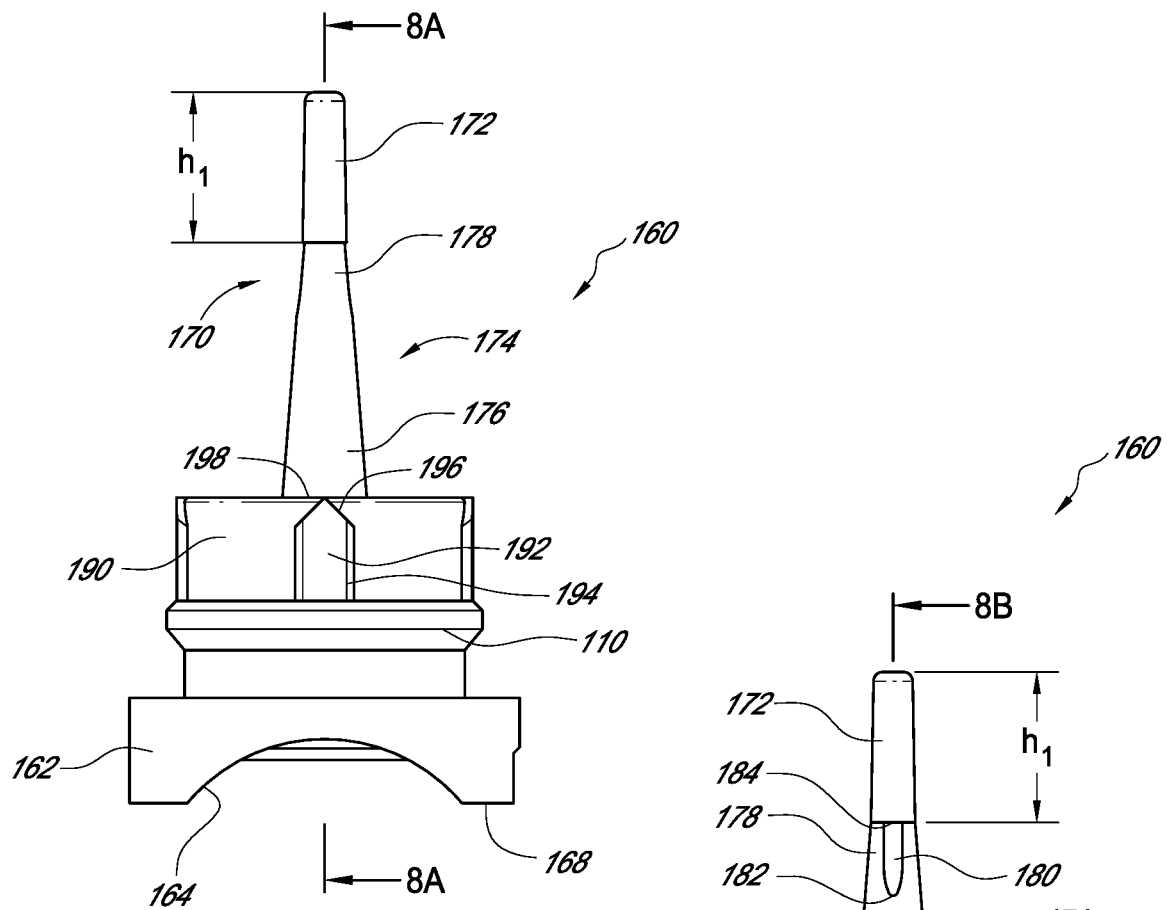
FIG. 7A is a side view of a base of a needleless connector.
Figure 7B:
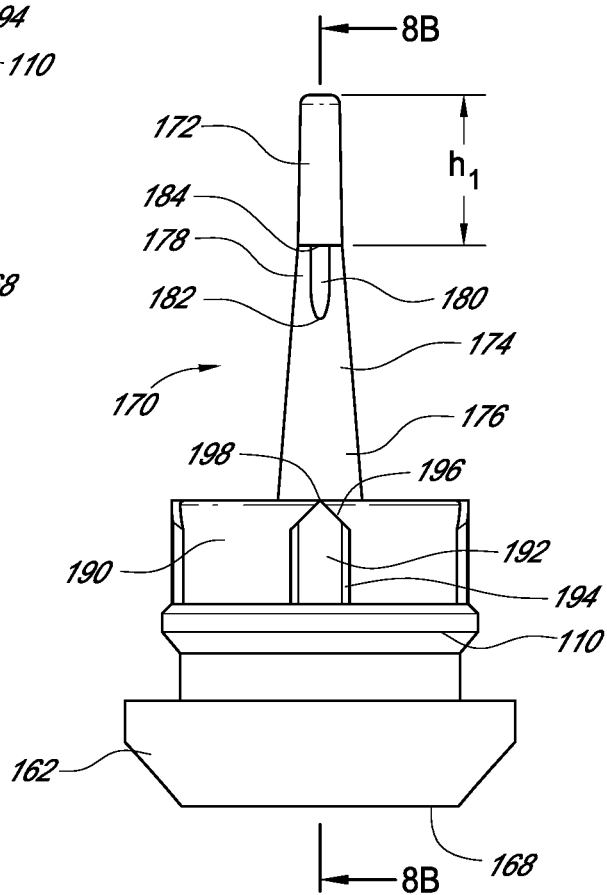
FIG. 7B is a side view of the base of FIG. 7A, rotated approximately 90 degrees.

FIGS. 7A and 7B illustrate front and side views of the base 160 of the needleless connector. FIG. 7B illustrates a view that is rotated 90° from that of FIG. 7A. The projection 170 of the base can have a proximal end nearest the collar 190 and a distal end at the tip 172. The tip 172 can have a height $h_1$ measured from the top 184 of opening 180 to the end of the tip 172.

In some embodiments, the projection can be widest at the proximal end and narrow as it approaches the distal tip. In some embodiments, the projection 170 can narrow at different rates from its proximal end to the distal-most end of the tip 172. For example, as illustrated, the projection body 174 can have a proximal section 176 and a distal section 178. The proximal section can narrow at a first rate and the distal section can narrow at a second rate different from the first rate. As illustrated, the second rate is greater than the first rate, but in some embodiments the second rate can be less than the first rate. As illustrated, the tip 172 can narrow as well. In some embodiments, the tip can maintain a constant width. In some embodiments, one or more sections of the projection body 174 can maintain a constant width.

FIG. 7B illustrates an opening 180 in the projection body 174. As mentioned above, the opening can pass through an outer wall of the projection 170 and into an interior of the projection. The opening can have a variety of shapes and orientations. In some embodiments, it can be a longitudinally oriented oval shape, or any other geometric shape in any other direction, e.g. round, rectangular, square, or the like. In some embodiments, the projection can have more than one opening. Preferably, the projection has two openings positioned on opposite sides of each other around the projection. Each opening can have a bottom or proximal end or surface 182 and a top or distal end or surface 184. In some embodiments, the top of the opening can be defined by a lower end of the tip 172 of the projection. In some embodiments, the entire opening can be positioned within a distal portion 178 of the projection body. In some embodiments, a portion of the opening can be in both a distal section of the projection body and a proximal section 176 of the projection body.

In some embodiments, the internal projection 170 can be sized to provide varying flow rates when connected to a standard IV bag. For example, with an IV bag operating under gravity pressure, in some embodiments an internal projection can be sized to allow a flow rate of greater than or equal to approximately 50 mL/minute and/or less than or equal to approximately 150 mL/minute. In some embodiments, with an IV bag operating under gravity pressure, an internal projection can be sized to allow a flow rate of greater than or equal to approximately 75 mL/minute and/or less than or equal to approximately 125 mL/minute. In some embodiments, with an IV bag operating under gravity pressure, an internal projection can be sized to allow a flow rate of greater than or equal to approximately 90 mL/minute and/or less than or equal to approximately 110 mL/minute.

The vertical projections 192 on the collar 190 of the base 160 of the needleless connector can be used to align the base with the body of the needleless connector during assembly. In some embodiments, the vertical projections can have vertical side surfaces 194 that connect to angled upper surfaces 196 that meet at an edge 198. The body of the needleless connector can have corresponding projections, discussed below, that can interface with the projections 192 and cause the body to rotate into position.

In the illustrated embodiment the base 160 has four vertical projections. In some embodiments, the base can have more or fewer than four vertical projections. Preferably, the vertical projections are spaced symmetrically about the collar 190.

Figure 8B:
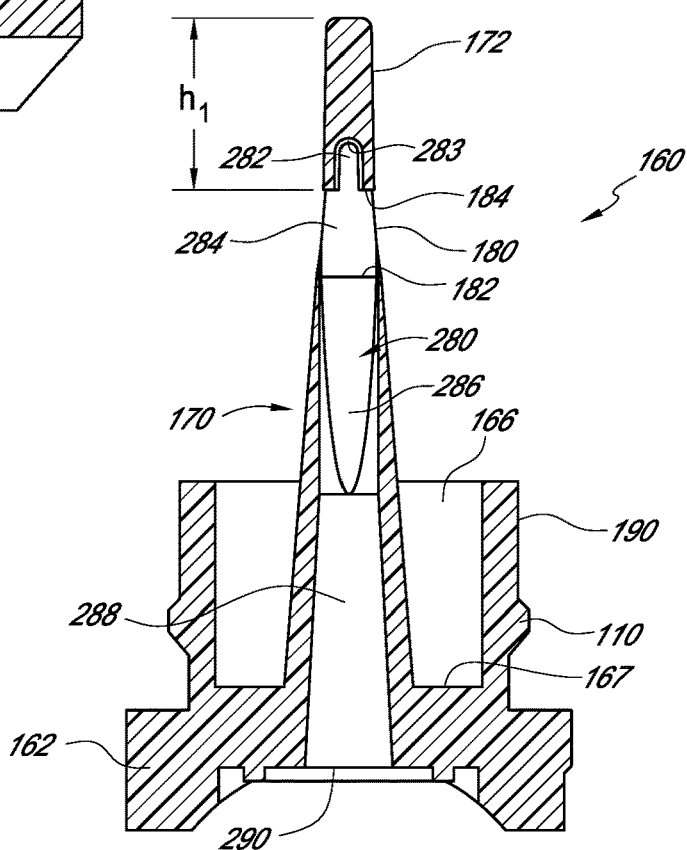
FIG. 8B is a cross-sectional view of a base of a needleless connector taken along the line 8B-8B of FIG. 7B.

FIGS. 8A and 8B are cross-sectional views of the base 160 of a needleless connector. FIG. 8A is a cross-sectional view taken on the line 8A-8A illustrated in FIG. 7A, and FIG. 8B is a cross-sectional view taken on the line 8B-8B illustrated in FIG. 7B. FIGS. 8A and 8B illustrate the interior 280 of the projection, which is defined by the walls of the projection. The interior can be described with respect to a plurality of sections defined by different sizes, shapes, interior wall angles, and/or the location of openings 180. Thus, for example, in some embodiments the interior 280 can have an uppermost or distal most section 282 and an opening section 284 that is aligned with the openings 180 of the projection. The distal-most section can include a distal most surface 283 of the interior of the projection.

In some embodiments, the interior 280 can have an intermediate section 286, below the opening section, and a bottom section 288. In some embodiments, the bottom section can have a generally circular cross section. In some embodiments, the bottom section can have a frustoconical shape such that it narrows as it moves up from an opening 290 at its base. The intermediate section 286 can also narrow from the bottom section 288 to the opening section 284. In some embodiments, the intermediate section can narrow at different rates in different planes. Thus, for example, in some embodiments the intermediate section can narrow at a slower rate in the plane of FIG. 8A than in the plane of FIG. 8B.

Figure 9:
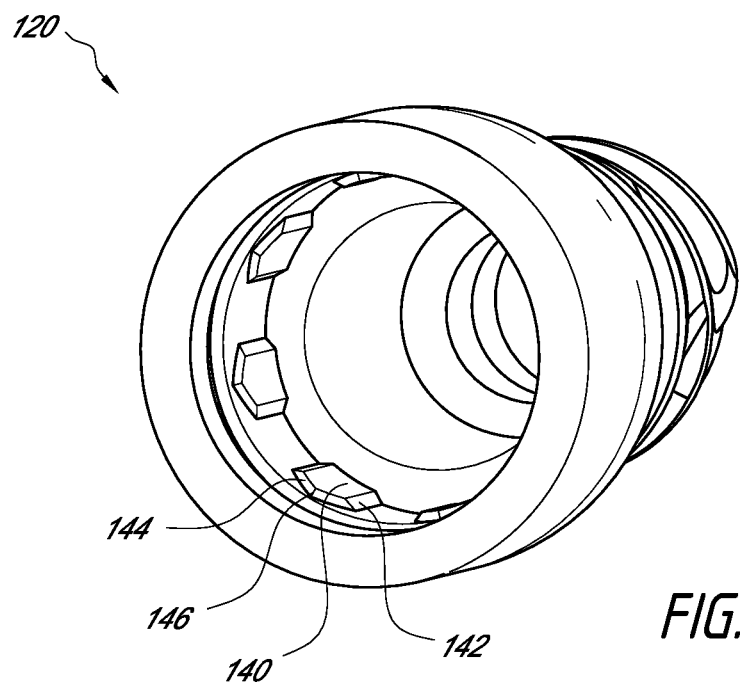
FIG. 9 is a bottom perspective view of a body of a needleless connector.

FIG. 9 illustrates a bottom perspective view of a body 120 of a needleless connector. As illustrated, the body can have a plurality of vertical projections 140 positioned in an interior of the body. Preferably, the vertical projections are oriented symmetrically about the body of the needleless connector.

Each vertical projection can have two vertical side surfaces 142, two angled lower surfaces 144, and a bottom edge 146 where the angled lower surfaces join. When the body 120 of the needleless connector is joined with the base 160, if the two components are not properly aligned the angled lower surfaces 144 of the body can contact the angled upper surfaces 196 of the base (described with reference to FIGS. 7A and 7B). The contact between the two surfaces can rotate the body of the needleless connector and the base of the needleless connector relative to each other until a vertical projection 192 of the base is oriented such that it can fit between vertical projections of the body. In some embodiments, the body and base can have the same number of projections. In some embodiments, one of the body or the base can have a greater number of projections than the other of the body or the base.

Figure 10:
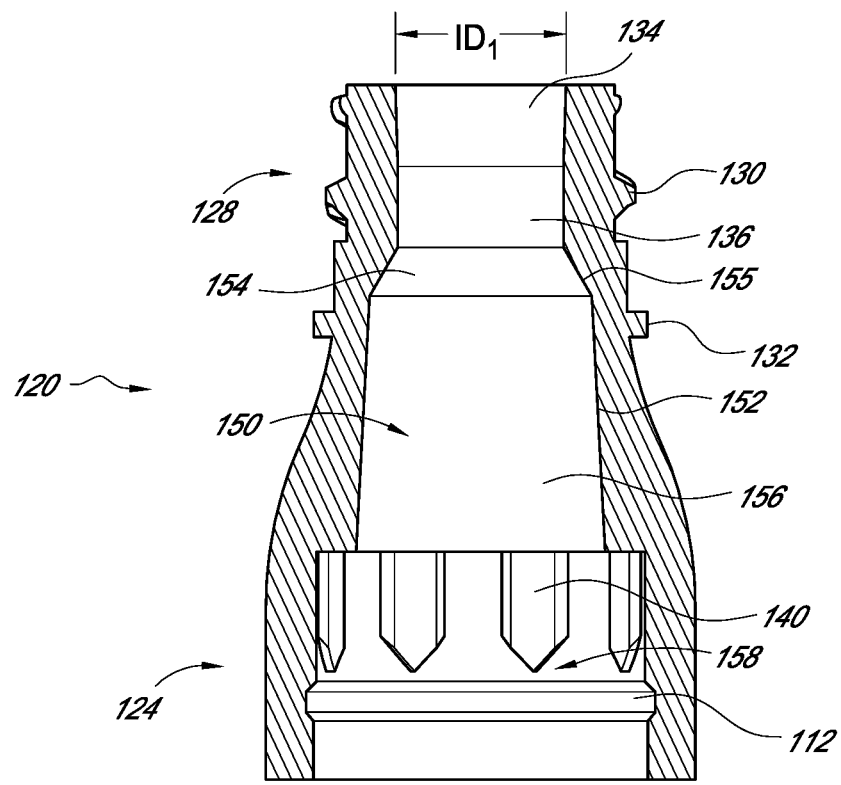
FIG. 10 is a cross-sectional view of a body of a needleless connector.

FIG. 10 illustrates a cross-sectional view of the body 120 of a needleless connector. As illustrated, the body can have an interior cavity 150 defined by an interior wall 152 of the body. Like the interior of the base of a needleless connector, the interior cavity of the body can be described with respect to various sections. For example, in some embodiments the upper portion 128 of the body can have one or more sections. In the illustrated embodiment, the upper portion has an upper section 134 and a lower section 136. In some embodiments, these sections can independently widen or narrow, moving away from the lower portion 124 of the body. In some embodiments they can have a generally constant width or inner diameter. In the illustrated embodiment, upper section 134 includes a taper consistent with international standards for luer connectors and lower section 136 has a generally constant inner diameter. Generally, the largest inner diameter $ID_1$ of the upper portion 128 can be at the very top of the body 120. If the upper portion tapers, it can have smaller inner diameters below the top of the body 120.

In some embodiments, one or both of the lower section 136 and upper section 134 can have roughened walls. In some embodiments, the upper section 134 can have a roughened wall and the lower section 136 can have a generally smooth wall. In some embodiments, the lower section 136 can have roughened walls and the upper section 134 can have generally smooth walls. In some embodiments, both can be smooth.

A transition section 154 can connect the portion of the cavity 150 within the upper portion 128 of the needleless connector body 120 to a main section 156 of the cavity within the lower portion 124 of the connector body. Preferably, the width of the transition section narrows from a proximal to a distal end of the transition section 154, thereby forming a shoulder 155. Beneath the main section 156 of the cavity in the lower portion 124 of the connector body is a base receiving section 158. This section can receive the base 162 and collar 190 of the base 160 of the needleless connector. As illustrated, the base receiving section can have a circumferential recess 112 which can be adapted to receive the circumferential projection 110 of the needleless connector base. These features can provide a snap-fit between the base and the body. In some embodiments, in addition to or instead of having the projections to help join the base and the body, the base and the body can be welded together or secured by other means when the needleless connector is assembled.

Figure 11A:
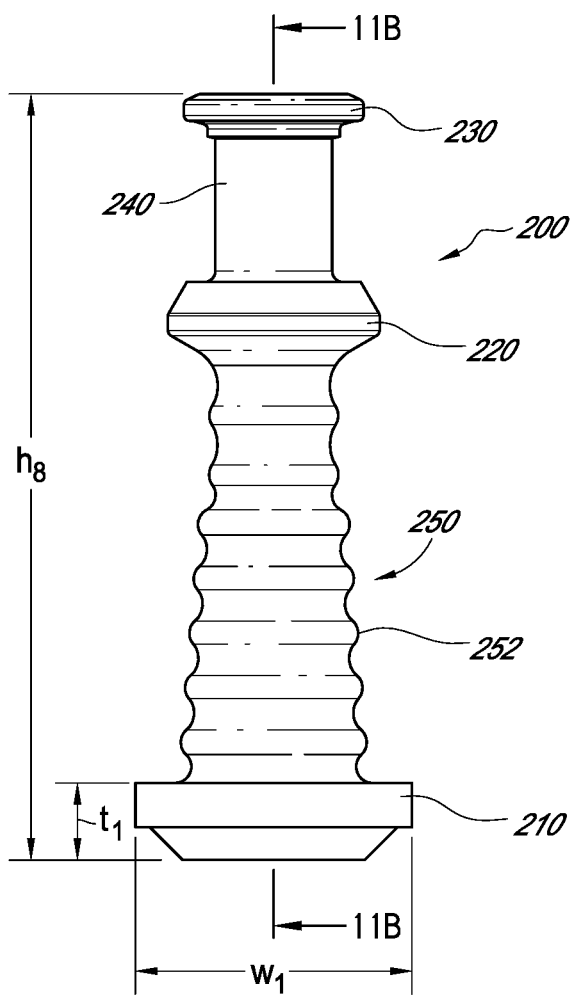
FIG. 11A is a front view of a valve member of a needleless connector.
Figure 11B:
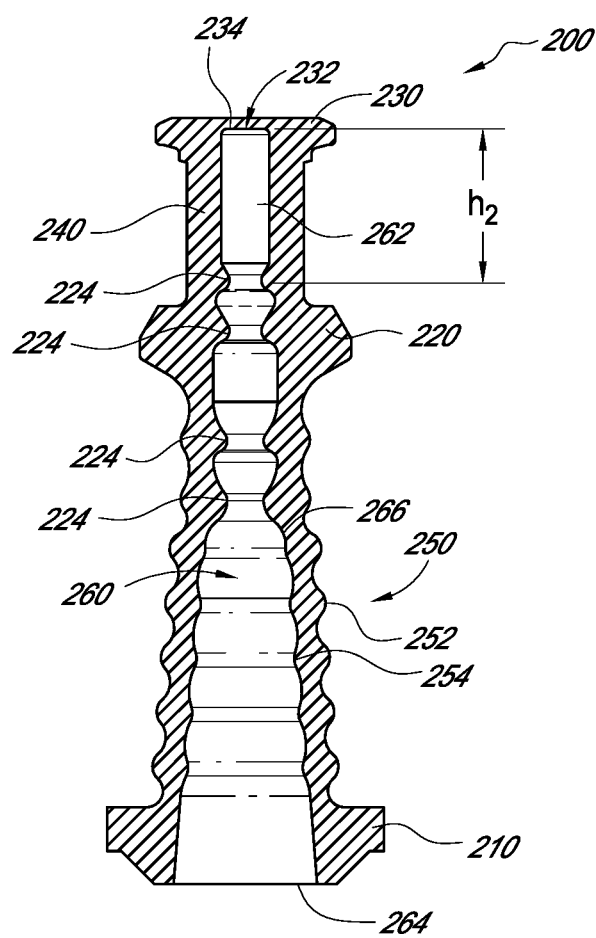
FIG. 11B is a cross-sectional view of the valve member of FIG. 11A.

FIGS. 11A and 11B illustrate one embodiment of a valve member 200 of a needleless connector. The valve member 200 and other valve member embodiments described herein can be used with a variety of needleless connectors, including needless connectors that have an internal projection, needleless connectors that lack an internal projection, and other types and designs of connectors. FIG. 11A is a front view and FIG. 11B is a cross-sectional view of the valve member. With the exception of a slit 232 that passes through the top 230 of the valve member, the valve member can be symmetrical about its longitudinal axis. As discussed above, the valve member can have a base 210, a ribbed section 250 with a plurality of inner ribs 254 and outer ribs 252, a shoulder 220, and a neck 240 between the shoulder and the top 230. In some embodiments, the ribbed section can be configured to allow the valve member to compress a desired amount when a medical implement is used to access a needleless connector with the valve member. In some embodiments, the ribbed section can have generally similar ribs and rib spacing. In some embodiments, the ribbed section can have ribs of different sizes or ribs spaced differing distances from each other. Other shapes and configurations of a valve member are contemplated.

Figure 13:
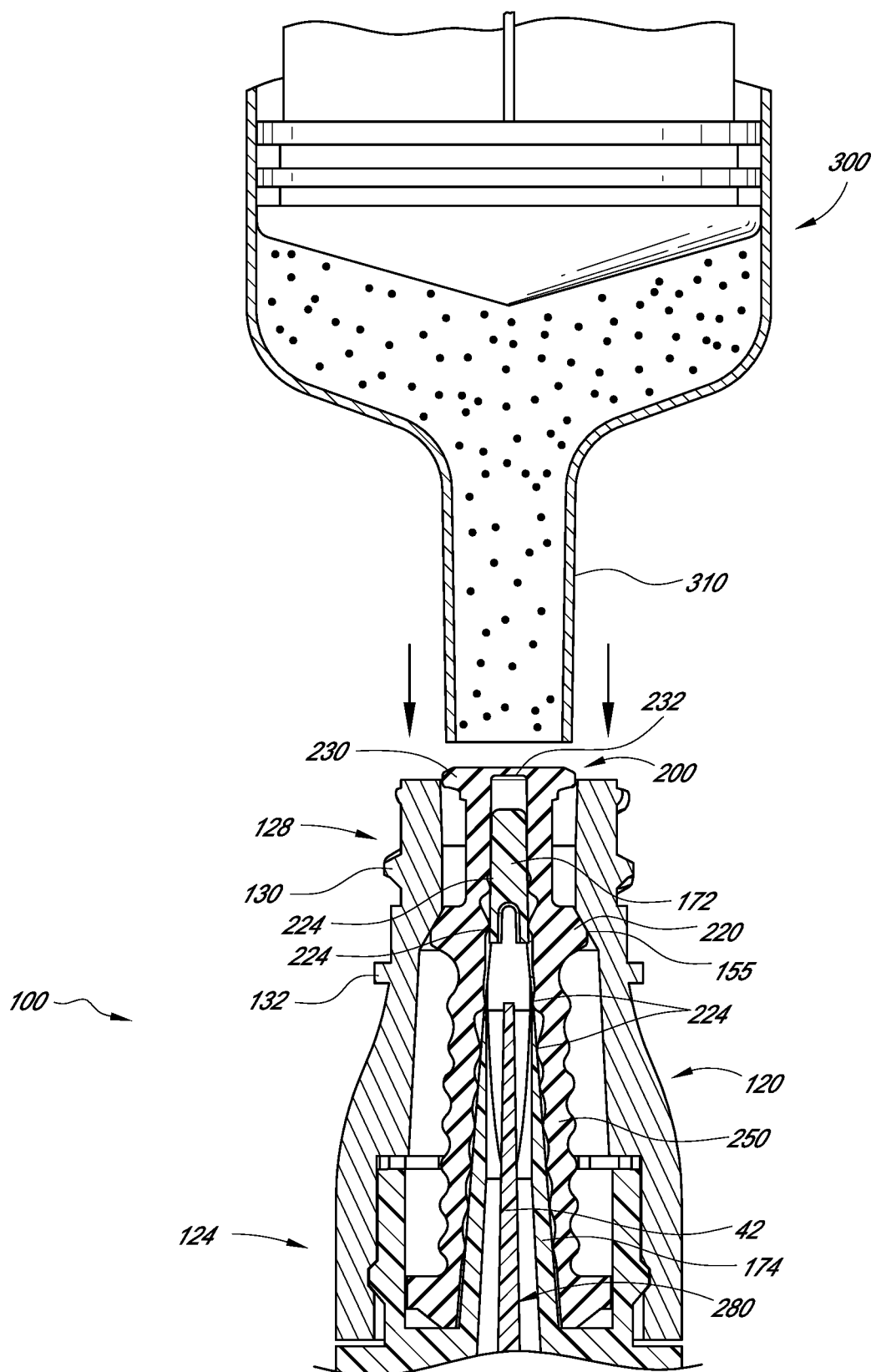
FIG. 13 is a cross-sectional view of a medical implement and a needleless connector that is attached to a port of a stopcock.
Figure 14:
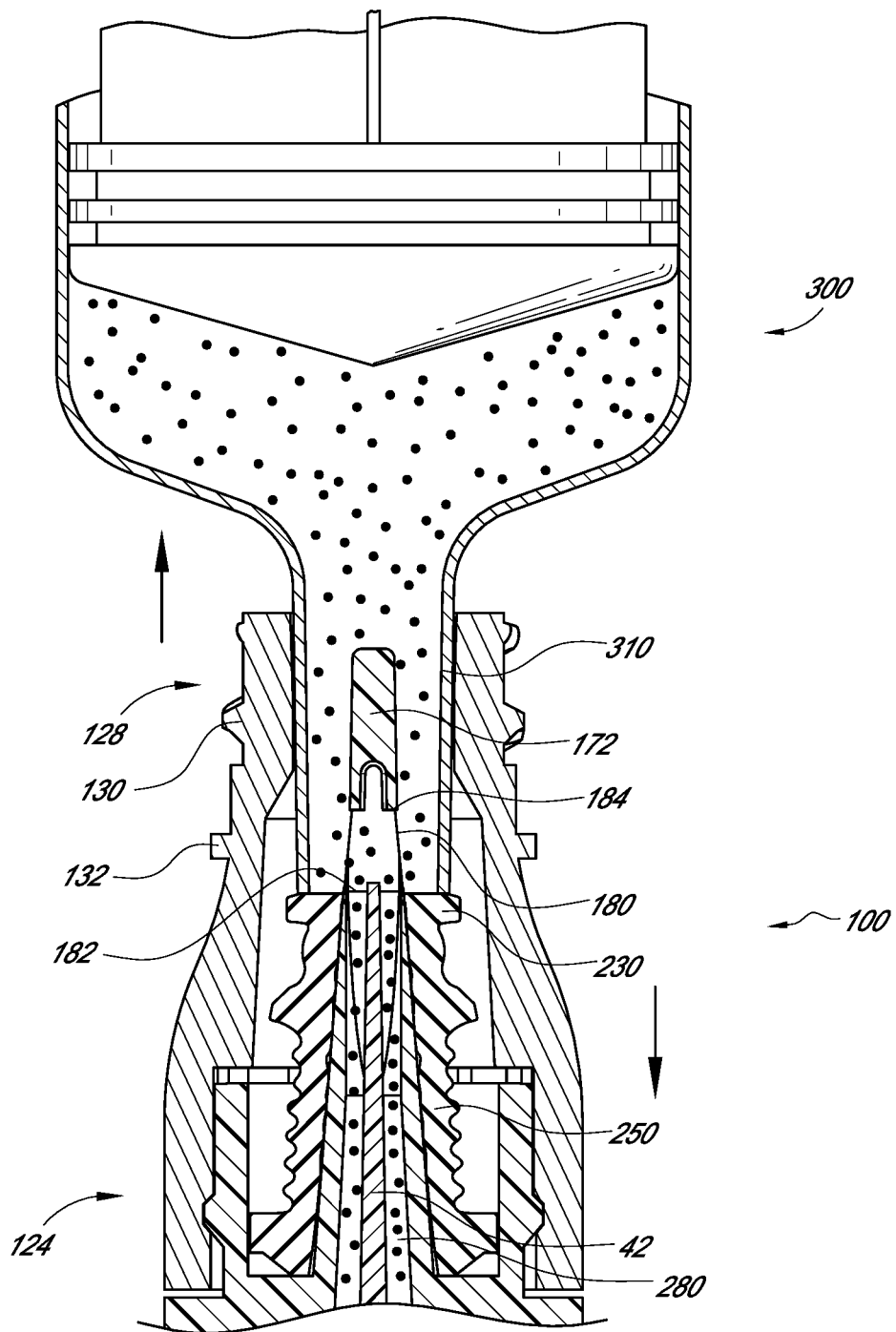
FIG. 14 is a cross-sectional view of a medical implement inserted into a needleless connector.

As illustrated in FIG. 11B, the valve member can have an interior space 260 that extends from an upper interior section 262 immediately below the slit to an opening 264 at the bottom of the valve member. When the needleless connector is fully assembled, the internal projection member can at least partially extend into the interior of the valve member. In some embodiments, when assembling a needleless connector, an oil or other lubricant can be inserted into the interior space 260 and/or onto the internal projection member to help limit friction between the valve member 200 and internal projection member. Limiting friction can help improve the transition between an opened position and a closed position of the valve member within an assembled needleless connector. These positions are illustrated in FIGS. 13 and 14, discussed below.

In some embodiments the base 210 can have a thickness $t_1$ and a width $w_1$ (illustrated in FIG. 11A). Varying the thickness and/or width can affect the structural properties of the valve, which can impact its ability to compress and impact aspects of its manufacture. In some embodiments, the ratio of the width $w_1$ to the thickness $t_1$ can be greater than or equal to approximately 2 and/or less than or equal to approximately 5. In some embodiments, the ratio of $w_1$ to $t_1$ can be greater than or equal to approximately 3 and/or less than or equal to approximately 4. In some embodiments, the ratio of $w_1$ to $t_1$ can be greater than or equal to approximately 3.25 and/or less than or equal to approximately 3.75.

In some embodiments, the total height of the valve $h_8$ and the thickness $t_1$ can also be independently varied to affect the structural properties of the valve. In some embodiments, the ratio of the height $h_8$ to the thickness $t_1$ can be greater than or equal to approximately 8 and/or less than or equal to approximately 12. In some embodiments, the ratio of $h_8$ to $t_1$ can be greater than or equal to approximately 9 and/or less than or equal to approximately 11. In some embodiments, the ratio of $h_8$ to $t_1$ can be greater than or equal to approximately 9.5 and/or less than or equal to approximately 10.5. In some embodiments, the ratio of $h_8$ to $t_1$ can be greater than or equal to approximately 9.7 and/or less than or equal to approximately 10.1.

As illustrated in FIG. 11B, an interior surface 266 of the valve member (or an outer surface of the interior space 260) can have a variety of surface features. Some of these features can help maintain desired sealing characteristics against the internal projection member when it is positioned within the valve member. For example, in some embodiments the valve member can have a plurality of sealing rings 224. The sealing rings can be internal projections that preferably extend circumferentially around the entire interior surface of the valve member. In some embodiments, as illustrated, the valve member can have four sealing rings 224. The sealing rings can be positioned such that they can contact the projection at different desired locations along the projection. In some embodiments, the sealing rings can be spaced approximately an equal distance apart. In some embodiments, the top two sealing rings can form a first set and the bottom two sealing rings can form a second set. In some embodiments, the sealing rings of the first set can be separated a first distance approximately equal to a second distance between the sealing rings of the second set, but the distance between the first set and the second set can be greater than or less than the first and second distance. Other spacing arrangements are contemplated. In some embodiments, discussed in more detail below, the valve member can have more or fewer sealing rings 224.

Figure 11C:
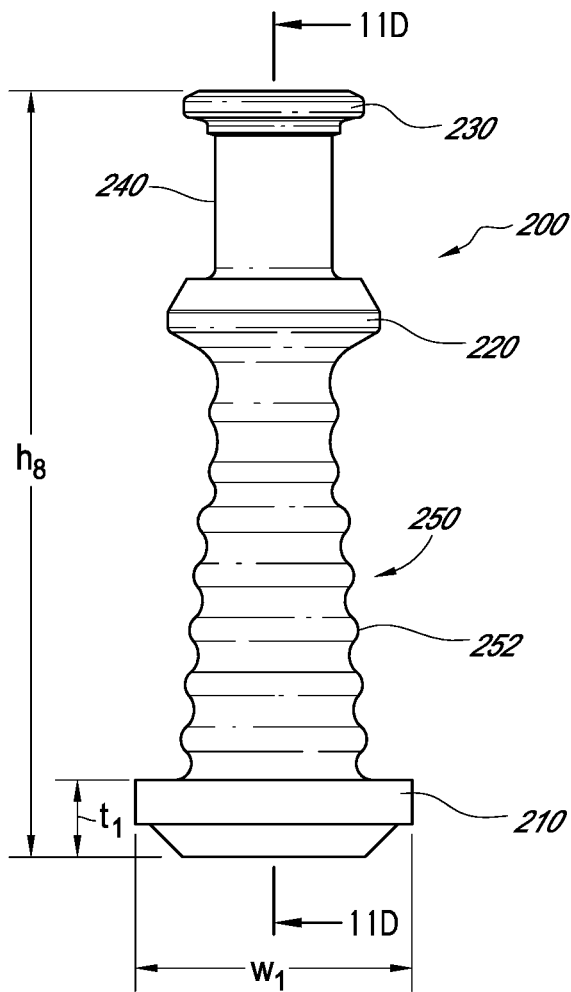
FIG. 11C is a front view of a valve member of a needleless connector.
Figure 11D:
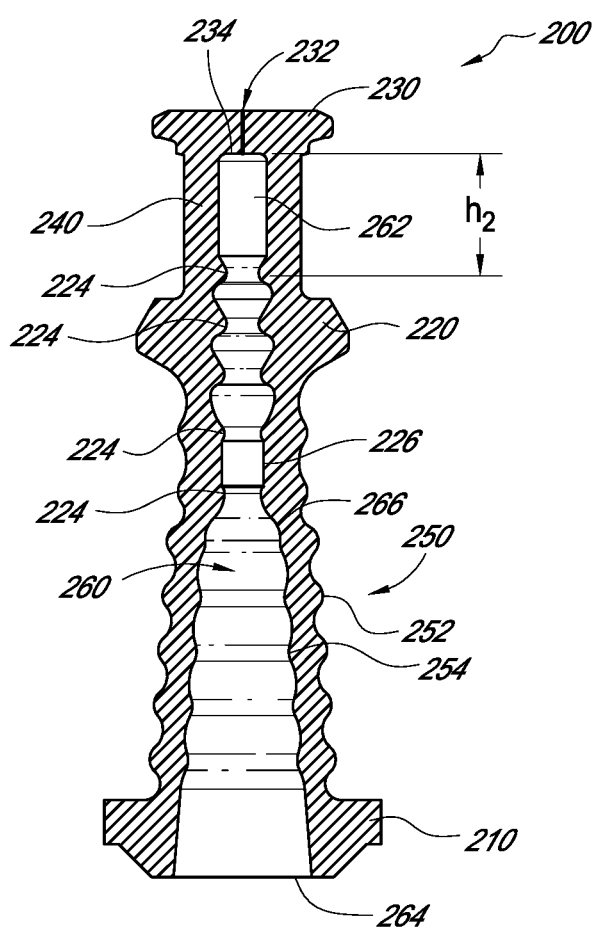
FIG. 11D is a cross-sectional view of the valve member of FIG. 11C.

For example, FIGS. 11C and 11D illustrate one embodiment of a valve member 200 that can have five sealing rings 224. In some embodiments, one or more sealing rings can be joined by a contact portion 226, which can be configured to contact an internal projection member when it is positioned within the valve member. As illustrated, a contact portion can be between the bottom two sealing rings. In some embodiments, it can be between other sealing rings, such as the top two sealing rings. A contact portion is discussed in more detail with respect to FIGS. 17A and 17B. FIGS. 11C and 11D also illustrate an embodiment of a valve member 200 with a thicker top 230 than the top of the embodiment of FIGS. 11A and 11B. This is also discussed in more detail with respect to FIGS. 17A and 17B.

The ribbed section 250 of the valve member can have a plurality of interior ribs 254 on the interior surface 266 of the valve member. The valve member can also have a height $h_2$ defined as the distance between the uppermost sealing ring 224 and a bottom interior surface 234 of the top 230 of the valve member (i.e., an uppermost surface of the interior space 260 of the valve member).

Figure 11E:
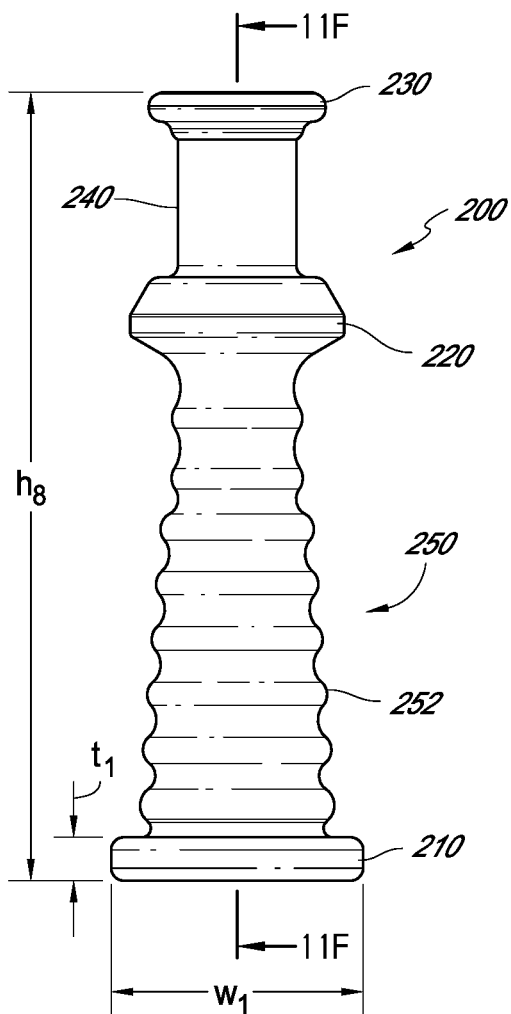
FIG. 11E is a front view of a valve member of a needleless connector.
Figure 11F:
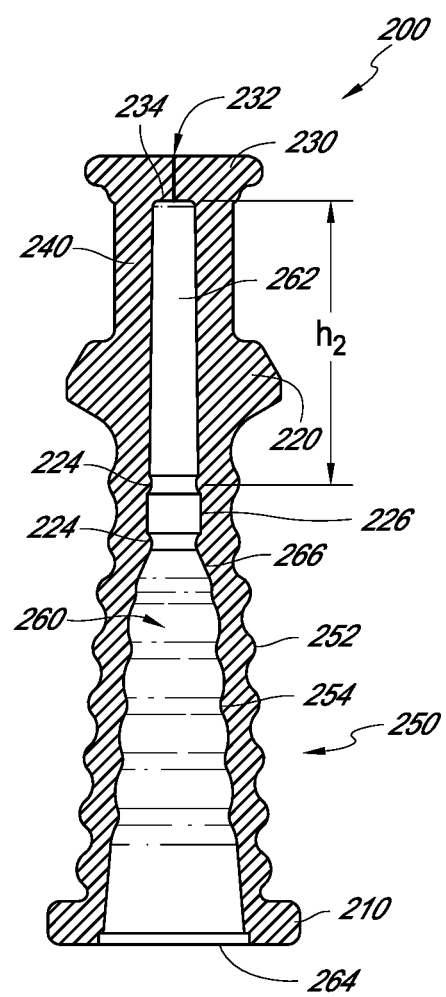
FIG. 11F is a cross-sectional view of the valve member of FIG. 11E.

In some embodiments, a valve member can have one or more sealing rings positioned to contact an internal projection member above or below a desired position on the internal projection member. For example, FIGS. 11E and 11F illustrate one embodiment of a valve member 200 that has two sealing rings, both sealing rings configured to contact the internal projection member at or below an opening in the internal projection member, as discussed further below. In some embodiments, a valve member may have sealing rings configured to contact an internal projection member at or above an opening in the internal projection member. In some embodiments, a valve member may have only a single sealing ring.

In some embodiments, the section of the valve member 200 above the uppermost sealing ring 224 can have generally flat interior walls, as illustrated. In some embodiments, the interior walls can be generally straight, and in some embodiments they can have a slight taper. For example, the illustrated embodiment has a 1 degree taper that narrows toward the top of the valve. In some embodiments, the taper can widen toward the top of the valve. In some embodiments, the taper can be greater than or equal to approximately 0.5 and/or less than or equal to approximately 1.5 degrees. In some embodiments, the taper can be greater than or equal to approximately 0 and/or less than or equal to approximately 4 degrees. In some embodiments, the taper can be greater than or equal to approximately 3 and/or less than or equal to approximately 7 degrees.

In some embodiments, the interior of the valve member 200 between adjacent sealing rings 224 can be wider than an interior width at a location above the top sealing ring. In some embodiments, the interior of the valve member between adjacent sealing rings can be wider than any interior width at a location above the top sealing ring.

FIGS. 11E and 11F also illustrate an embodiment of a valve member with a rectangular base profile. In some embodiments, the ratio of the width $w_1$ of the base to the thickness $t_1$ of the base can be greater than or equal to approximately 4 and/or less than or equal to approximately 8. In some embodiments, the ratio of $w_1$ to $t_1$ can be greater than or equal to approximately 5 and/or less than or equal to approximately 7. In some embodiments, the ratio of $w_1$ to $t_1$ can be greater than or equal to approximately 5.5 and/or less than or equal to approximately 6.5.

In some embodiments, the ratio of the total height of the valve $h_8$ to the thickness $t_1$ can be greater than or equal to approximately 15 and/or less than or equal to approximately 25. In some embodiments, the ratio of $h_8$ to $t_1$ can be greater than or equal to approximately 17 and/or less than or equal to approximately 22. In some embodiments, the ratio of $h_8$ to $t_1$ can be greater than or equal to approximately 18 and/or less than or equal to approximately 20. In some embodiments, the ratio of $h_8$ to $t_1$ can be greater than or equal to approximately 18.5 and/or less than or equal to approximately 19.5. The illustrated embodiment is shown in an assembled connector in FIGS. 18A and 18B.

Figure 11G:
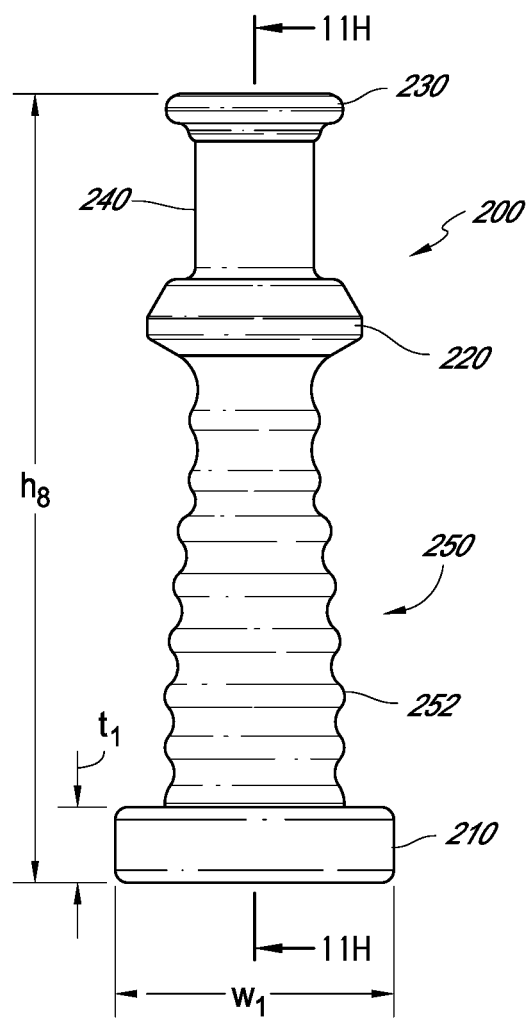
FIG. 11G is a front view of a valve member of a needleless connector.
Figure 11H:
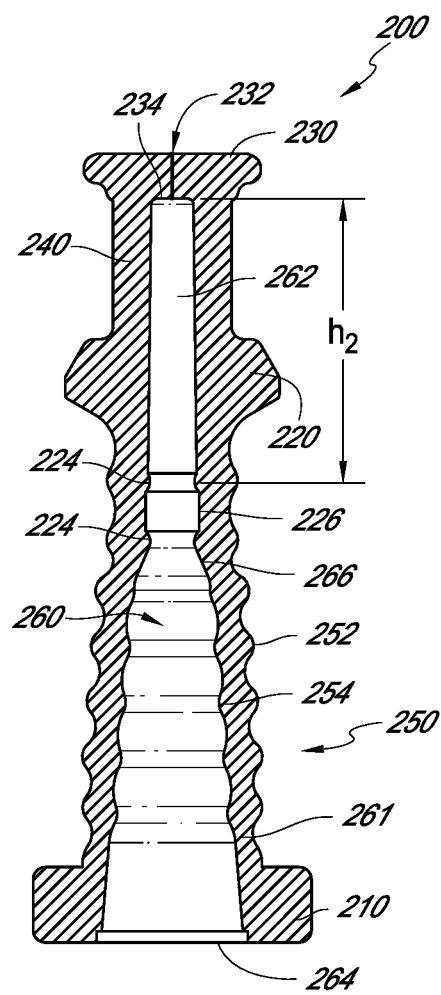
FIG. 11H is a cross-sectional view of the valve member of FIG. 11G.

In some embodiments, the thickness of the base 210 can be modified in order to provide support for automated manufacturing procedures. FIGS. 11G and 11H illustrate an embodiment of a valve member 200 with a thickened base 210. In some embodiments, the ratio of the width $w_1$ of the base to the thickness $t_1$ of the base can be greater than or equal to approximately 2 and/or less than or equal to approximately 5.5. In some embodiments, the ratio of $w_1$ to $t_1$ can be greater than or equal to approximately 2.5 and/or less than or equal to approximately 5. In some embodiments, the ratio of $w_1$ to $t_1$ can be greater than or equal to approximately 3 and/or less than or equal to approximately 4.5. In some embodiments, the ratio of $w_1$ to $t_1$ can be greater than or equal to approximately 3.5 and/or less than or equal to approximately 4.

In some embodiments, the ratio of the total height of the valve $h_8$ to the thickness $t_1$ can be greater than or equal to approximately 8 and/or less than or equal to approximately 13. In some embodiments, the ratio of $h_8$ to $t_1$ can be greater than or equal to approximately 9 and/or less than or equal to approximately 12. In some embodiments, the ratio of $h_8$ to $t_1$ can be greater than or equal to approximately 10 and/or less than or equal to approximately 11. In some embodiments, the ratio of $h_8$ to $t_1$ can be greater than or equal to approximately 10.5 and/or less than or equal to approximately 11.

In some embodiments, changing the thickness of the base can affect the compressibility of the valve member. For example, increasing the thickness of the base can limit the ability of the valve member as a whole to compress when a medical implement is used to access a needleless connector with the valve member. In some embodiments, the ribbed section 250 can be modified to account for any changes in the base and allow the valve member to compress a desired amount when a medical implement is used to access a needleless connector with the valve member. For example, in some embodiments the section 261 of the valve member wall adjacent the base 210 can be thinner than other sections of the valve member wall and/or thinner than previous embodiments. In some embodiments, the section 261 of the valve member wall can be thinner than any other section of the valve member wall. In some embodiments, the section 261 of the valve member wall can be thinner than any other section of the valve member wall below a first sealing ring 224. In some embodiments, the section 261 of the valve member wall can be thinner than any other section of the valve member wall below a shoulder 220. The section 261 can help allow the valve member to compress more than it otherwise would when a medical implement accesses the needleless connector. The thickness of the wall and the amount of wall with a thinner section can be configured to allow the valve member to compress a desired amount, as discussed further below. The illustrated embodiment is illustrated in an assembled connector in FIGS. 19A and 19B.

Figure 11I:
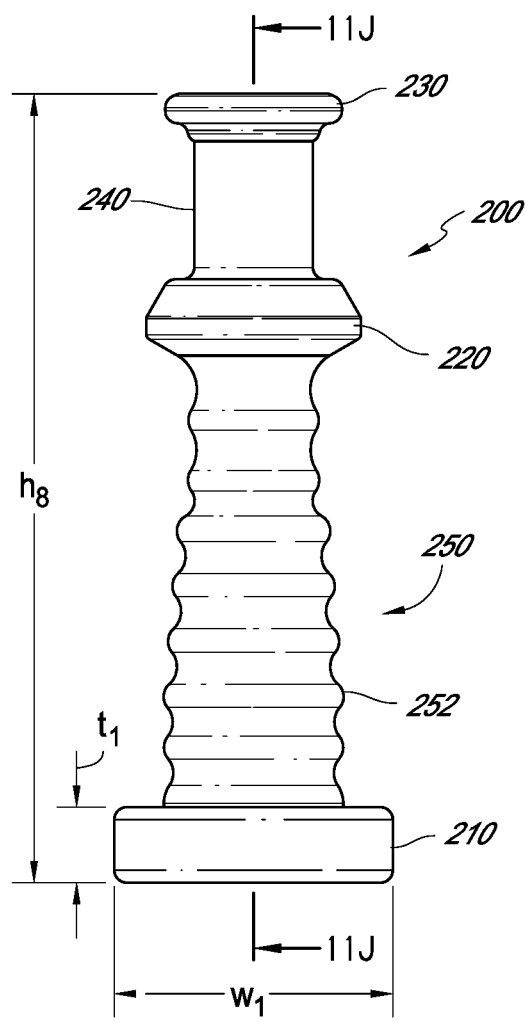
FIG. 11I is a front view of a valve member of a needleless connector.
Figure 11J:
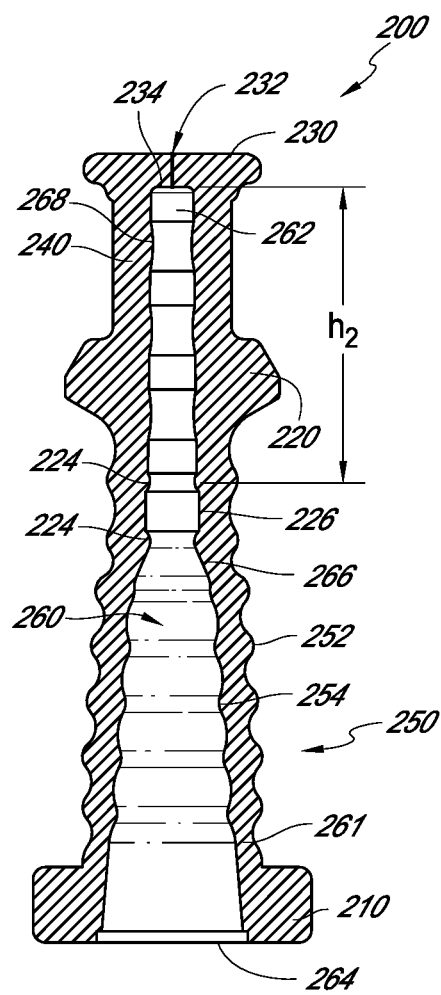
FIG. 11J is a cross-sectional view of the valve member of FIG. 11I.

In some embodiments, the interior surface 266 of a valve member 200 can have surface roughenings 268, such as scalloped, curved, uneven, wrinkled, or irregular sections instead of or in addition to the ribbed sections 250. For example, FIGS. 11I and 11J illustrate an embodiment of a valve member 200 where the section of the interior surface 266 above the uppermost sealing ring 224 has roughenings 268 in the form of a scalloped surface having slight curves. This can help decrease friction between the valve member and an internal projection when a medical implement is used to access a needleless connector with the valve member, as discussed further below. The illustrated embodiment is shown in an assembled connector in FIGS. 20A and 20B.

Figure 11K:
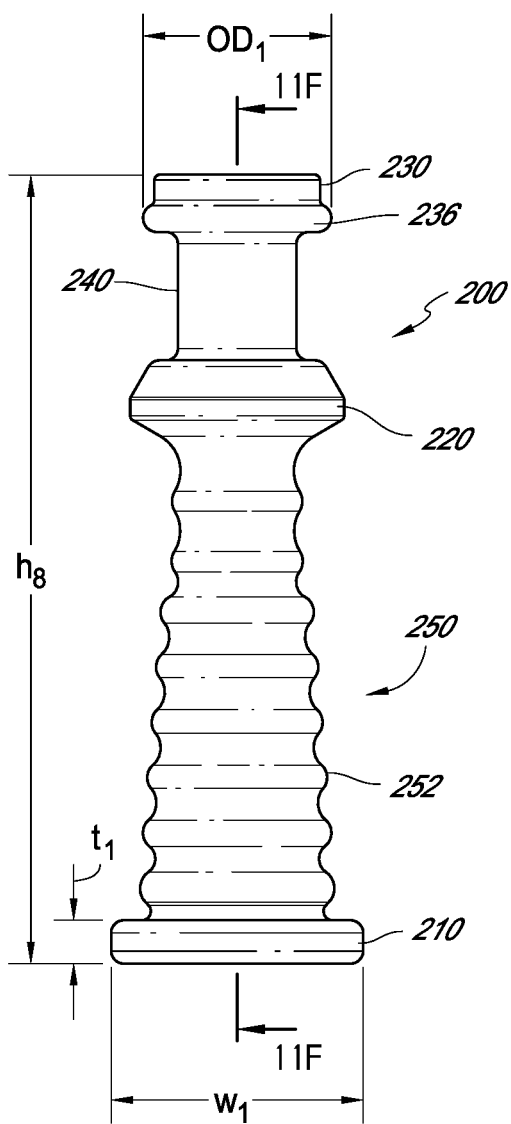
FIG. 11K is a front view of a valve member of a needleless connector.
Figure 11L:
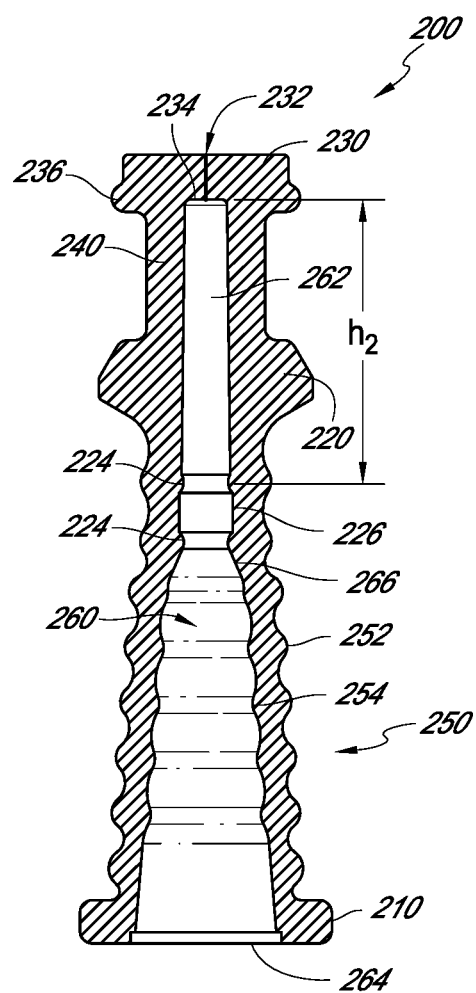
FIG. 11L is a cross-sectional view of the valve member of FIG. 11K.
Figure 11M:
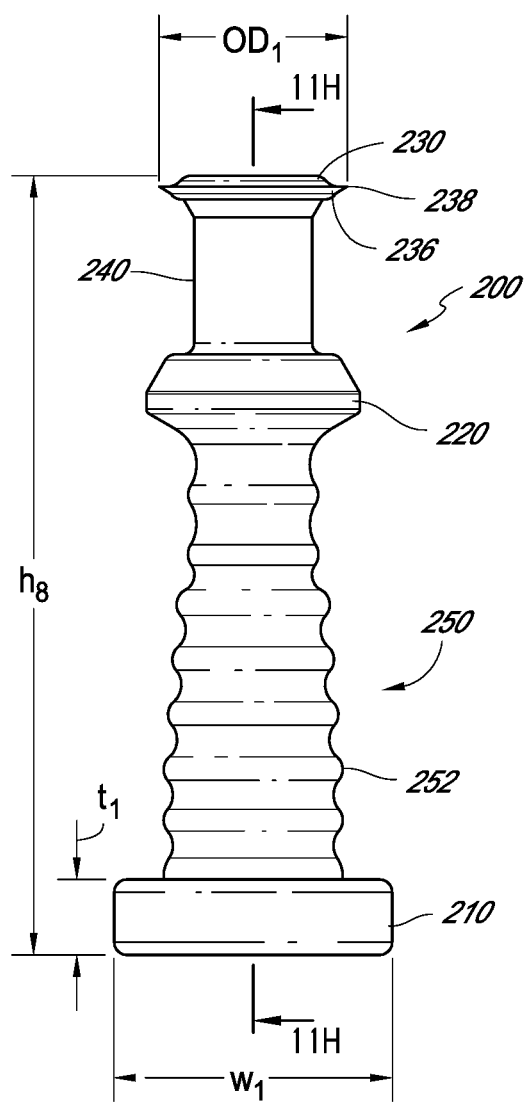
FIG. 11M is a front view of a valve member of a needleless connector.
Figure 11N:
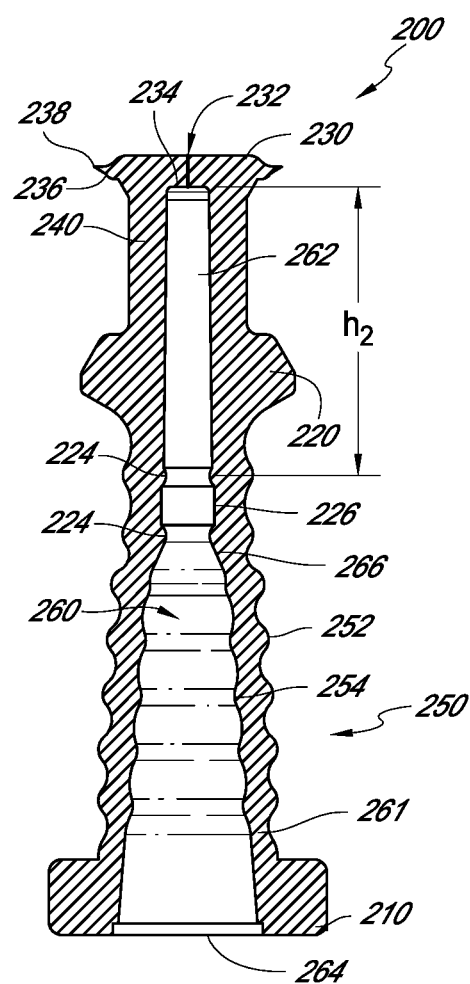
FIG. 11N is a cross-sectional view of the valve member of FIG. 11M.

In some embodiments, a valve member 200 can have an external annular projection, seal, or wiper 236 extending externally from the valve at or above the neck 240. As described further below with respect to FIGS. 21A through 22D, the seal can help prevent blood from collecting within the body of the needleless connector or between the valve member and the body of the needleless connector. Accordingly, the seal can be configured to remove fluid from the connector even if the fluid is outside the intended fluid path. FIGS. 11K and 11L illustrate one embodiment of a valve member with such a seal 236. As illustrated, the seal 236 can generally have the shape of an annular ring. In some embodiments, the seal can have a variety of other shapes. For example, FIGS. 11M and 11N illustrate one embodiment of a valve member 200 with an external seal 236 that has an upper side and a lower side that join to form a tip 238. In some embodiments, one of the upper side and lower side can be generally horizontal. In some embodiments, one or both of the upper side and lower side can be generally flat. In some embodiments, one or both of the upper side and lower side can be generally curved, have multiple curves, or have other shapes and configurations.

In some embodiments, the seal 236 can have an outer diameter $OD_1$. This is described in more detail below. In some embodiments, the seal 236 can be positioned a distance below the top of the valve member, although in some embodiments it can be flush with the top. Preferably, the external seal 236 is close enough to the top of the valve member to allow for the seal and top to be sterilized when the valve member is in a closed position by swabbing the top of the valve member. The seal illustrated in FIGS. 11M and 11N includes an upper profile with a raised inner portion and a curved annular transition toward the tip 238. Such curvature can facilitate sterilization, such as by alcohol swab, by reducing abrupt transitions and can minimize displacement of the upper profile in the lateral direction during swabbing by reducing friction between the seal and the swab.

The interior surface 266 of embodiments of valve members with external seals 236 can be configured according to any of the various embodiments described herein. As illustrated, the interior surface in the upper interior section 262 of the valve members of FIGS. 11K-11N is similar to that shown and described with respect to FIGS. 11E and 11F, but other described configurations can be used.

Figure 11O:
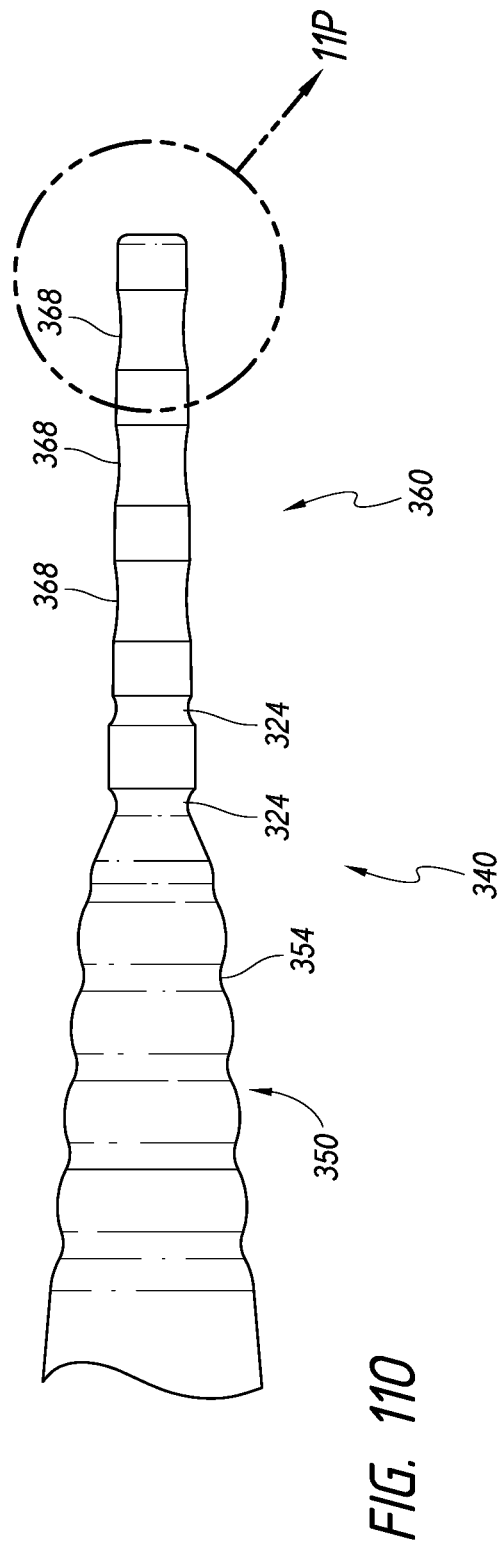
FIG. 11O is a side view of a core pin used to manufacture a valve member.
Figure 11P:
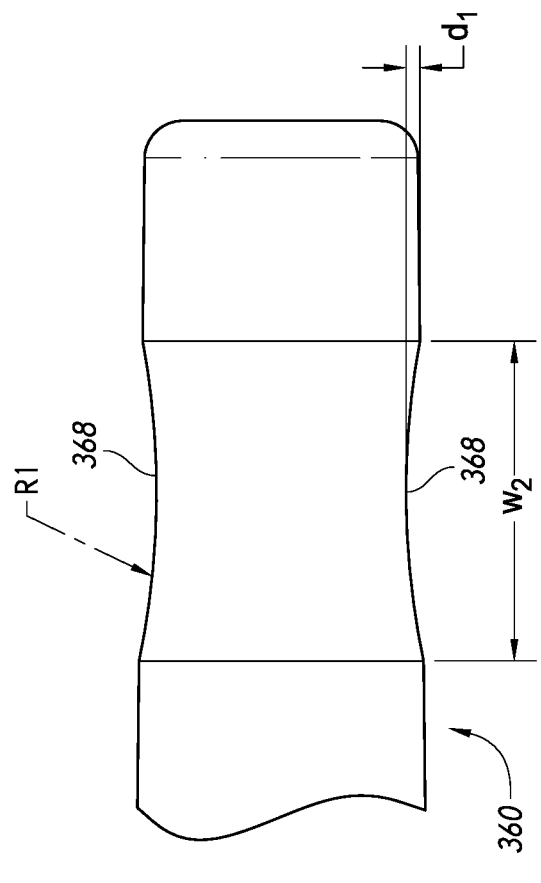
FIG. 11P is a side view of a tip of the core pin of FIG. 11O.

In some embodiments, the valve member 200 can be injection molded. FIGS. 11O and 11P illustrate one embodiment of a core pin 340 that can be used as part of an injection molding process to form the valve member. FIG. 11O illustrates the core pin and FIG. 11P illustrates a section of the core pin identified in FIG. 11O. The core pin can include a lower (or proximal) section 350, which in some embodiments can include indents 354 that can form inner ribs of the valve member. The core pin can also include an upper (or distal) section 360, which can be configured to correspond to a profile of any valve member discussed above. For example, in some embodiments, the upper section 360 can have one or more grooves 324 that can define sealing rings 224 of a valve member. The upper section can also include cutouts or indents 368 that can define roughenings 268, such as scalloped sections. The indents 354, 368 preferably extend circumferentially around the core pin, although in some embodiments they may extend only partially around. In some embodiments, the upper section 360 can be generally flat or smooth above the grooves 324.

As illustrated in FIG. 11P, the indents 368 can have a depth $d_1$ and a width $w_2$. In some embodiments the width and depth can be the same for all indents 368, and in some embodiments one or both of the width and depth can vary among indents. In some embodiments, the ratio of the width $w_2$ to the depth $d_1$ can be greater than or equal to approximately 5 and/or less than or equal to approximately 30. In some embodiments, the ratio of the width $w_2$ to the depth $d_1$ can be greater than or equal to approximately 10 and/or less than or equal to approximately 30. In some embodiments, the ratio of the width $w_2$ to the depth $d_1$ can be greater than or equal to approximately 15 and/or less than or equal to approximately 25. In some embodiments, the ratio of the width $w_2$ to the depth $d_1$ can be greater than or equal to approximately 18 and/or less than or equal to approximately 22. In some embodiments, the ratio of the width $w_2$ to the depth $d_1$ can be approximately 20.

In some embodiments, the indents 368 can have a cross-section that forms an arc of a circle having radius $R_1$, as illustrated. In some embodiments, the radius $R_1$ can be greater than or equal to approximately 0.05 inches and/or less than or equal to approximately 0.2 inches. In some embodiments, the radius $R_1$ can be greater than or equal to approximately 0.08 inches and/or less than or equal to approximately 0.16 inches. In some embodiments, the radius $R_1$ can be greater than or equal to approximately 0.1 inches and/or less than or equal to approximately 0.14 inches. In some embodiments, the radius $R_1$ can be approximately equal to 0.125 inches. In some embodiments, the scallops can have cross-sections with non-circular profiles.

The indents 368 naturally form valve members that have varying inner diameters at the surface roughenings 268. In some embodiments, the ratio of the maximum inner diameter to the minimum inner diameter of the valve member at the surface roughenings can be between 1 and approximately 1.05. In some embodiments, the ratio can be between 1 and approximately 1.10. In some embodiments, the ratio can be between 1 and approximately 1.15. In some embodiments, the ratio can be between 1 and approximately 1.20. In some embodiments, the ratio can be between 1 and approximately 1.25. In some embodiments, the ratio can be between 1 and approximately 1.30. It is understood that for each embodiment of the core pin 340, a corresponding embodiment of a valve member molded on the core pin exists.

Figure 12:
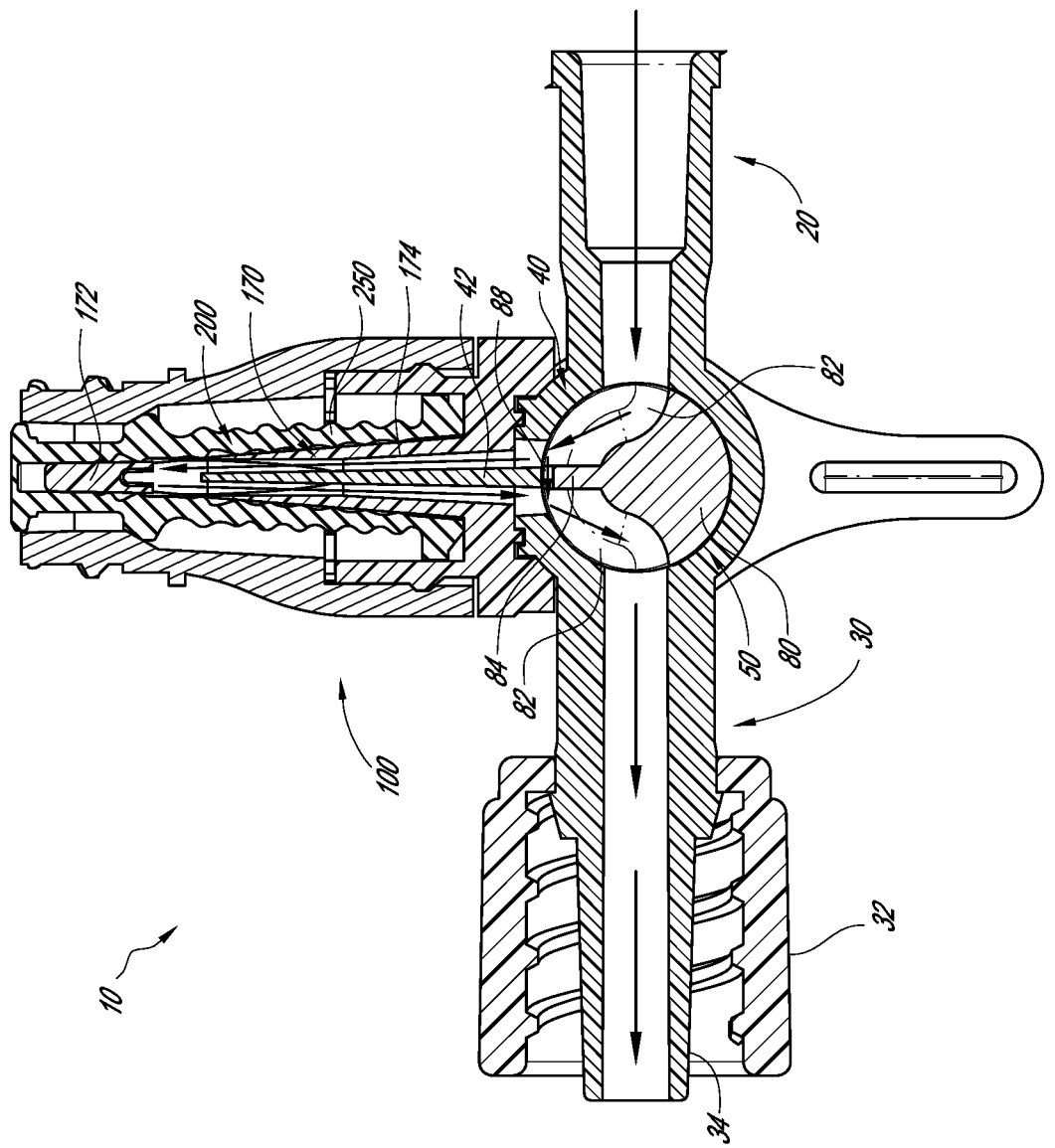
FIG. 12 is a cross-sectional view of a stopcock with a needleless connector attached to one port.

FIG. 12 illustrates a cross-sectional view of a stopcock assembly 10 with an assembled needleless connector 100 positioned over a port that has a fluid diverter 42. The needleless connector can surround the fluid diverter, which can extend into the needleless connector. The stopcock is illustrated with the fluid directing section 80 in a first position, such that the first port 20, the second port 30, and the third port 40 are all in fluid communication with each other. Schematic arrows represent fluid flow paths as the fluid flows from the first port to the second port. In some embodiments, fluid can flow in other directions, such as from the second port to the first port.

As fluid flows, the channel recesses 82 can guide the flow from the first port 20 toward the third port 40. In some embodiments, some of the fluid will flow through the gap 88 between the fluid flow guide 84 and the fluid diverter 42, such that a first portion of the fluid does not enter the third port 40 but instead flows directly from the first port through the recesses 82 and into the second port 30. A second portion of fluid, however, will pass into the third port 40. At least part of this second portion can be forced by the fluid diverter 42 to flow up into the needleless connector 100, over the top of the fluid diverter, and then back down the other side, through a recess 82 and into the second port 30. Thus, the second portion of fluid can help flush out the needleless connector at a distal end thereof. As described in more detail with respect to FIG. 16A, in various embodiments the fluid diverter can direct at least part of the second portion of fluid into different positions within the needleless connector.

The components of the stopcock 10 and/or needleless connector 100, such as the ports 20, 30, 40, the connecting portion 50, the fluid director 80, the fluid diverter 42, the valve member 200, the base member 160, and the body 120, can be formed of a variety of materials depending on desired functionality. For example, in some embodiments it may desirable to have components of the needleless connector to be formed of materials that allow for an operator to see the fluid flow path through the needleless connector to verify that blood or other fluid has been flushed out, or that blood has not been trapped in parts of the connector that may not flush, such as between the valve member 200 and the internal projection member 170. In some embodiments, one or more of the components of the needleless connector can be made from a translucent, transparent, and/or clear material.

Additionally, in some embodiments the components of the needleless connector, such as the valve member 200, the base member 160, and the body 120, can include elements configured or adapted to kill pathogens. For example, in some embodiments one or more of the components of the needleless connector can include antimicrobial agents. In some embodiments, the antimicrobial agents can be a coating on the components of the needleless connector or can be incorporated into the structure of the components of the needleless connector, from where they can leach out, such as from the silicone matrix of the valve member.

FIGS. 13 and 14 illustrate cross-sectional views of a medical connector 100, attached to a stopcock with a fluid diverter 42, as the medical connector receives a medical implement 300 that contains a fluid. The medical implement can be used to inject a fluid into a flow passing through the stopcock, to withdraw fluid, or to perform other procedures. FIG. 13 illustrates the medical connector as the medical implement approaches, with the valve member 200 in a closed position, and FIG. 14 illustrates the medical implement once it has been inserted and moved the valve member into an open position.

Generally, the tip 310 of the medical implement can be inserted into the upper portion 128 of the body 120 of the medical connector. As the tip enters the upper portion, it will push the valve member 200, compressing it into the body of the medical connector. Various features of the valve member, such as the ribs in the ribbed section 250, can help allow the valve member to compress. In the illustrated embodiment, the medical implement 300 includes a syringe with a luer tip. In some embodiments, the medical implement can have a luer lock connector adapted to interface with the threads 130 of the needle connector body 120. An outer shoulder or collar 132 can help block devices with connections such as luer connections from being inserted too far into the needleless connector.

As the valve member 200 is pushed into the body 120 of the needleless connector, the projection tip 172 can contact the slit 232 in the top 230 of the valve member. As the valve member is compressed further, the tip can pass through the slit, opening it and allowing the valve member to slide down over the projection tip and/or projection body 174. The tip 310 of the medical implement 300 can be pressed against the top 230 of the valve member, preferably creating a seal such that fluid in the medical implement does not flow past the top of the valve member outside of the valve member. In some instances, the seal between the tip 310 and the top 230 of the valve member may not always be perfect or may break before the medical implement is completely withdrawn. For example, in some cases manufacturing tolerances may be such that the tip 310 can be withdrawn from the connector at an angle. If a care provider does so, it could break the seal and allow blood or other fluids to flow onto the top of the valve member. Additionally, a care provider will typically swab the top of the valve with a disinfecting agent before inserting the medical implement 300. Thus, the top of the valve can sometimes be wet when a tip is inserted, which can create a weaker seal. Additionally, if the top of the valve is wet with a substance that can thin blood, such as alcohol, it can be easier for blood to pass through any seal between the top of the valve and the tip 310 of a medical implement. As described with respect to FIGS. 11K through 11N, various embodiments of a valve member 200 can include exterior sealing rings that can help prevent any blood on the top of the valve member from flowing past the top to get between the valve member and the body of the connector. In addition, such features can act on the walls of the inner cavity of the connector to move any leaked fluid (e.g., fluid that is outside of the intended flow path of the medical implement and the projection member) out of the connector as the seal transitions to the first, closed position.

As the tip of the medical implement continues to push the valve member down, illustrated in FIG. 14, the top of the valve member and the open slit will reach the top 184 of an opening 180. As the valve member passes this point, fluid can begin to flow through the opening between the medical implement and the interior 280 of the projection. Preferably, the medical implement can be inserted far enough such that the top surface of the top 230 of the valve member is at or below the bottom 182 of the opening. This can help maximize the flow rate between the medical implement and the needleless connector.

In some embodiments, the needleless connector can be configured to function without an internal projection member, and the fluid diverter can extend directly into the interior of the valve member. Rather than compressing a valve member until an internal projection member penetrates the slit, a tip of a medical implement can pass through a slit in the valve member itself, allowing fluid to flow through the valve member and out of the needleless connector. In some embodiments, the tip can pass through the valve member without pushing the valve member into the needleless connector. In some embodiments, the tip can extend around a portion of the fluid diverter when the medical implement is inserted into the valve member. Some examples of embodiments where a needleless connector does not have an internal projection member are illustrated and described below.

In some embodiments, the valve member 200 can be configured to compress uniformly as a tip of a medical implement is inserted into the body of a medical connector. In some embodiments, the valve member can be configured to compress non-uniformly. For example, in some embodiments an upper or distal region of the valve member, such as the neck 240, can begin to compress before a lower or proximal region, such as the ribbed section 250 or any region below the shoulder 220, can begin to compress. In some embodiments, the upper region can fully compress before the lower region fully compresses. In some embodiments, the upper region can fully compress before the lower region begins to compress. When a medical implement is removed, the upper and lower regions can expand non-uniformly in opposite sequence. Thus, in some embodiments a lower region can begin to expand before an upper region begins to expand, or a lower region can fully expand before an upper region fully expands. This can provide various sealing benefits, discussed further below.

In some embodiments, the valve member can be configured to compress non-uniformly such that an upper or distal region of the valve member 200, such as the neck 240, can begin to compress after a lower or proximal region, such as the ribbed section 250 or any region below the shoulder 220, can begin to compress. In some embodiments, the lower region can fully compress before the upper region fully compresses. In some embodiments, the lower region can fully compress before the upper region begins to compress. When a medical implement is removed, the upper and lower regions can expand non-uniformly in opposite sequence. Thus, in some embodiments an upper region can begin to expand before a lower region begins to expand, or an upper region can fully expand before a lower region fully expands.

In some embodiments, the valve member 200 can be configured such that an upper or distal region of the valve member, such as the neck 240, does not appreciably compress as a tip of a medical implement is inserted into the body of a medical connector. The valve can compress substantially within a lower or proximal region. This can also provide various sealing benefits, discussed further below.

In some embodiments, the needleless connector may have a valve member where a top of the valve member defines a continuous opening rather than a slit. In such embodiments, an interior projection can extend into or through the continuous opening. A medical implement can be used to compress the valve member and expose openings in the interior projection to fluid within the medical implement. Further details of these and other embodiments can be found in PCT Application No. PCT/US2012/054289, filed Sep. 7, 2012, which is hereby incorporated by reference herein in its entirety and a copy of which is enclosed and is included as part of this specification.

The flow rate from the medical implement 300 into the needleless connector can be limited by the smallest area through which fluid must pass. Preferably, this limiting area is defined by the cross sectional area of the interior 280 of the projection at the bottom of the openings 180, rather than by the openings themselves. In such embodiments, maximum flow rate can be achieved when the valve member 200 has been pushed down to a point where the total area of openings 180 exposed to fluid in the medical implement is equal to the cross sectional area of the interior 280 of the projection at the bottom of the openings. As described, the cross sectional area of the interior of the projection accounts for any portion of the fluid diverter that occupies space within the interior of the projection. In some embodiments, the openings can be sized such that this maximum flow rate can be achieved when the top surface 230 of the valve member is generally level with the bottom edge 182 of the openings. In some embodiments, the valve member can be configured to be easily compressible to this position but not past it, such as by modifying the thickness or ribbing on the valve member walls as discussed above. In some embodiments, maximum flow rate can be achieved when the top surface of the valve member has not yet reached the bottom edge of the openings. In some embodiments, the valve member can be configured to be easily compressible to this position but not past it.

Figure 15A:
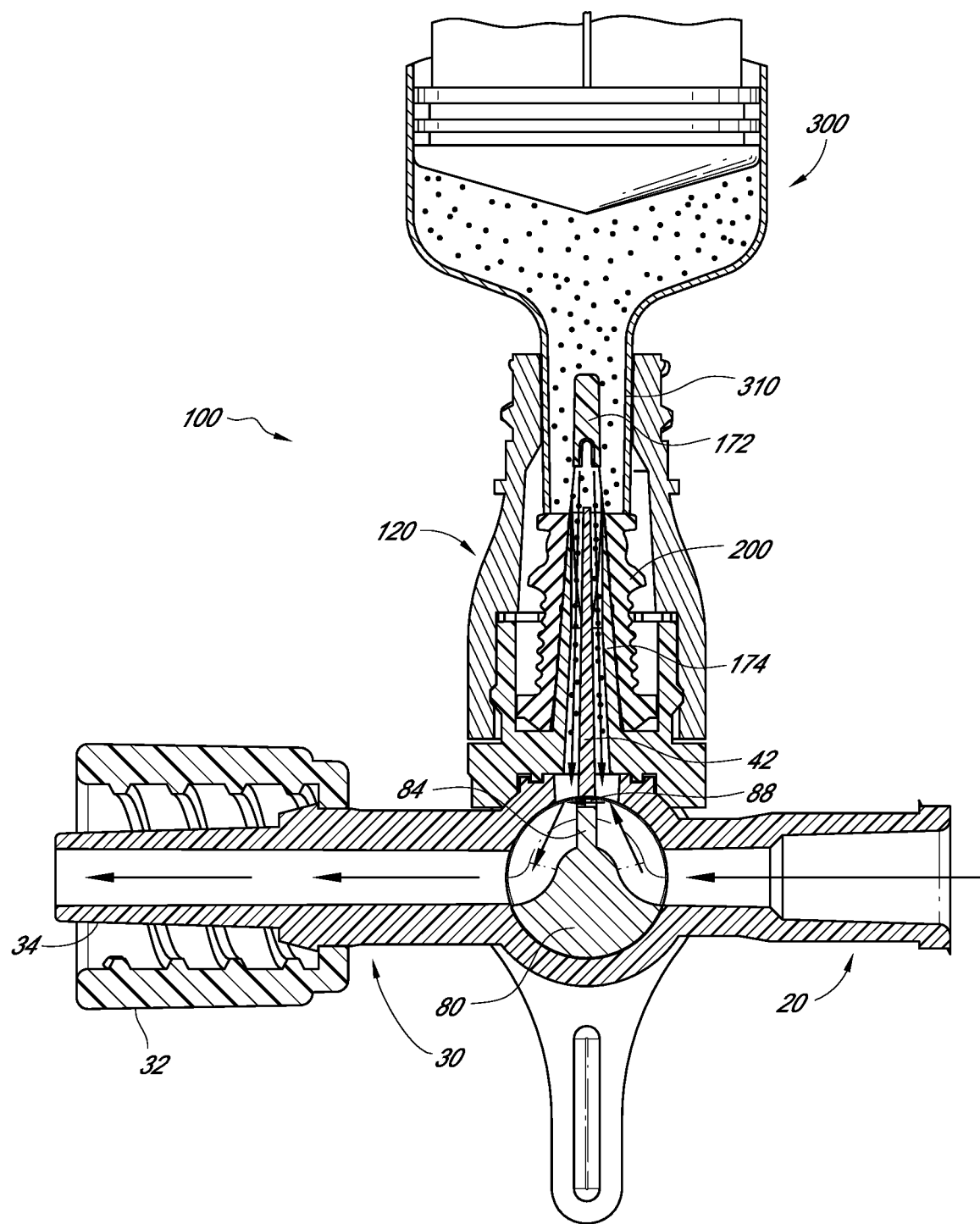
FIG. 15A is a schematic view of flow paths on a cross-section of a medical implement inserted into a needleless connector on a stopcock to inject fluid into the connector.

FIG. 15A illustrates one embodiment of fluid flow paths that can exist when a medical implement 300 has been inserted into the needleless connector 100 to inject fluid into the connector. When fluid is flowing through the stopcock from the first port 20 to the second port 30, fluid from the medical implement can join this fluid flow. In some embodiments, fluid from the medical implement can flow toward the fluid directing section 80 on either side of the fluid diverter 42, and fluid that is on the side of the first port can pass through the gap 88 between the fluid flow guide 84 and the fluid diverter 42. In some embodiments, if the pressure of fluid flowing from the first port into the fluid directing section 80 is sufficiently great, fluid can instead follow a path similar to that illustrated in FIG. 12, with fluid flowing up one side of the fluid diverter, over the top, and then back down the opposite side. In such cases, fluid from the medical implement can flow down the opposite side with fluid flowing in from the first port.

Figure 15B:
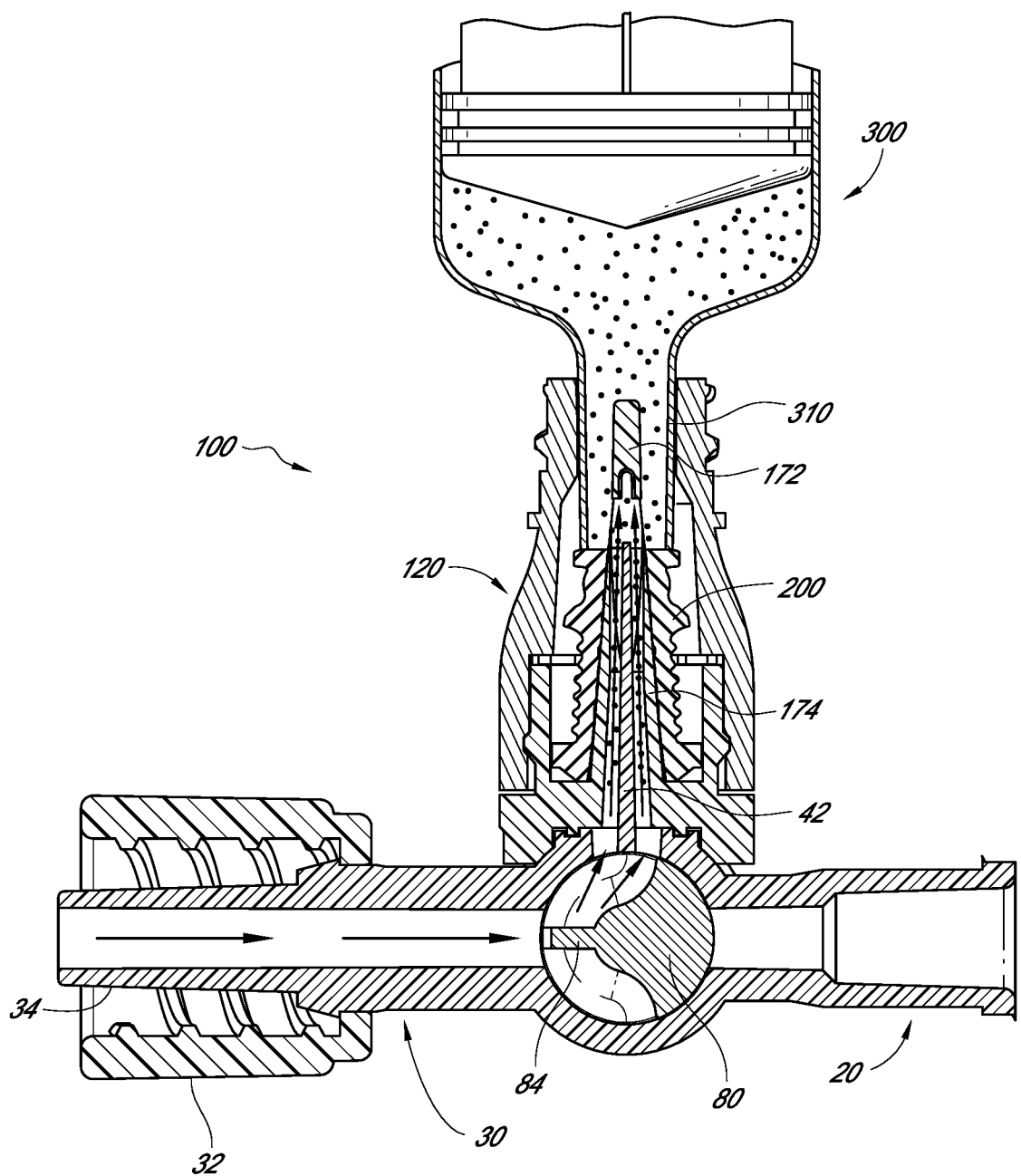
FIG. 15B is a schematic view of flow paths on a cross-section of a medical implement inserted into a needleless connector on a stopcock to withdraw fluid through the connector.

A medical implement can also be used to withdraw fluid from the fluid flow path through the connector 100. FIG. 15B illustrates one embodiment of fluid flow paths that can exist when a medical implement 300 has been inserted into the needleless connector 100 to withdraw fluid from the connector. Generally, fluid will be drawn from a source connected to one of the first port 20 and the second port 30, and the fluid directing section 80 can be positioned such that the other of the first port and the second port is blocked. FIG. 15B illustrates an embodiment in which the fluid directing section blocks the first port 20 and fluid is drawn from the second port 30, through the needleless connector 100, and into the medical implement 300. Fluid can flow through the connector on both sides of the diverter 42. In some embodiments, fluid can be withdrawn from the fluid flow path through the connector when the fluid directing section 80 is in the first position, as it is in FIG. 15A.

Figure 16A:
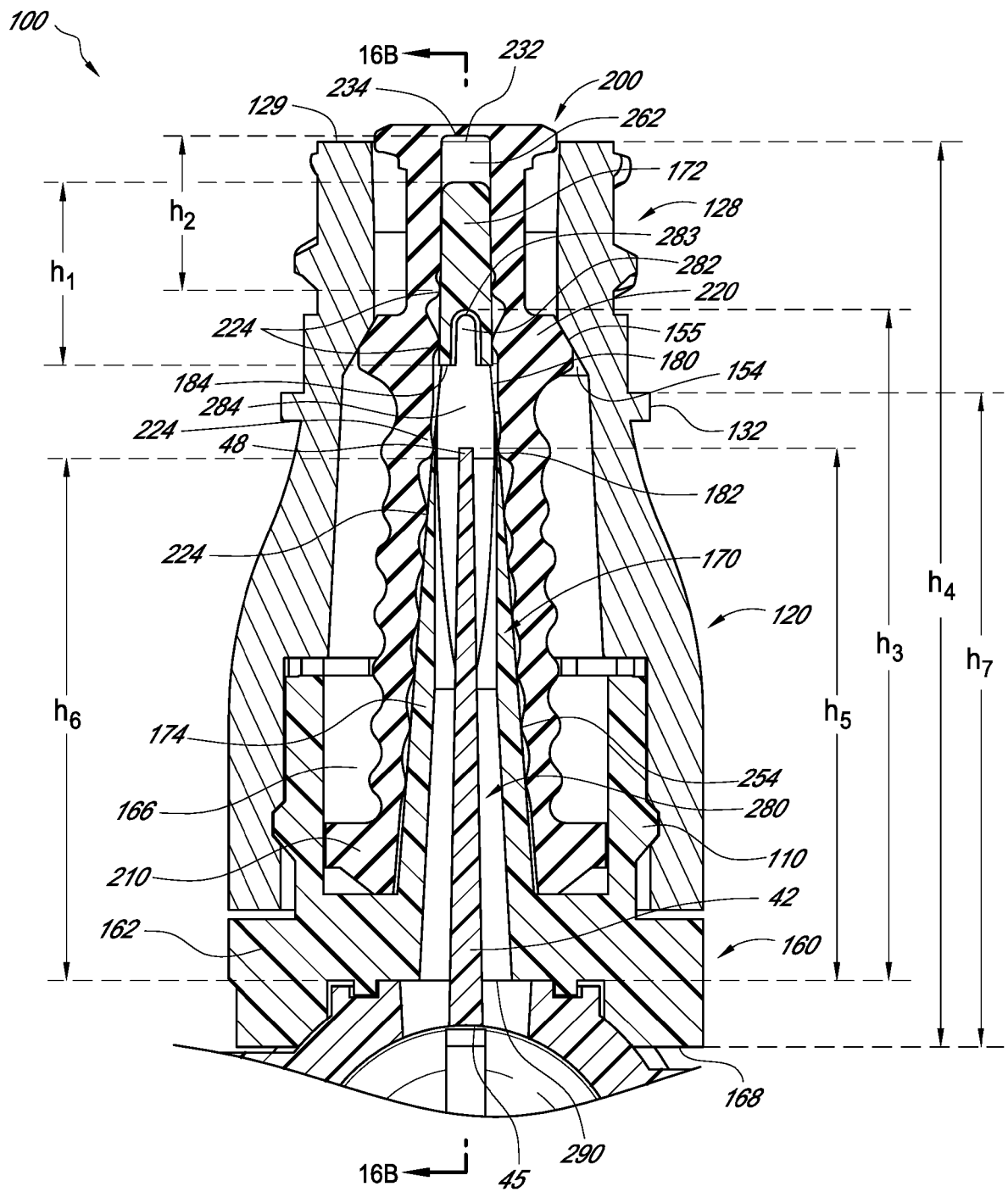
FIG. 16A is a cross-sectional view of a needleless connector positioned on a port of a stopcock.
Figure 16B:
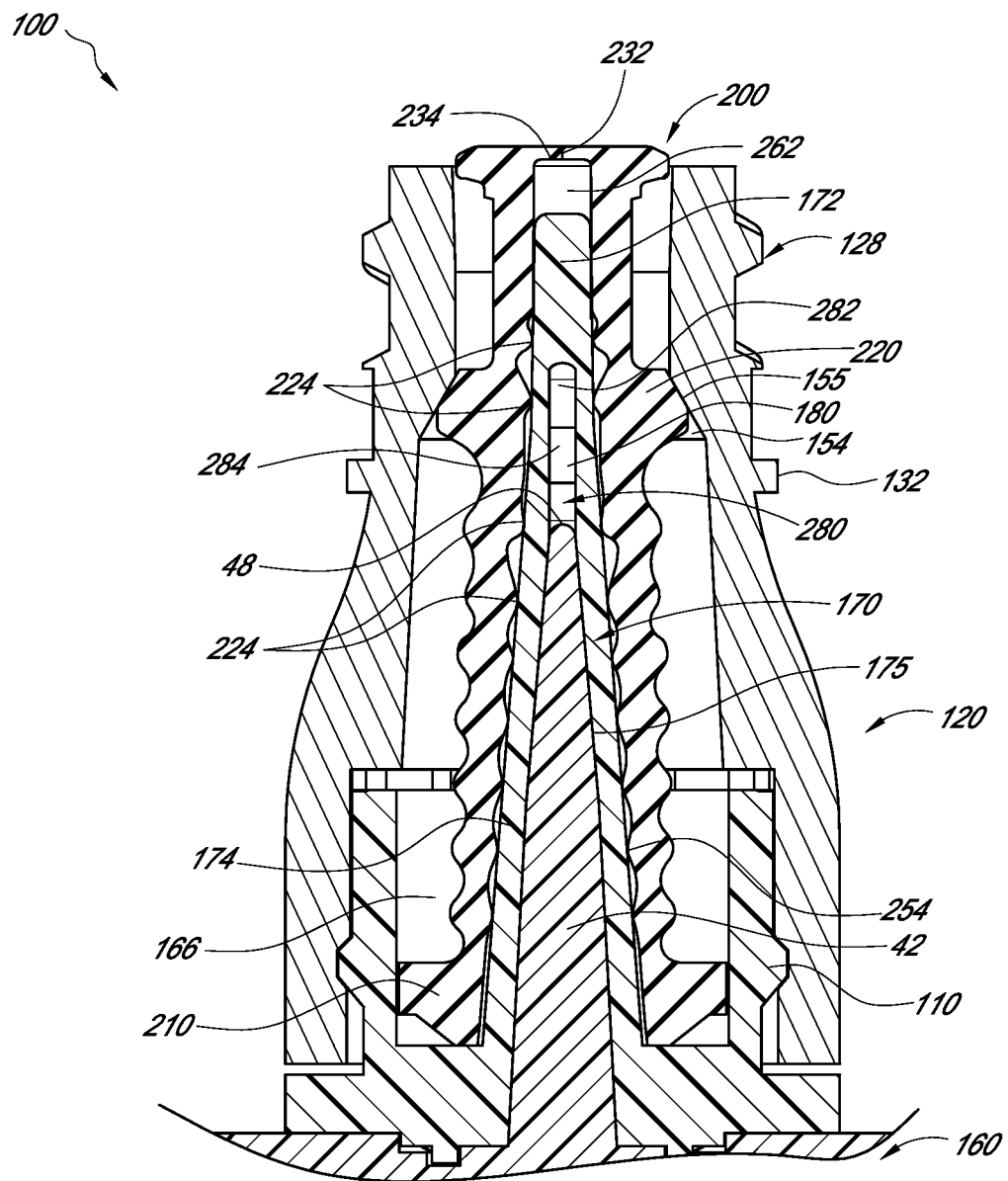
FIG. 16B is a cross-sectional view of the needleless connector of FIG. 16A, taken along the line 16B-16B of FIG. 16.
Figure 17A:
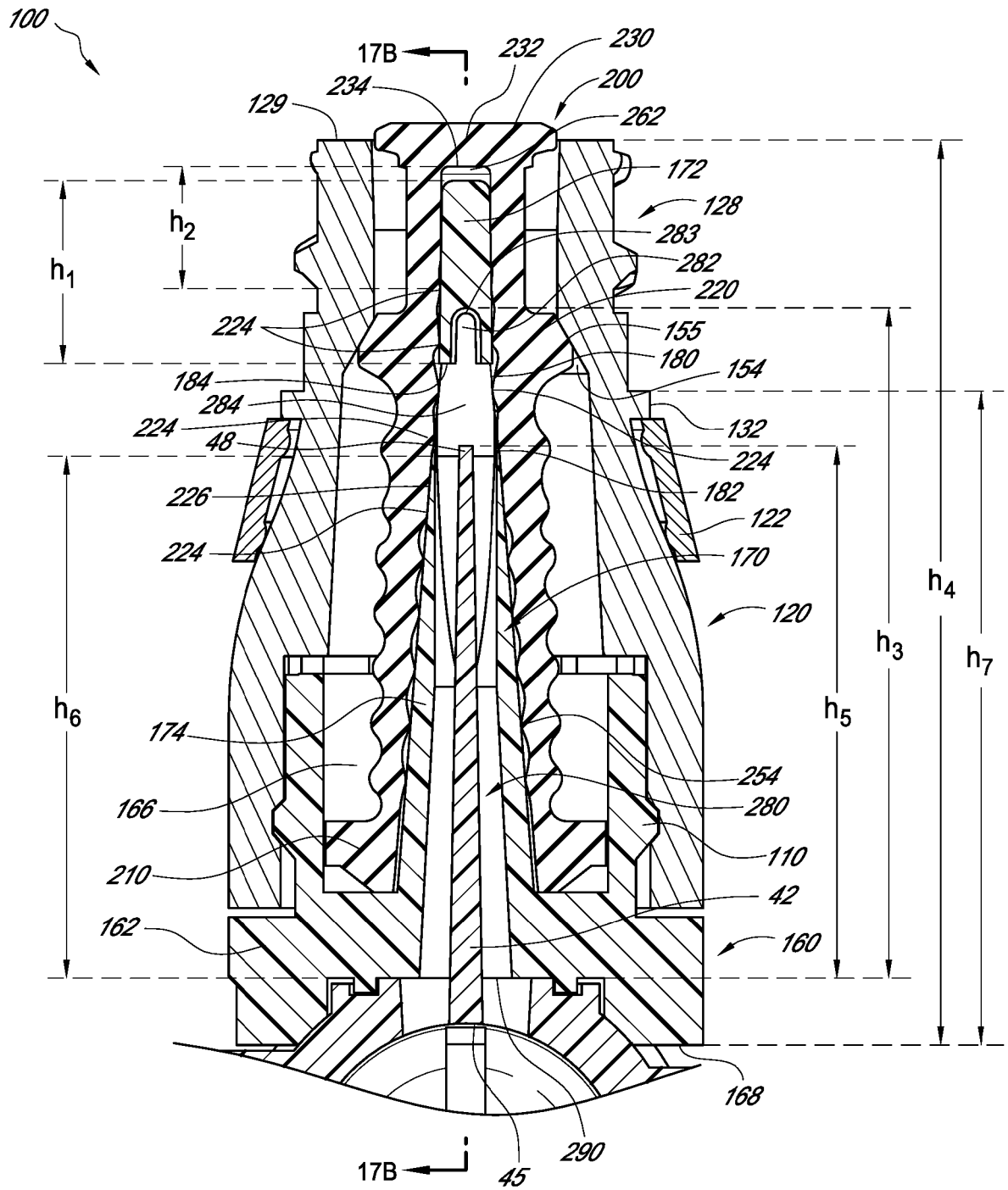
FIG. 17A is a cross-sectional view of a needleless connector positioned on a port of a stopcock.
Figure 17B:
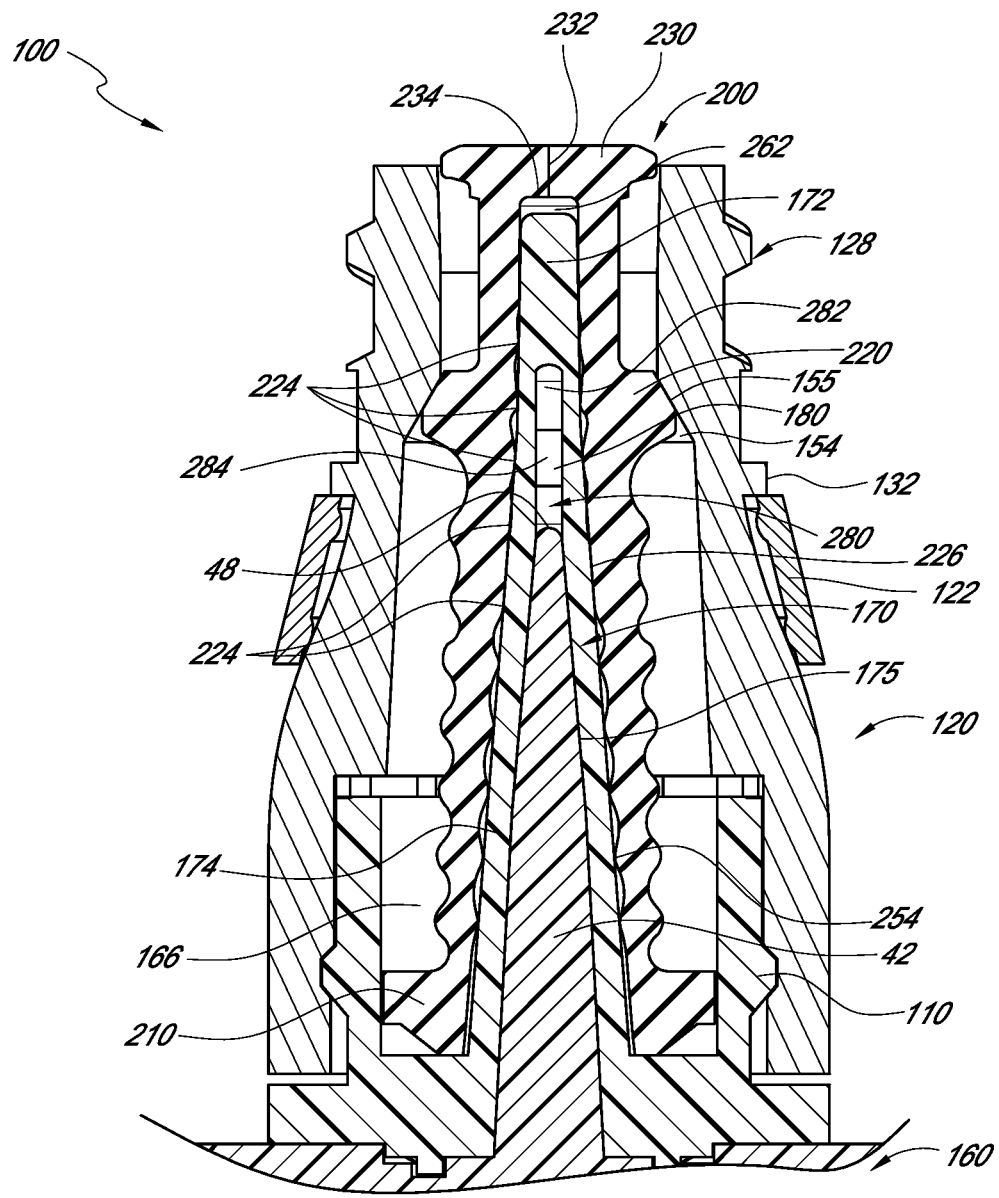
FIG. 17B is a cross-sectional view of the needleless connector of FIG. 17A, taken along the line 17B-17B of FIG. 17A.
Figure 18A:
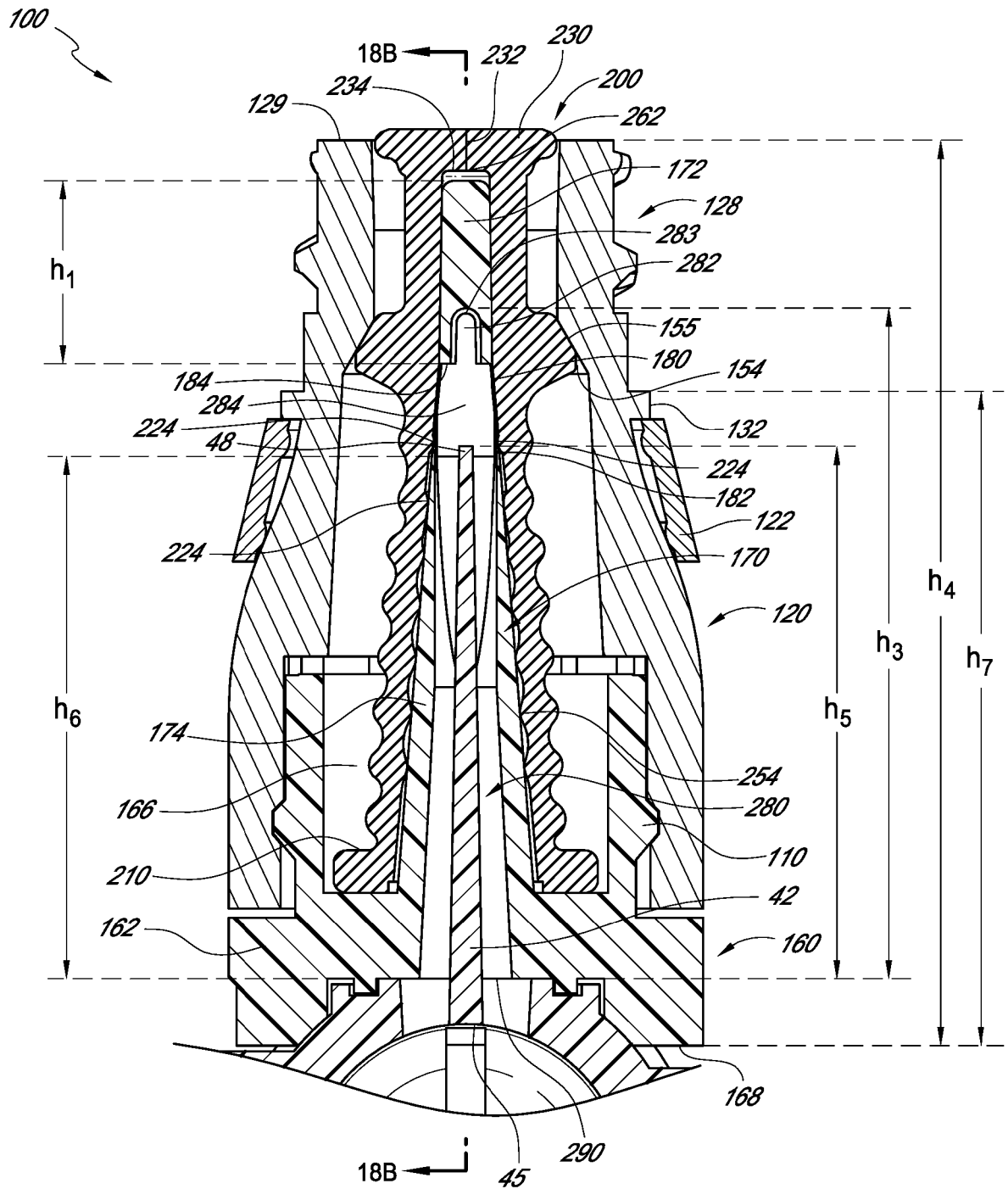
FIG. 18A is a cross-sectional view of a needleless connector positioned on a port of a stopcock.
Figure 18B:
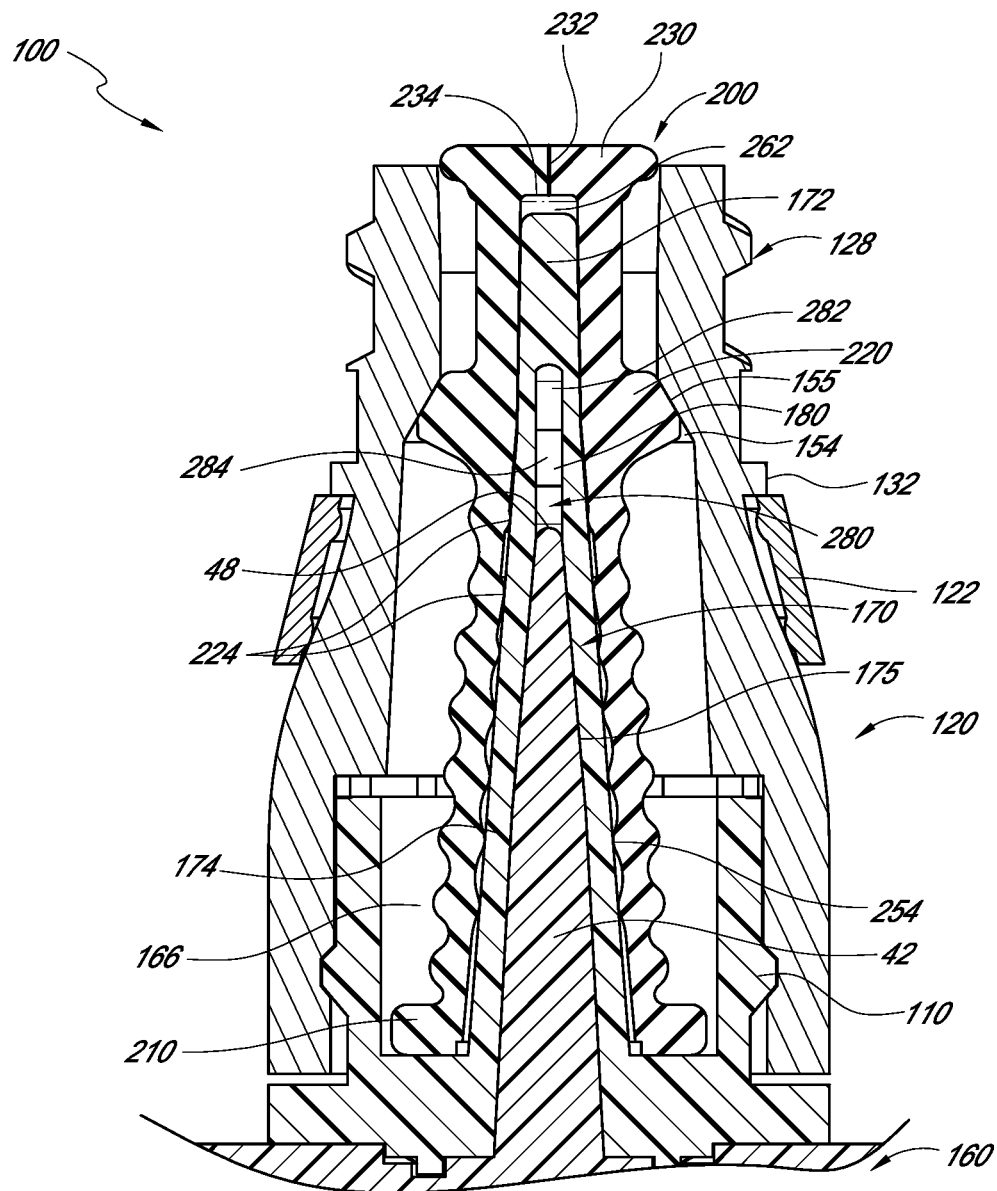
FIG. 18B is a cross-sectional view of the needleless connector of FIG. 18A, taken along the line 18B-18B of FIG. 18A.
Figure 19A:
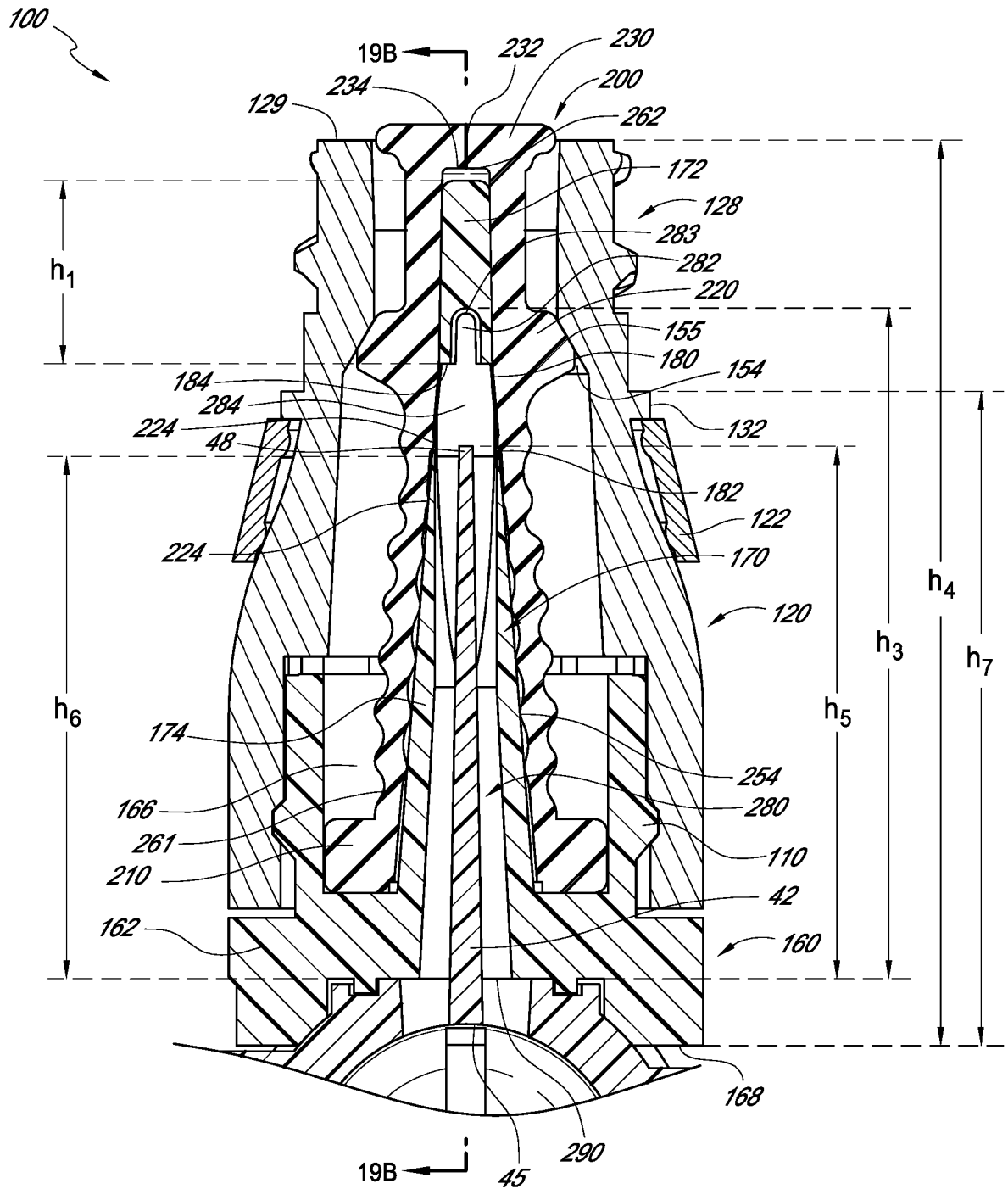
FIG. 19A is a cross-sectional view of a needleless connector positioned on a port of a stopcock.
Figure 19B:
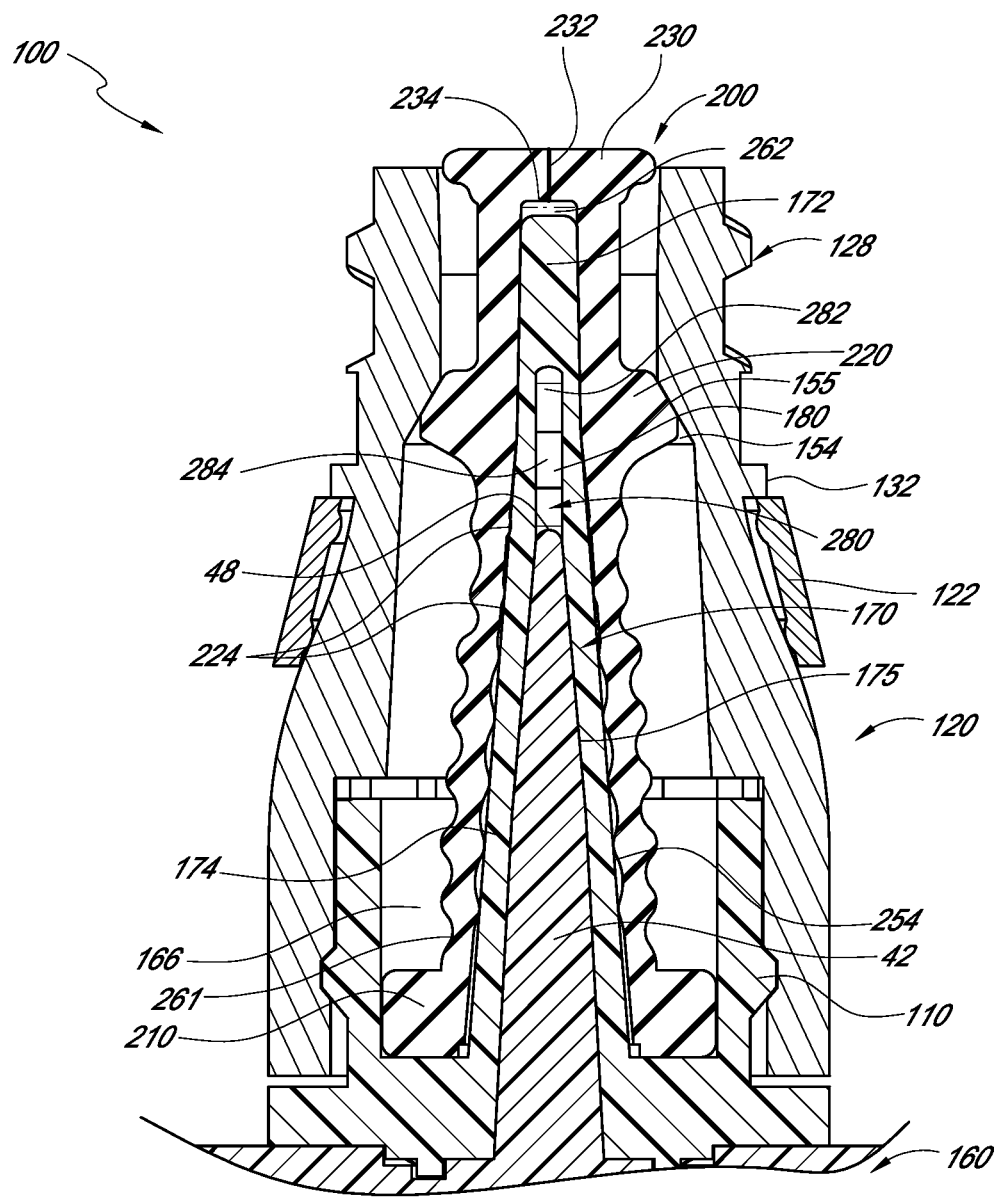
FIG. 19B is a cross-sectional view of the needleless connector of FIG. 19A, taken along the line 19B-19B of FIG. 19A.
Figure 20A:
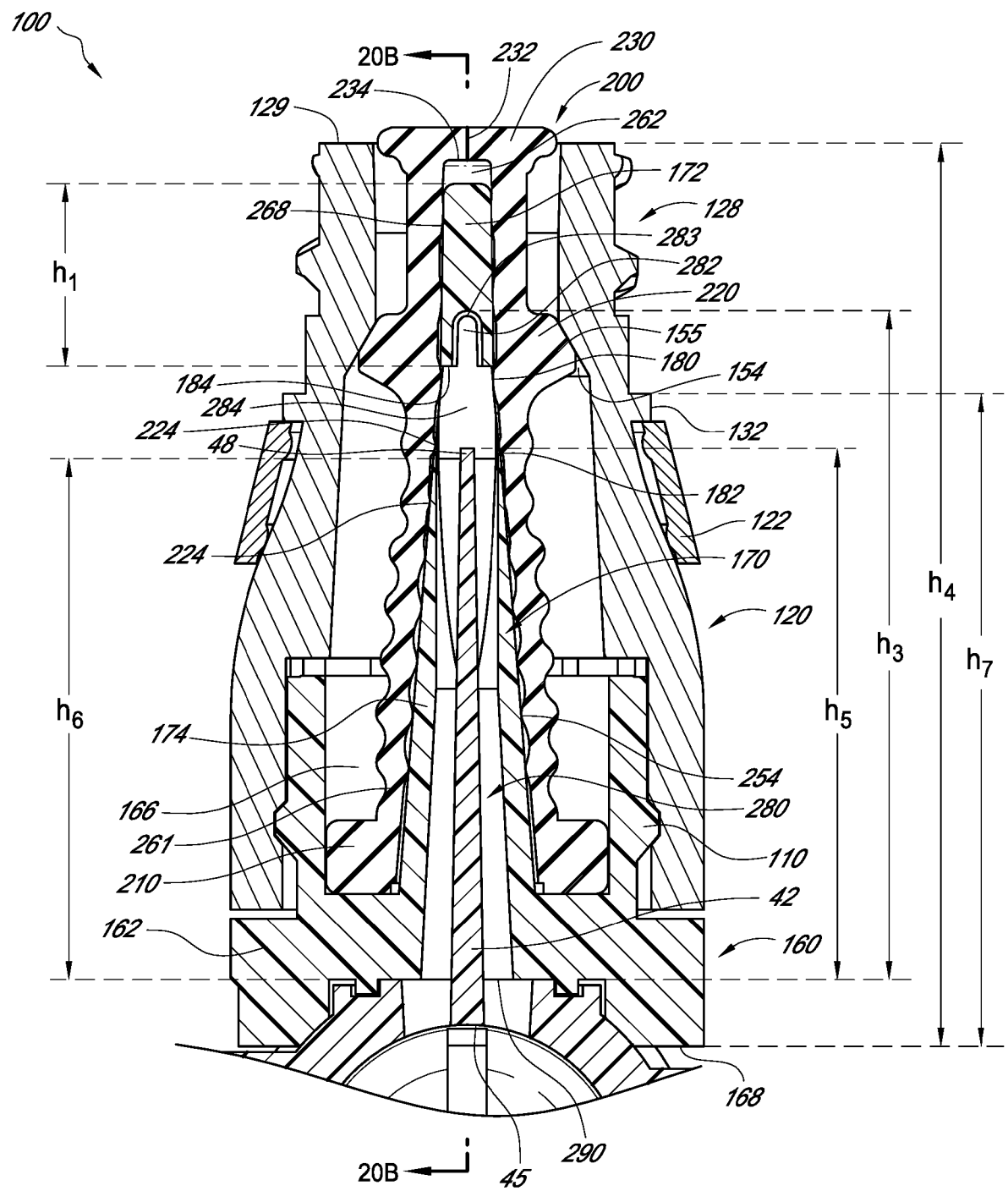
FIG. 20A is a cross-sectional view of a needleless connector positioned on a port of a stopcock.
Figure 20B:
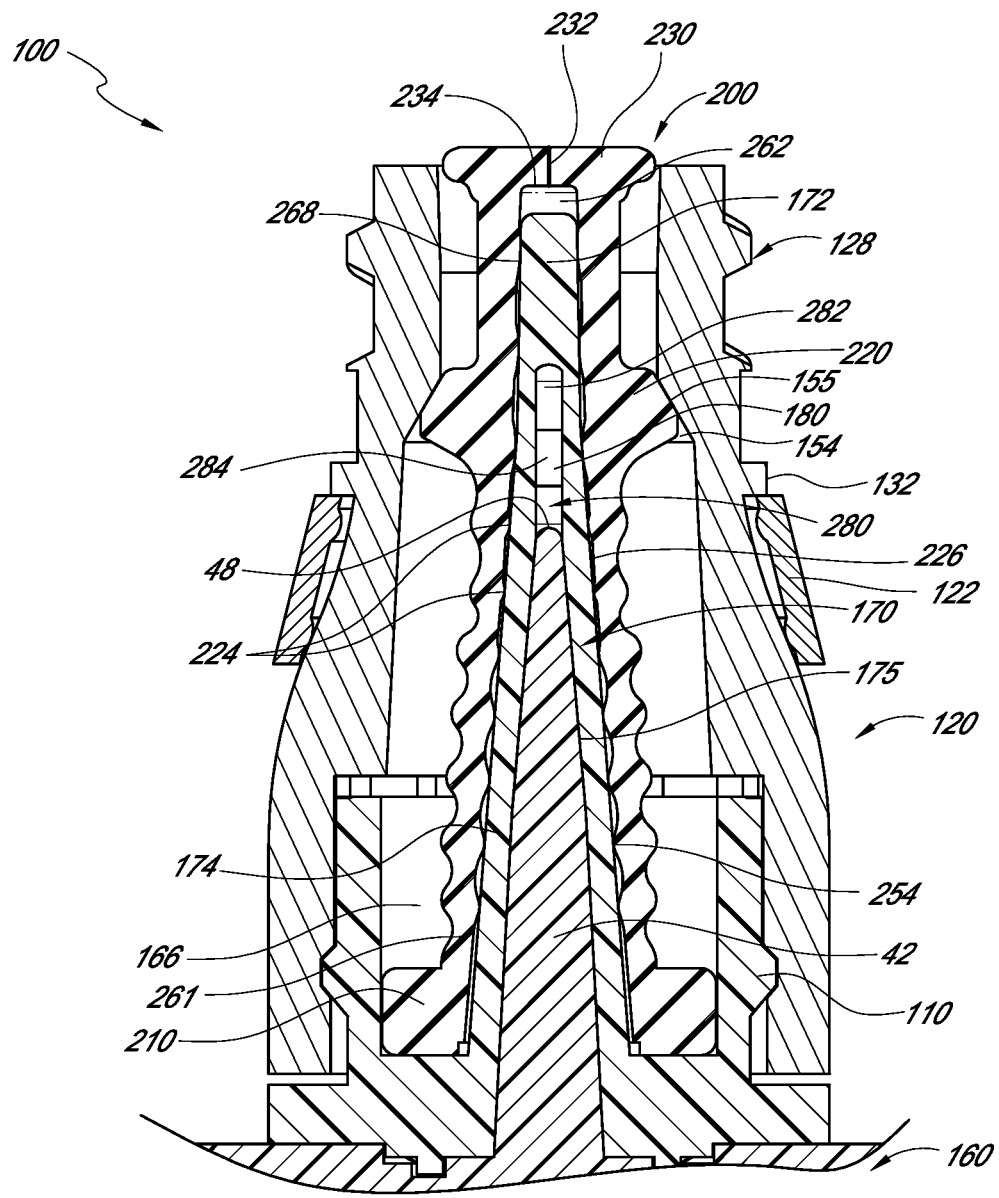
FIG. 20B is a cross-sectional view of the needleless connector of FIG. 20A, taken along the line 20B-20B of FIG. 20A.
Figure 21A:
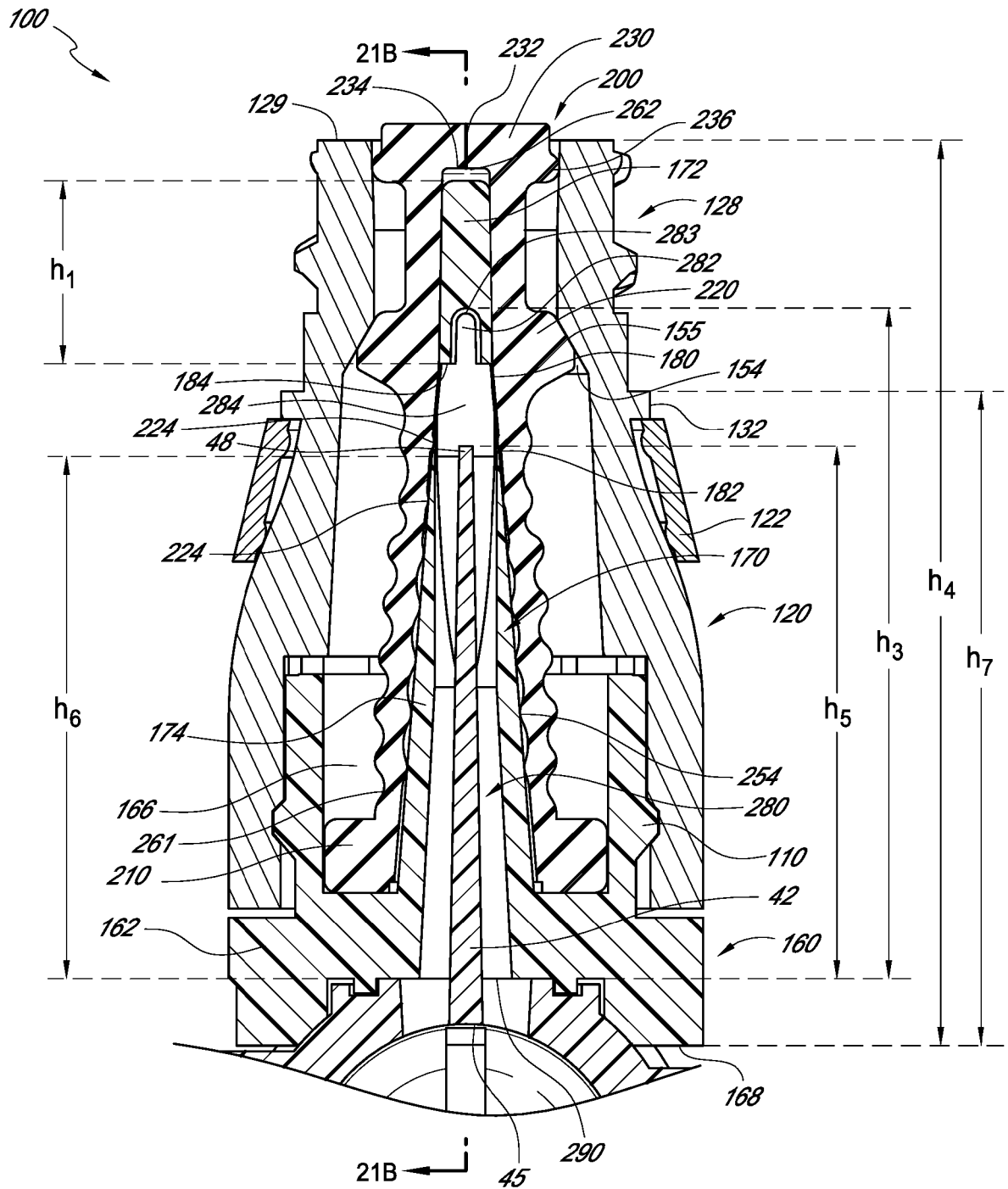
FIG. 21A is a cross-sectional view of a needleless connector positioned on a port of a stopcock.
Figure 21B:
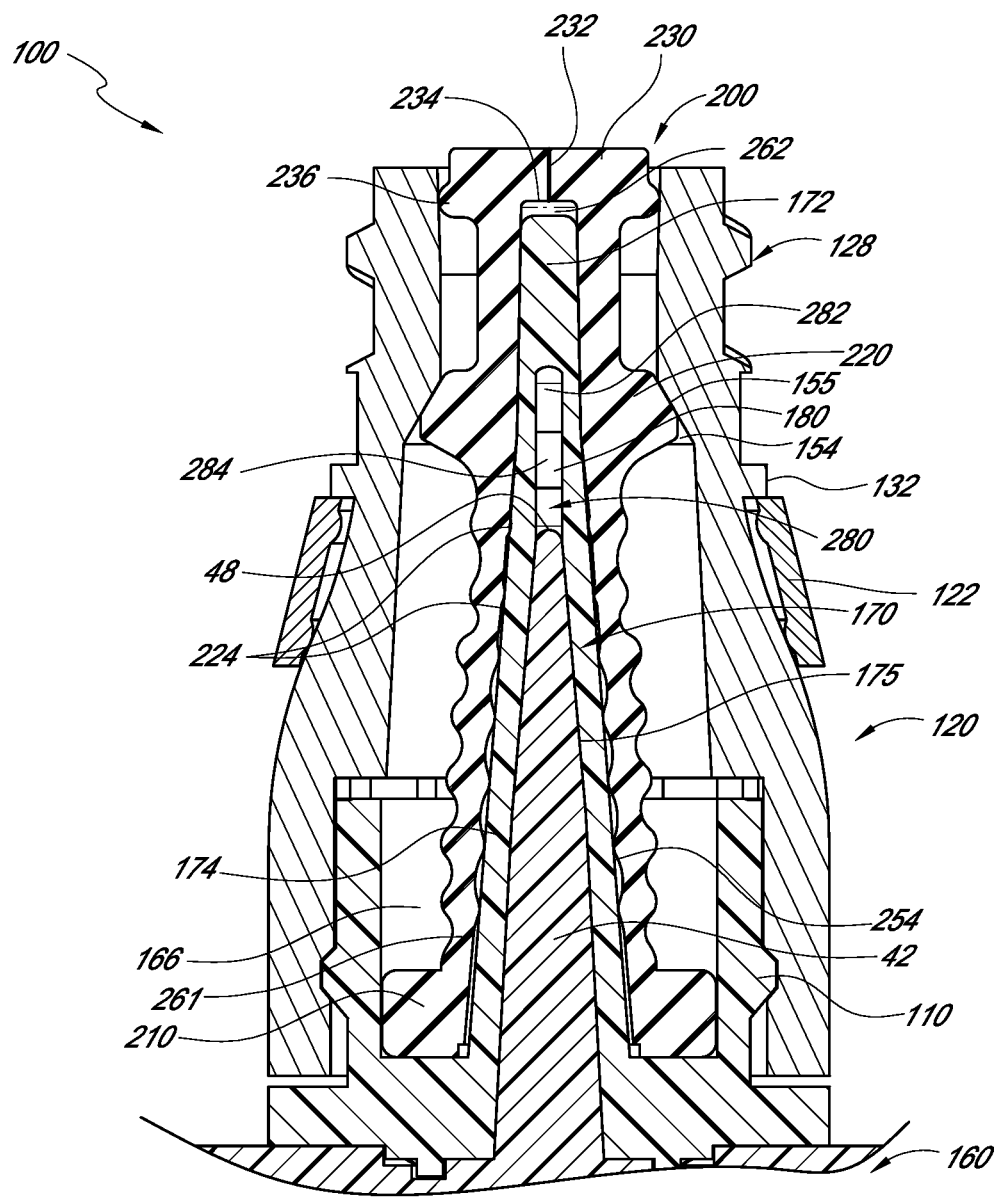
FIG. 21B is a cross-sectional view of the needleless connector of FIG. 21A, taken along the line 21B-21B of FIG. 21A.
Figure 22A:
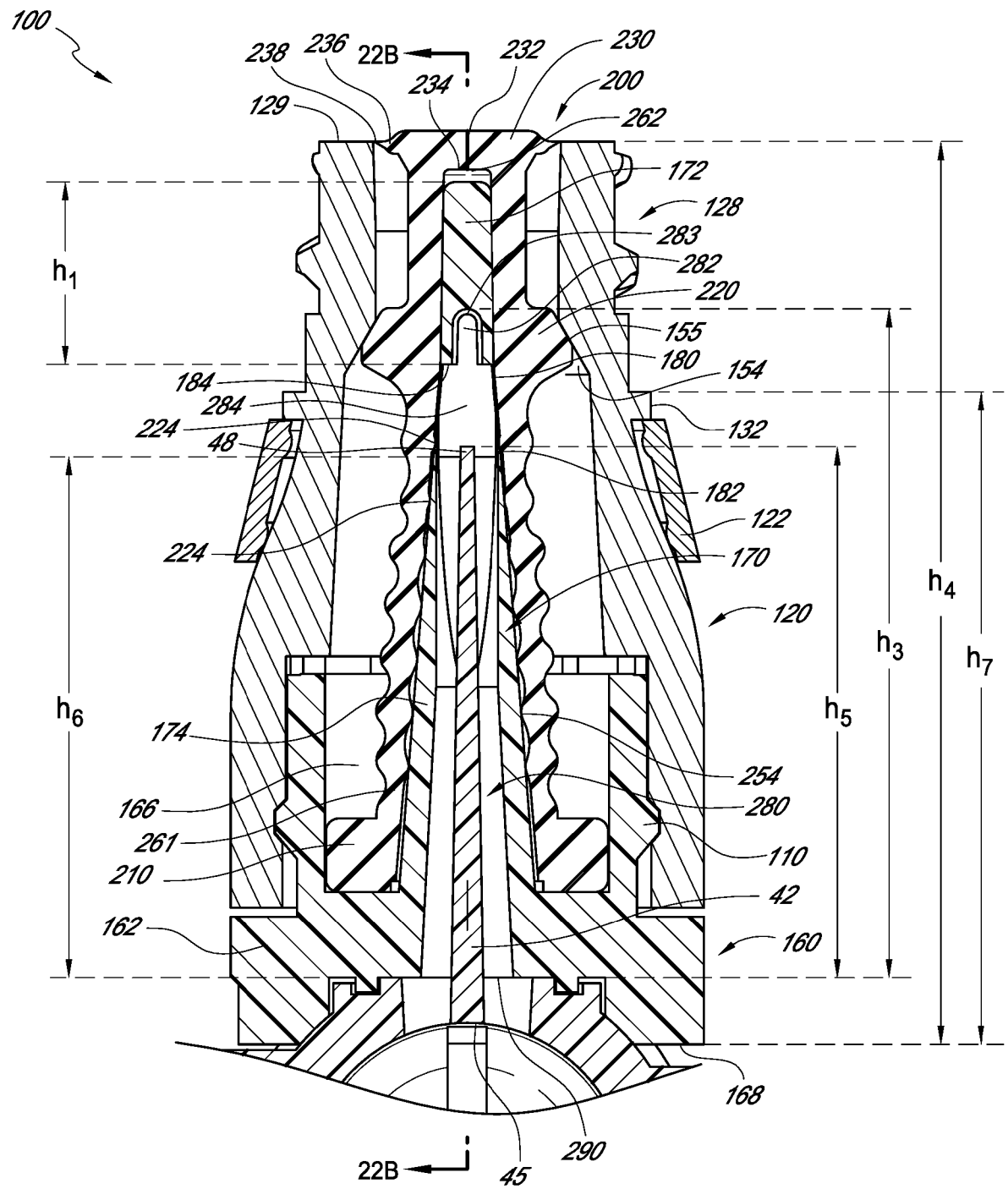
FIG. 22A is a cross-sectional view of a needleless connector positioned on a port of a stopcock.
Figure 22B:
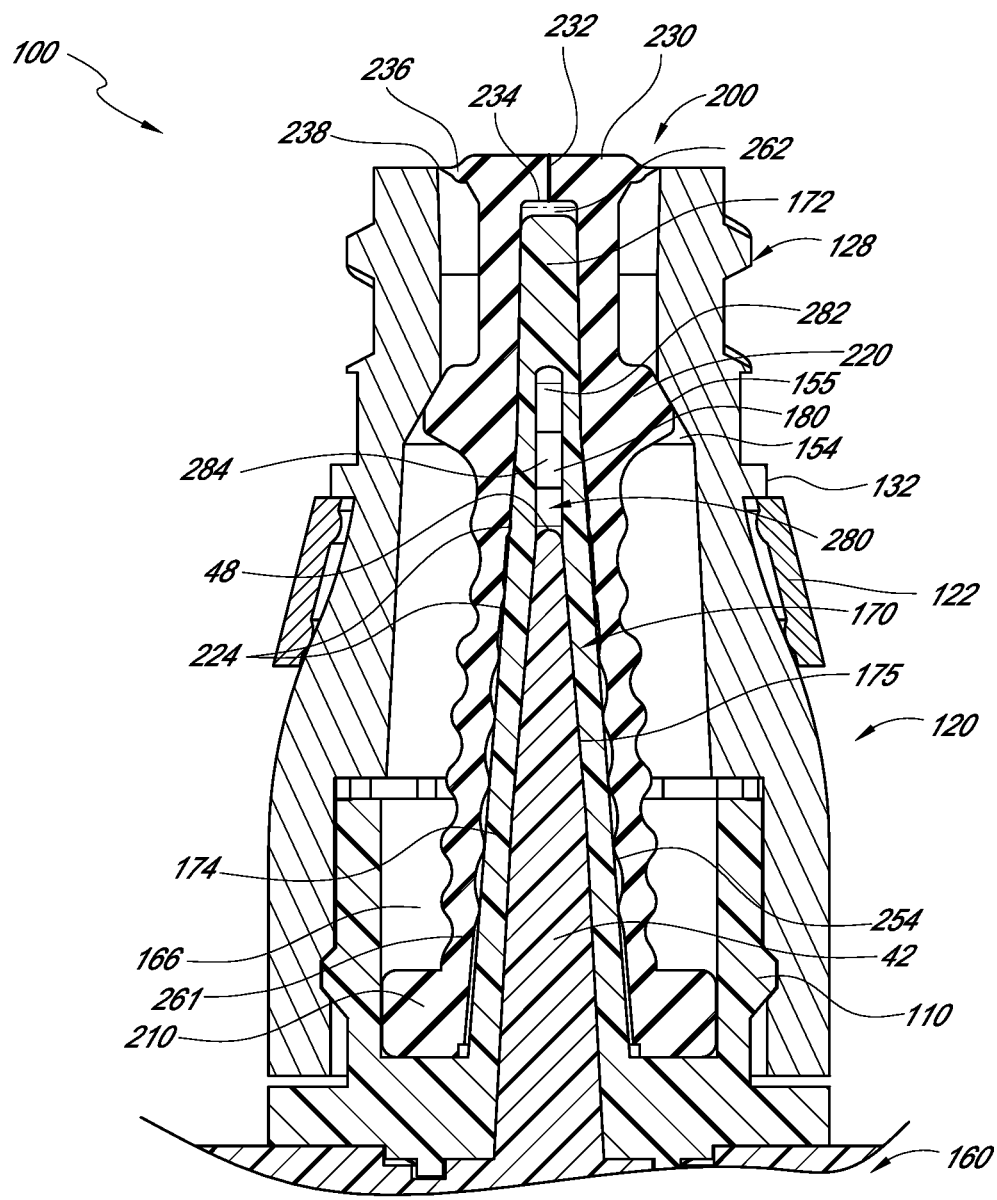
FIG. 22B is a cross-sectional view of the needleless connector of FIG. 22A, taken along the line 22B-22B of FIG. 22A.

FIGS. 16A and 16B illustrate a more detailed view of a needleless connector 100 positioned on a port of a stopcock with a fluid diverter 42. FIG. 16A is the same view of the needleless connector found in FIG. 12, and FIG. 16B is a view of the needleless connector taken along the line 16B-16B illustrated in FIG. 16A. FIGS. 17A and 17B illustrate the same views as FIGS. 16A and 16B, respectively, but with the valve member 200 of FIGS. 11C and 11D. FIGS. 18A and 18B illustrate the same views but with the valve member 200 of FIGS. 11E and 11F. FIGS. 19A and 19B illustrate the same views but with the valve member 200 of FIGS. 11G and 11H. FIGS. 20A and 20B illustrate the same views but with the valve member 200 of FIGS. 11I and 11J. FIGS. 21A and 21B illustrate the same views but with the valve member 200 of FIGS. 11K and 11L. FIGS. 22A and 22B illustrate the same views but with the valve member 200 of FIGS. 11M and 11N.

With respect to FIGS. 16A and 16B, in some embodiments, when the valve member 200 is in a closed position, a shoulder 220 of the valve member can abut a shoulder 155 on an interior of the needleless connector. This can help provide a consistent positioning of the valve member relative to the connector body 120. The valve member and the projection can be sized and configured such that when the valve member is in the closed position, two of the sealing rings 224 can be pressed against the tip 172 of the projection above the openings 180. One or more of the rings can create a seal against the tip.

In some embodiments, the two lower sealing rings 224 can be pressed against the projection body or partially against the projection body 174, thereby creating one or more seals against the projection body. In some embodiments, a portion of a sealing ring can extend above the bottom 182 of the openings 180. In some embodiments, an entire sealing ring can be above a bottom of the opening and below the top 184 of the openings.

In some embodiments, the valve member can have three sealing rings 224. In some embodiments, two sealing rings can contact the tip 172 of the projection above the openings, creating one or more sealed locations. At least a portion of the third sealing ring can contact the projection body 174 below the openings. In some embodiments, a valve member can have only two sealing rings, one in contact with the projection tip above the openings and one in contact with the projection body below the openings.

In some embodiments, if a sealing ring 224 configured to contact the projection body 174 below the openings 180 moves far enough up such that it no longer contacts the projection body, whether from an unexpected force on the valve member, changes in the physical properties of the valve member 200 through use, unexpected sizing of the openings 180 or sealing rings 224 due to manufacturing variance, or other variable, blood can pass below the sealing ring and be trapped between the valve member and the internal projection 170. Blood that is trapped between the valve member and the internal projection cannot be flushed or easily removed. To help prevent blood being thus trapped, in some embodiments a sealing ring 224 configured to contact the projection body 174 below the openings 180 can be made wide enough to ensure that a portion of the sealing ring maintains contact and a seal against the projection body 174. In some embodiments, the sealing ring can be made wider than other sealing rings. In some embodiments, a sealing ring 224 configured to contact and seal against a tip 172 of the projection 170 can be similarly made wide enough to ensure that it maintains contact and a seal against the tip, preventing fluid from passing the sealing ring and entering an upper interior section 262 of the valve member, as described below. In some embodiments, this sealing ring can be made wider than other sealing rings.

With respect to FIGS. 17A and 17B, and as described above, in some embodiments one or more of the sealing rings 224 can have a contact portion 226 between them. A contact portion can be sized such that when the sealing rings contact and seal against the projection 170, the contact portion can contact and/or be immediately adjacent the projection body. This can help prevent blood from passing below a sealing ring configured to contact the projection body 174 below the openings 180. Even if the sealing ring unexpectedly moves up far enough such that it no longer contacts the projection body, the contact portion can occupy all or substantially all of the space between the projection body 174, the valve member 200, and a sealing ring 224 further below. In some embodiments, a contact portion can seal against the projection member. FIGS. 17A and 17B also illustrate an embodiment in which one or more sealing rings 224 can extend at least partially into the windows 180.

Continuing with respect to FIGS. 17A and 17B, in some embodiments a medical connector can include an external indicator 122, which can be used to indicate the type of connector. In some embodiments, the indicator can be a marking or other visual indicator. In some embodiments, the indicator can be an indicator component, such as a ring, as illustrated. In some embodiments, an indicator can be of a different color than the rest of the connector body 120. In some embodiments, an indicator can be opaque while the rest of the connector body is translucent, transparent, and/or clear. In some embodiments, an indicator can be translucent, transparent, and/or clear.

In some embodiments, the valve member 200 and projection tip 172 can be sized to help prevent the passage of fluid into areas where the fluid may not be flushed out. This can occur, for example, after a valve member has been compressed by a medical implement, the medical implement is removed or being removed, and the valve member begins to return to the illustrated closed position. As the valve member moves upward, the top 230 of the valve member will pass the uppermost point of the projection tip 172, allowing the slit 232 to close and seal. As the valve member moves further up, the upper interior section 262 of the valve member can expand, which can create a negative pressure. This negative pressure can tend to draw fluids from the interior of the projection 280, through the openings 180, and into the interior upper section 262. The interior upper section may not get flushed by fluids diverted into the valve member by the fluid diverter 42, and any fluid that reaches the upper section may tend to stay there until a medical implement is again connected.

In some embodiments, to help prevent this accumulation of fluid, the tip 172 of the projection can be sized such that when the projection passes back through the slit 232 as the valve member moves back toward the closed position, a sealing ring 224 can already be in contact with the tip of the projection. In some embodiments, this sealing ring can create a seal against the tip of the projection sufficient to prevent fluid from passing into the upper interior section 262 of the valve member. The negative pressure generated by the expansion of the upper interior section can instead draw a small amount of air through the slit. In some embodiments, the seal formed by the slit is strong enough such that the negative pressure is maintained in the upper interior section until a medical implement is again inserted into the needleless connector, opening the slit. As discussed above, the negative pressure can be reduced by incorporating a neck section 240 that resists compression and/or radial expansion.

In some embodiments, the height $h_1$ of the tip 172 of the projection can be equal to or greater than the height $h_2$ between the uppermost sealing ring 224 and the bottom interior surface 234 of the top of the valve member. This can help ensure that a sealing ring is in contact with the tip of the projection when space begins to develop in the upper interior section 262 of the valve member. In some embodiments, the height $h_1$ can be greater than $h_2$. In some embodiments, the height $h_1$ can be such that the top of the projection tip 172 extends to and/or touches the bottom interior surface 234 of the top 230 of the valve member 200 when the valve member is in the closed position.

In some embodiments, as illustrated in FIG. 17A, in addition to or in alternative to adjusting the size of the tip 172, the thickness of the top 230 or the positioning of the sealing rings 224 can be adjusted to help ensure that when the projection 170 passes through the slit 232 as the valve member 200 moves toward the closed position, a sealing ring 224 can be in contact with the tip of the projection. In some embodiments, the ratio of the heights $h_1$ to $h_2$ can be greater than or equal to approximately 1 and/or less than or equal to approximately 3. In some embodiments, the ratio of the heights $h_1$ to $h_2$ can be greater than or equal to approximately 1 and/or less than or equal to approximately 2.5. In some embodiments, the ratio of the heights $h_1$ to $h_2$ can be greater than or equal to approximately 1 and/or less than or equal to approximately 2. In some embodiments, the ratio of the heights $h_1$ to $h_2$ can be greater than or equal to approximately 1 and/or less than or equal to approximately 1.5. In some embodiments, the ratio of the heights $h_1$ to $h_2$ can be greater than or equal to approximately 1.2 and/or less than or equal to approximately 1.7. In some embodiments the ratio can be less than 1. In some embodiments, the tip 172 can extend at least partially into the slit 232.

Embodiments where the valve member compresses and expands non-uniformly, described above with respect to FIGS. 13 and 14, can also help preclude fluid from collecting in an interior upper section 262 of the valve member. For example, a delayed expansion of a lower section relative to an upper section of the valve member can help ensure that a sealing ring contacts the projection tip 172 of the projection 170 when the uppermost point of the projection tip 172 passes through the slit 232, allowing the slit to close and space to begin to form in the upper interior section 262 of the valve member. As described above, the seal between the sealing ring and the projection tip can prevent fluid from entering the upper interior section.

In some embodiments, as illustrated in FIGS. 18A and 18B and as discussed above, the valve member 200 can prevent fluid from collecting in an interior upper section 262 of the valve member without having any sealing rings positioned to contact the tip 172 of the internal projection 170 above the openings 180. The valve member can have an interference fit with the internal projection that prevents fluid from passing between the two. In some embodiments, a width of the interior upper section 262 can be approximately equal to a width of the tip 172 at a corresponding position on the tip. In some embodiments, a width of the interior upper section can be slightly less than a width of the tip at a corresponding position on the tip. In such embodiments, the internal projection 170 can expand the valve member at the interior upper section 262, creating a tighter fit between the valve member and the projection.

In some embodiments, the shoulder 220 of the valve member and the shoulder 155 in an interior of the needleless connector can be sized and configured to such that the shoulder 155 of the connector pushes against the shoulder 220 of the valve member to sustain or increase a contact pressure between the valve member and the projection 170. This can also help prevent undesirable fluid from collecting in an interior upper section 262 of the valve member while allowing the valve member and projection to be configured for reduced friction between them. In some embodiments, this can allow the valve member and projection to be configured for minimal friction between them. In some embodiments, the shoulder of the connector and/or the shoulder of the valve member can be configured to form a desired contact pressure between the valve member and the projection. In some embodiments, one or more components of the valve member can have a lubricating agent incorporated into their structure, from where the lubricating agent can leach out. For example, in some embodiments a lubricating agent can be incorporated into the silicone matrix of the valve member and can bleed out over time, helping reduce friction between the valve member 200 and the internal projection 170.

In some embodiments, the height $h_1$ of the tip of the projection can vary. The height of the tip can affect the available surface area for contact between the internal projection 170 and the valve member 200. This can impact the ability to prevent fluid from accumulating in the upper interior section 262 of the valve member. In some embodiments, the height $h_1$ can be greater than or approximately equal to a height of the opening 180, measured from the bottom 182 of the opening to the top 184 of the opening. In some embodiments, the height of the tip of the projection can be greater than or equal to approximately three quarters of the height of the opening 180, greater than or equal to approximately one half of the height of the opening, or greater than or equal to about one quarter of the height of the opening.

FIGS. 19A and 19B illustrate a connector 100 with a valve member that has a base 210 according to the embodiment described above with respect to FIGS. 11G and 11H. They also illustrate a valve member where the section 261 of valve member wall adjacent the base can be thinner than other sections of the valve member wall.

In some embodiments, as illustrated in FIGS. 20A and 20B and as discussed above, surface roughenings 268 can help decrease the friction between the valve member 200 and the internal projection 170, while still preventing fluid from collecting in an interior upper section 262. In some embodiments, the amount and/or degree of roughening can depend upon the intended use for the valve member. Generally, the more time that a valve member will remain in an opened position without returning to a closed position, the greater the amount and/or degree of roughening desired. Greater roughening can limit friction between the valve member and the internal projection, which can help allow the valve member to return to a closed position after remaining in an opened position for a period of time. In some embodiments, in addition to or as an alternative to providing greater roughening to limit the friction between the valve member and the internal projection, the valve member can be configured to fit around the internal projection with varying degrees of tightness. This is described in more detail below. Surface roughenings can also trap oil or other lubricant between the inner surface of the valve member and the internal projection to facilitate movement of the valve member relative to the internal projection. In some embodiments, oil or other lubricant can fill any available space between the surface roughenings and the internal projection. This can help resist seepage of blood between the projection and the valve member.

In some embodiments, surface roughenings 268, such as scallops, can compress when pressed against the internal projection member. This can occur when the valve member 200 is in an open position and/or when the valve member is in a closed position. In some embodiments, the compression of the roughenings can be small enough to limit distortion of the roughenings as they move along the spike when a medical implement is attached to or removed from a medical connector, as illustrated in FIG. 14. In some embodiments, the compression of the roughenings can also be small enough to help prevent the roughenings from catching on the projection member 170, such as openings 180. In some embodiments, the roughenings can compress a distance greater than or equal to approximately 0.0005 inches and/or less than or equal to approximately 0.002 inches. In some embodiments, the roughenings can compress a distance greater than or equal to approximately 0.0005 inches and/or less than or equal to approximately 0.0015 inches. In some embodiments, the roughenings can compress a distance greater than or equal to approximately 0.0008 inches and/or less than or equal to approximately 0.0012 inches. In some embodiments, the roughenings can compress a distance approximately equal to 0.001 inches.

In some embodiments, the amount a surface roughening compresses can be measured as a ratio of its width $w_2$, described above with respect to FIG. 11P, to the amount it compresses. In some embodiments, the ratio of the width $w_2$ to the amount of surface roughening compression can be greater than or equal to approximately 10 and/or less than or equal to approximately 60. In some embodiments, the ratio of the width $w_2$ to the amount of surface roughening compression can be greater than or equal to approximately 20 and/or less than or equal to approximately 60. In some embodiments, the ratio of the width $w_2$ to the amount of surface roughening compression can be greater than or equal to approximately 30 and/or less than or equal to approximately 50. In some embodiments, the ratio of the width $w_2$ to the amount of surface roughening compression can be greater than or equal to approximately 40 and/or less than or equal to approximately 50. In some embodiments the ratio can be approximately 45.

In some embodiments, the various amounts and ratios of compression reflect the compression that naturally occurs by positioning the valve member 200 around the internal projection member 170. For ease of reference, this will be referred to as interference compression. In some embodiments, the amounts and ratios of compression described reflect the interference compression in combination with the compression from the force provided by the interaction of the shoulder 220 of the valve member and the shoulder 155 in an interior of the needleless connector, as described above. In some embodiments, the interference compression is sufficient to prevent undesirable fluid from collecting in an interior upper section 262 of the valve member. In some embodiments, the interference compression alone is insufficient to prevent fluid from collecting. In other words, in some embodiments the surface roughenings are such that the valve member 200 when positioned around the internal projection member 170 does not by itself create a seal strong enough to block backflow from passing between the valve member and the projection member at operating pressures. This can help minimize friction between the valve member and the projection member. In such embodiments, as shown in the drawings, additional force from other interactions with the valve member, such as between shoulder 220 and shoulder 155, can be relied upon to help create a seal between the valve member and the projection member that prevents backflow between the internal projection member and the valve at operating pressures.

In some embodiments, for example, the interference compression prevents backflow only below pressures of approximately 30 psi. In some embodiments, the interference compression prevents backflow only below pressures of approximately 20 psi. In some embodiments, the interference compression prevents backflow only below pressures of approximately 15 psi. In some embodiments, the interference compression prevents backflow only below pressures of approximately 10 psi. In some embodiments, the interference compression prevents backflow only below pressures of approximately 7 psi. In some embodiments, the interference compression prevents backflow only below pressures of approximately 5 psi. In some embodiments, the interference compression prevents backflow only below pressures of approximately 3 psi. In some embodiments, the interference compression prevents backflow only below pressures of approximately 1 psi. In some embodiments, the interference compression does not prevent backflow at pressures above approximately zero psi.

In some embodiments, the interference compression is limited because of a relative similarity between a minimum inner diameter of surface roughenings 268 on the valve member and a corresponding outer diameter of the projection member 170 when the valve member is in the closed position. For example, in some embodiments the difference between a minimum inner diameter of a surface roughening, such as a scallop, and an outer diameter of the projection member where it contacts the surface roughening can be less than or equal to approximately 0.010 inches. In some embodiments, the difference can be less than or equal to approximately 0.008 inches. In some embodiments, the difference can be less than or equal to approximately 0.006 inches. In some embodiments, the difference can be less than or equal to approximately 0.004 inches. In some embodiments, the difference can be less than or equal to approximately 0.002 inches.

In some embodiments, the minimum inner diameter of surface roughenings 268 can be compared to the outer diameter of the projection member 170 at the top 184 of the openings 180 in the projection member. The difference between the minimum inner diameter of the surface roughenings and the outer diameter of the projection member at the top of the openings can vary in different embodiments in the same manner as described above. For example, in various embodiments, the difference can be less than or equal to approximately 0.010 inches, less than or equal to approximately 0.008 inches, less than or equal to approximately 0.006 inches, less than or equal to approximately 0.004 inches, or less than or equal to approximately 0.002 inches. This difference can affect the amount of backflow pressure that the valve member can resist. It can also affect the interference compression.

In some embodiments, the minimum inner diameter of surface roughening 268 can be compared to the thickness $t_1$ of the base 210. For example, in some embodiments the ratio of the thickness $t_1$ to the minimum inner diameter can be greater than or equal to approximately 0.5 and/or less than or equal to approximately 1.5. In some embodiments the ratio of the thickness $t_1$ to the minimum inner diameter can be greater than or equal to approximately 1 and/or less than or equal to approximately 2. In some embodiments the ratio of the thickness $t_1$ to the minimum inner diameter can be greater than or equal to approximately 1.5 and/or less than or equal to approximately 2.5. In some embodiments the ratio of the thickness $t_1$ to the minimum inner diameter can be greater than or equal to approximately 1.75 and/or less than or equal to approximately 2.25.

In some embodiments, as illustrated in FIGS. 21A through 22D and as discussed above, valve members 200 can have external seals 236 to help prevent blood from collecting between the valve member and the body 120 of the needleless connector if a seal between the tip 310 of a medical implement and the top of the valve member breaks. In some embodiments, the outer diameter $OD_1$ of the seal 236 (illustrated in FIGS. 11K and 11M) can be greater than the inner diameter $ID_1$ of the connector body 120 at the top of the body (illustrated in FIG. 10) or where the seal 236 aligns with the connector body in the closed position. Thus, when the valve member is positioned within the body 120, an interference can exist between the body and the seal 236 such that the seal is compressed inward, sealing against the body. If blood or other fluid flows onto the top of the valve member, most or all of the blood or other fluid will remain there and not flow past the seal 236. In some embodiments, the outer diameter $OD_1$ of the seal 236 can be greater than the inner diameter $ID_1$ of the connector body 120 where the seal aligns with the connector body in the open position. In some embodiments, an interference can exist between the body and the seal across the complete range of motion of the valve member.

The relative dimensions of the outer diameter $OD_1$ of the seal 236 and the inner diameter $ID_1$ of the connecter body where the seal 236 contacts the connector body can affect how tight of a seal is formed between the seal 236 and the connector body 120. The dimensions can also affect the amount of friction between the seal 236 and the connector body, which affects how easily the valve member 200 transitions to and from the open and closed positions. In some embodiments, the outer diameter $OD_1$ can be between approximately one and approximately 20 thousandths of an inch greater than the inner diameter $ID_1$. In some embodiments, the outer diameter $OD_1$ can be between approximately one and approximately 10 thousandths of an inch greater than the inner diameter $ID_1$. In some embodiments, the outer diameter $OD_1$ can be between approximately two and approximately eight thousandths of an inch greater than the inner diameter $ID_1$. In some embodiments, the difference between the outer diameter and the inner diameter can be less than approximately one thousandths of an inch or greater than approximately 20 thousandths of an inch.

In some embodiments, the outer diameter $OD_1$ of the seal 236 can be varying percentages larger than the inner diameter $ID_1$ of the connector body. For example, in some embodiments the outer diameter $OD_1$ can be between approximately 0.5% and approximately 15% larger than the inner diameter $ID_1$. In some embodiments the outer diameter $OD_1$ can be between approximately 1% and approximately 10% larger than the inner diameter $ID_1$. In some embodiments the outer diameter $OD_1$ can be between approximately 2% and approximately 5% larger than the inner diameter $ID_1$. In some embodiments the outer diameter $OD_1$ can be between less than approximately 1% or greater than approximately 15% larger than the inner diameter $ID_1$. The relative dimensions of the inner diameter $ID_1$ and outer diameter $OD_1$ described herein are with respect to the components of a medical connector before it is fully assembled. Additionally, in various embodiments the relative dimensions provided can refer to the outer diameter where the seal 236 aligns with the connector body in the open position, where the seal aligns with the connector body in the closed position, or where the seal aligns with the connector body in any or all positions between the open and the closed position.

In some embodiments, in addition to providing a seal to prevent blood or other fluids from flowing between the valve member 200 and connector body 120, a seal 236 can act to wipe some or all of any fluids that accumulate along the interior walls of the upper portion 128 of the needleless connector body. The seal 236 can wipe the interior walls as the valve member moves from an open to a closed position. Any fluids can then be cleaned by swabbing and/or disinfecting the top of the valve member. In some embodiments, a seal 236 with a tip 238, such as that of FIGS. 11M and 11N and FIGS. 22A through 22D, can be particularly effective at wiping any fluid from the interior walls of the upper portion of the connector body.

Figure 22C:
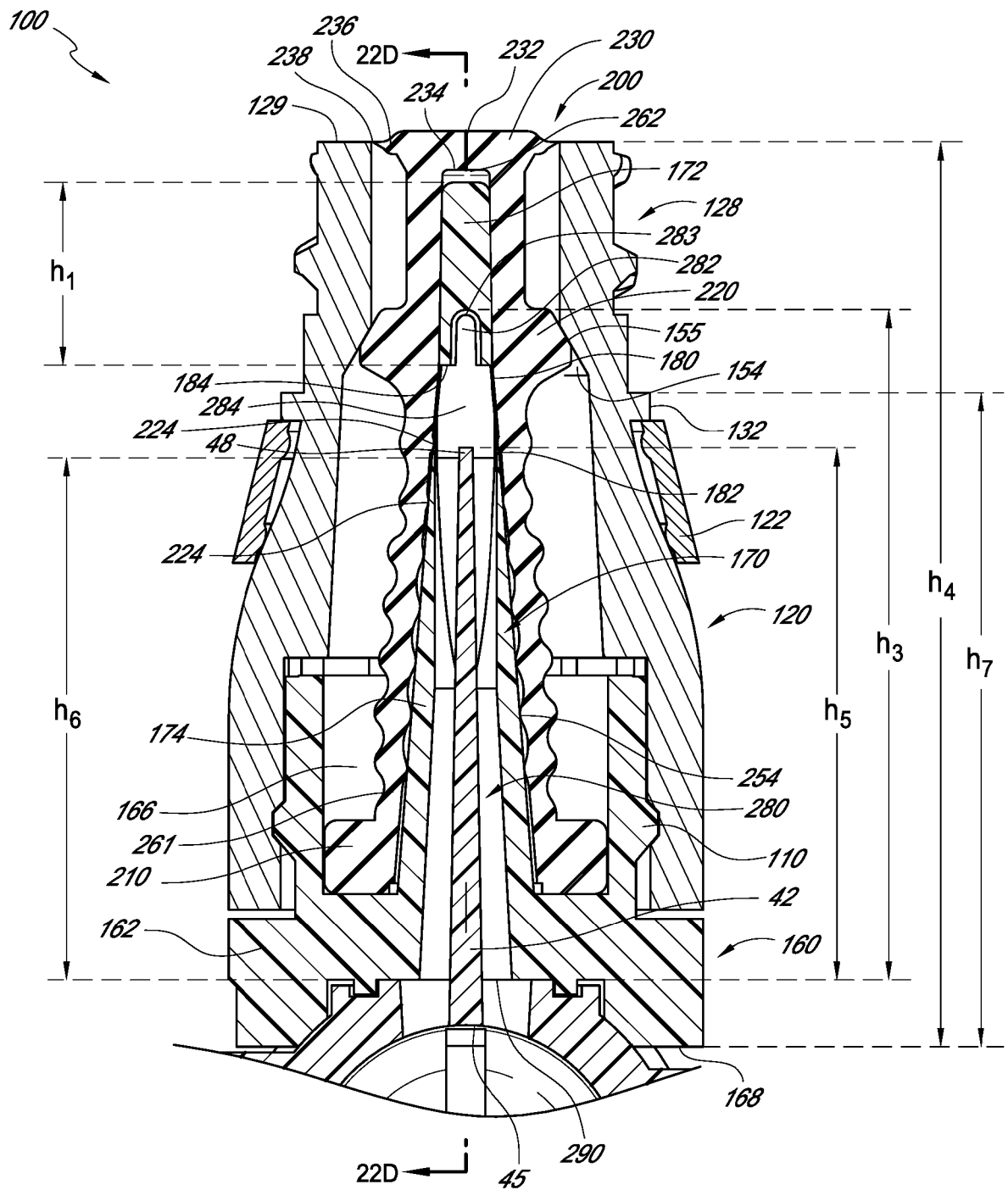
FIG. 22C is a cross-sectional view of a needleless connector positioned on a port of a stopcock.
Figure 22D:
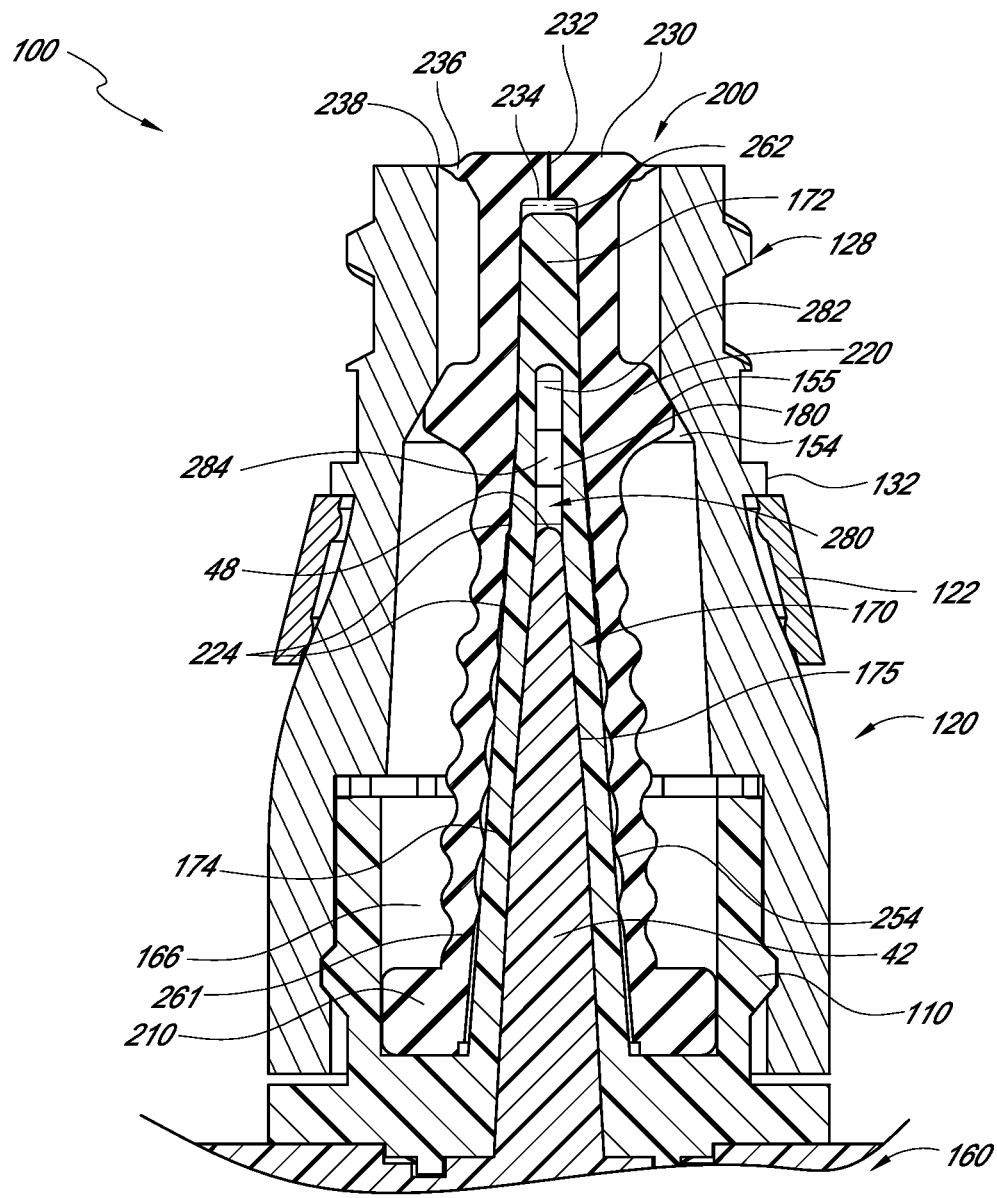
FIG. 22D is a cross-sectional view of the needleless connector of FIG. 22C, taken along the line 22D-22D of FIG. 22C.

In some embodiments, it can be preferable to have a constant interference between the seal 236 and the connector body 120. This can help ensure a consistent seal, wiping, and/or a consistent amount of friction between the seal and body. FIGS. 22C and 22D illustrate one embodiment of a medical connector 100 that has the valve member 200 of FIGS. 22A and 22B, but that has a connector body 120 with an upper portion 128 having a constant inner diameter. In various embodiments, a connector body with an upper portion 128 having a constant inner diameter can be used with any valve member described herein and any combination of elements described herein.

As described above, in various embodiments a seal 236 can be located at different positions relative to the connector body 120 when the valve member is in a closed position. For example, as illustrated in FIGS. 21A and 21B, in some embodiments the seal can be located below a top surface of the connector body. In contrast, in some embodiments, as illustrated in FIGS. 22A through 22D, a tip 238 of the seal can be generally flush with a top of the connector body. Preferably, a seal is close enough to the top such that a care provider can disinfect the top of the seal by swabbing across the top of the connector. In some embodiments, the interaction between the shoulders 220 of the valve members and shoulders 155 of the connector body 120 can help ensure that the seal 236 does not move out of position within the connector body. In various embodiments, any of the valve members described herein can include seals 236 as described.

In various embodiments, the flow path of diverted fluid and/or the fluid diverter 42 itself can reach different heights within the needleless connector 100. In various embodiments, the flow path of diverted fluid and/or the distal tip 48 of the fluid diverter can be defined with respect to a height $h_3$ of the interior 280 of the projection 170, measured from the opening 290 at the bottom of the internal projection member 170 to the distal most surface 283 of the interior 280 of the projection 170. The flow path and/or the top of the fluid diverter can also or alternatively be defined with respect to a height $h_4$ of the connector 100, measured from the bottom surface 168 of the connector 100 to the distal surface 129 of the connector body 120, or a height $h_7$ of the shoulder or collar 132 measured from the bottom surface 168 to a top of the shoulder 132.

In some embodiments, the fluid diverter 42 directs fluid and/or the fluid diverter 42 extends a substantial distance into the connector 100. In some embodiments, a substantial distance can be further into the medical connector than the collar 190. In some embodiments, a substantial distance can be further into the medical connector than the base section 160 extends away from the connecting portion. In some embodiments, a substantial distance can be any distance identified below. In some embodiments, the fluid diverter 42 directs fluid and/or the fluid diverter 42 extends into the distal about two thirds of the height $h_4$ of the connector 100. In some embodiments, the fluid diverter directs fluid and/or the fluid diverter 42 extends into the distal about one half of the height $h_4$ of the connector. In some embodiments, the fluid diverter directs fluid and/or the fluid diverter 42 extends into the distal about one third of the height $h_4$ of the connector. In some embodiments, the fluid diverter directs fluid and/or the fluid diverter 42 extends into the distal about one quarter of the height $h_4$ of the connector.

In some embodiments, the fluid diverter can similarly divert fluid and/or the fluid diverter 42 extends into the distal about two thirds of the height $h_3$ of the interior 280 of the projection 170 or of the height $h_7$ of the shoulder or collar 132. In some embodiments, the fluid diverter can similarly divert fluid and/or the fluid diverter 42 extends into the distal about one half of the height $h_3$ or of the height $h_7$. In some embodiments, the fluid diverter can similarly divert fluid and/or the fluid diverter 42 extends into the distal about one third of the height $h_3$ or of the height $h_7$. In some embodiments, the fluid diverter can similarly divert fluid and/or the fluid diverter 42 extends into the distal about three sixteenths of the height $h_3$ or of the height $h_7$. In some embodiments, the fluid diverter can similarly divert fluid and/or the fluid diverter 42 extends into the distal about one eighth of the height $h_3$ or of the height $h_7$. In some embodiments, the fluid diverter can similarly divert fluid and/or the fluid diverter 42 extends into the distal about one sixteenth of the height $h_3$ or of the height $h_7$. In some embodiments, the fluid diverter directs fluid and/or the fluid diverter 42 extends into the opening section 284 of the projection interior. In some embodiments, the fluid diverter directs fluid into the distal most section 282 of the projection interior and/or to a position distal to the shoulder or collar 132.

The height $h_5$ of the fluid diverter 42 within the interior projection member 170 can also be defined, and can impact how effectively the needleless connector can be flushed by fluid passing through the stopcock. The height $h_5$ of the fluid diverter 42 can be measured from the opening 290 at the bottom of the internal projection member 170 to the upper or distal tip 48 of the fluid diverter. In some embodiments, the height $h_5$ of the fluid diverter can be at least about 50 percent of the height $h_3$ of the interior 280 of the projection 170. In some embodiments, the height $h_5$ can be at least about 70 percent of the height $h_3$. In some embodiments, the height $h_5$ can be at least about 75 percent of the height $h_3$. In some embodiments, the height $h_5$ can be at least about 80 percent of the height $h_3$. In some embodiments, the height $h_5$ can be at least about 85 percent of the height $h_3$. In some embodiments, the height $h_5$ can be at least about 90 percent of the height $h_3$. In some embodiments, the height $h_5$ can be at least about 95 percent of the height $h_3$.

In some embodiments, the height of the fluid diverter 42 can be defined relative the openings 180 of the projection 170. For example, in some embodiments, the upper tip can be level with, or approximately level with, the bottom of the openings 180. In some embodiments the upper tip 48 of the fluid diverter 42 can extend past the bottom 182 of the openings 180. In some embodiments, the upper tip of the fluid diverter can extend past the bottom 182 of the openings 180 a distance that is at least about 5 percent of the distance from the bottom 182 of the openings 180 to the top 184 of the openings 180. In some embodiments, the upper tip of the fluid diverter can extend past the bottom 182 of the openings 180 a distance that is at least about 10 percent of the distance from the bottom 182 of the openings 180 to the top 184 of the openings 180. In some embodiments, the upper tip of the fluid diverter can extend past the bottom 182 of the openings 180 a distance that is at least about 20 percent of the distance from the bottom 182 of the openings 180 to the top 184 of the openings 180. In some embodiments, the upper tip of the fluid diverter can extend past the bottom 182 of the openings 180 a distance that is at least about 30 percent of the distance from the bottom 182 of the openings 180 to the top 184 of the openings 180.

In some embodiments, the upper tip 48 does not extend all the way to the bottom of the openings 180. In some embodiments, the upper tip can extend at least about 40 percent of the way up a height $h_6$ from the opening 290 near the bottom of the needleless connector base 160 to the bottom 182 of the openings 180 in the projection 170. In some embodiments, the upper tip can extend at least about 60 percent of the way up the height $h_6$. In some embodiments, the upper tip can extend at least about 70 percent of the way up the height $h_6$. In some embodiments, the upper tip can extend at least about 85 percent of the way up the height $h_6$. In some embodiments, the upper tip can extend at least about 90 percent of the way up the height $h_6$. In some embodiments, the upper tip can extend at least about 95 percent of the way up the height $h_6$.

The available volume of space within the projection member 170 can also impact how effectively the needleless connector can be flushed by fluid passing through the stopcock. Generally, the less volume that needs to be flushed, the more efficiently and the more easily flushing can occur. This available volume can also be referred to as the priming volume. When the connector has been primed with a fluid, the volume within the connector has been filled with the fluid to the extent it receives fluid.

In some embodiments, it can be preferable to have a volume of available space within the projection member 170 that is greater than or equal to approximately 0.005 mL and/or less than or equal to approximately 0.03 mL. In some embodiments, the available volume can be greater than or equal to approximately 0.01 mL and/or less than or equal to approximately 0.02 mL. In some embodiments, the available volume can be greater than or equal to approximately 0.013 mL and/or less than or equal to approximately 0.017 mL. In some embodiments, the available volume can be approximately 0.015 mL.

In some embodiments, the volume of the fluid diverter 42 within the projection member 170 can vary, thereby affecting the available volume within the fluid diverter. In some embodiments, the fluid diverter volume within the projection member can be greater than or equal to approximately 0.002 mL and/or less than or equal to approximately 0.03 mL. In some embodiments, the fluid diverter volume within the projection member can be greater than or equal to approximately 0.004 mL and/or less than or equal to approximately 0.025 mL. In some embodiments, the fluid diverter volume within the projection member can be greater than or equal to approximately 0.006 mL and/or less than or equal to approximately 0.02 mL. In some embodiments, the fluid diverter volume within the projection member can be greater than or equal to approximately 0.007 mL and/or less than or equal to approximately 0.015 mL. In some embodiments, the fluid diverter volume within the projection member can be approximately 0.009 mL.

As illustrated in FIGS. 16B and 17B and as discussed above, in some embodiments the profile of the fluid diverter 42 can be sized and shaped to track the internal profile of the projection body 174. In some embodiments, all or a substantial portion of the fluid diverter tracks the internal profile of the projection body, while in some embodiments only a portion of the fluid diverter does so. In some embodiments, the fluid diverter can be configured to touch and/or be immediately adjacent an interior wall 175 of the projection body. Thus, the fluid diverter can bifurcate and/or substantially bifurcate at least a portion of the interior 280 of the projection member 170. This can prevent or minimize fluid flow past the fluid diverter, forcing all or the majority of fluid that has been diverted to flow over the upper tip 48 of the fluid diverter. This can provide for a more complete flushing of the needleless connector.

In some embodiments, the fluid diverter can bifurcate and/or substantially bifurcate at least about one third of the height $h_3$ of the interior of the projection (illustrated in FIGS. 16A and 17A). In some embodiments, the diverter can bifurcate and/or substantially bifurcate at least about one half of the height $h_3$. In some embodiments, the diverter can bifurcate and/or substantially bifurcate at least about two thirds of the height $h_3$. In some embodiments, the diverter can bifurcate and/or substantially bifurcate at least about three quarters of the height $h_3$. In some embodiments, the diverter can bifurcate and/or substantially bifurcate at least about seven eighths of the height $h_3$.

Similarly, the amount of bifurcation or substantial bifurcation can be described with respect to the height $h_7$ of the shoulder or collar 132 (illustrated in FIGS. 16A and 17A). In some embodiments the diverter 42 can bifurcate and/or substantially bifurcate at least about one half of the height $h_7$. In some embodiments the diverter 42 can bifurcate and/or substantially bifurcate at least about one half of the height $h_7$. In some embodiments the diverter 42 can bifurcate and/or substantially bifurcate at least about 60 percent of the height $h_7$. In some embodiments the diverter 42 can bifurcate and/or substantially bifurcate at least about 70 percent of the height $h_7$. In some embodiments the diverter 42 can bifurcate and/or substantially bifurcate at least about 80 percent of the height $h_7$. In some embodiments the diverter 42 can bifurcate and/or substantially bifurcate at least about 90 percent of the height $h_7$. In some embodiments the diverter 42 can bifurcate and/or substantially bifurcate at least about 95 percent of the height $h_7$. In some embodiments the entire height $h_7$ of the shoulder or collar can be bifurcated or substantially bifurcated, and in some embodiments bifurcation can extend distal to the shoulder or collar 132.

In some embodiments, a first part of the fluid diverter can bifurcate and/or substantially bifurcate a section of the interior 280 of the projection member 170, and a second part of the fluid diverter can be far enough removed from a wall defining the interior such that the second part does not bifurcate and/or substantially bifurcate the interior. Such embodiments can allow for flexibility in configuring a connector to provide desired flushing characteristics and have a desired priming volume. In some embodiments, the proximal about 50 percent of the fluid diverter can bifurcate and/or substantially bifurcate the interior 280 of the projection member 170. In some embodiments, the proximal about 60 percent of the fluid diverter can bifurcate and/or substantially bifurcate the interior 280. In some embodiments, the proximal about 70 percent of the fluid diverter can bifurcate and/or substantially bifurcate the interior 280. In some embodiments, the proximal about 80 percent of the fluid diverter can bifurcate and/or substantially bifurcate the interior 280. In some embodiments, the proximal about 90 percent of the fluid diverter can bifurcate and/or substantially bifurcate the interior 280. In some embodiments, the proximal about 95 percent of the fluid diverter can bifurcate and/or substantially bifurcate the interior 280. In some embodiments, the proximal about 98 percent of the fluid diverter can bifurcate and/or substantially bifurcate the interior 280.

Figure 23:
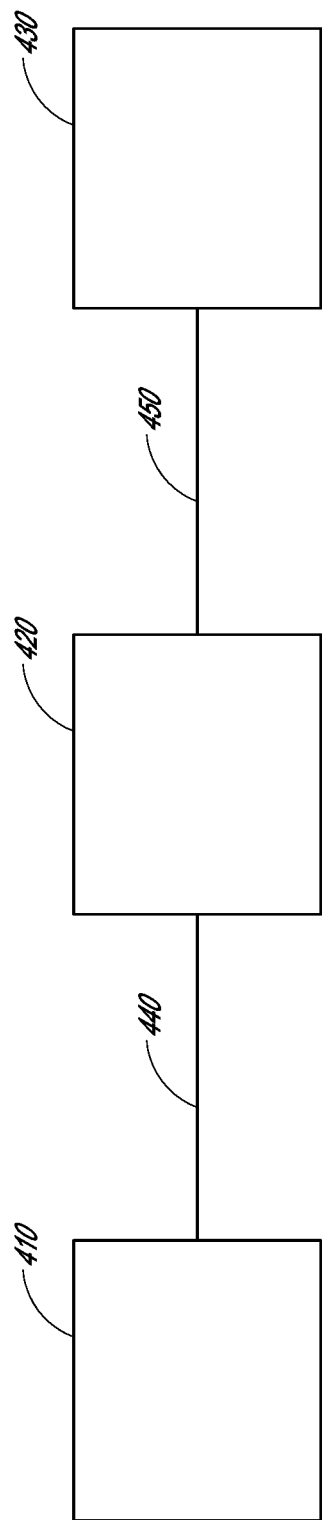
FIG. 23 is a block diagram of a system using a medical connector.

The embodiments of access ports and connectors described herein can be used in a variety of systems. FIG. 23 illustrates a block diagram of one possible system configuration. A medical connector 420 can connect to a patient 430 or other fluid source via a line 450. The medical connector can encompass any of the connector embodiments described herein. For example, in some embodiments the medical connector can be a three-port stopcock with a needleless connector attached to or formed with one port. In some embodiments, the medical connector can be an embodiment of a needleless connector described herein that is not on a stopcock but has a first end attached to line 450 and a second end attached to line 440.

Line 440 can connect the medical connector 420 to a medical instrument 410. The medical instrument can be a medication distribution module, such as an IV bag; it can be a measurement device or system, such as a pressure monitor; or it can be any device or combination of devices used as part of a medical procedure or practice that can connect to a patient.

Figure 24:
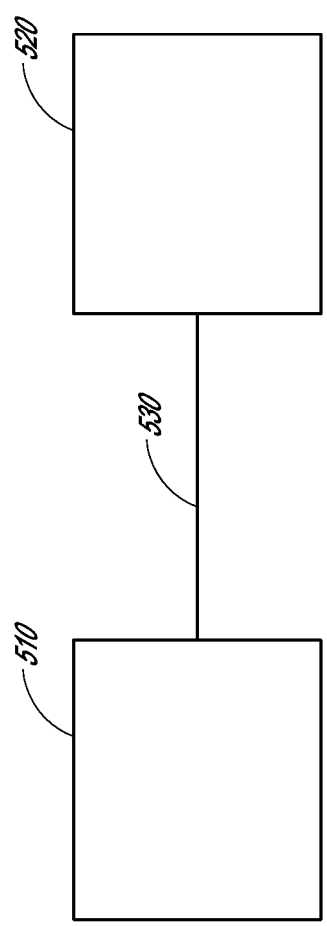
FIG. 24 is a block diagram of a system using a medical connector.

FIG. 24 illustrates a block diagram of a system configuration where a needleless access port 510 connects via line 530 to a patient 520. The needleless access port can be an embodiment of a needleless connector described herein, whether connected to a stopcock or not. The access port can have one end attached to the line 530, and a second end configured to connect to a medical implement. As described above, the connections to the access port can conform with any ANSI standard, or in some embodiments can be nonstandard.

Figure 25:
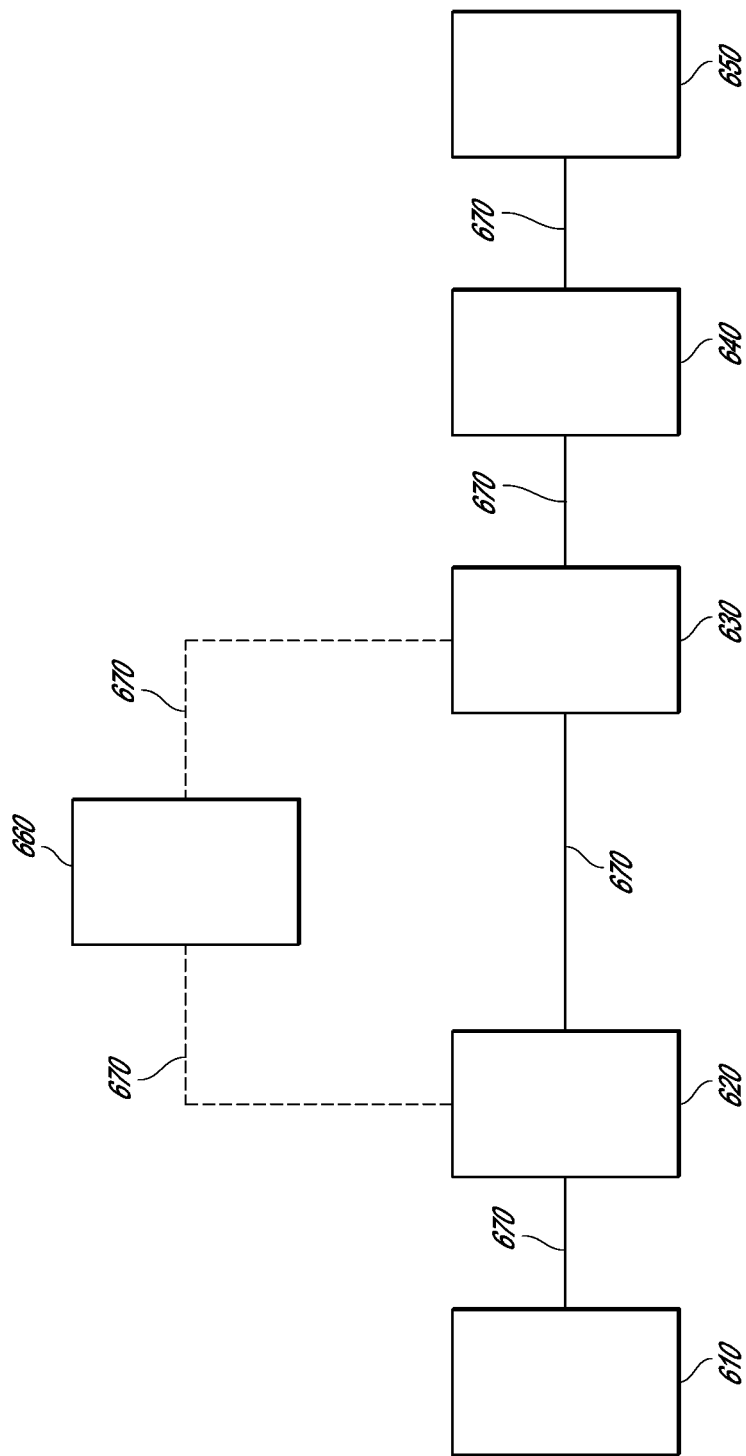
FIG. 25 is a block diagram of one embodiment of a system using a medical connector.

FIG. 25 illustrates a block diagram of two embodiments of a medical fluid flow system. In a first embodiment, a fluid flow line 670 can connect a patient 610 with a stopcock with needleless connector 620 over a fluid diverter, such as the various connectors and stopcocks described herein. The stopcock and needleless connector can connect to a plunging device 630. In some embodiments a plunging device can attach to the line, such as with an additional stopcock. In some embodiments a plunging device can be inline, such as an inline syringe. An inline syringe can have a channel that allows fluid to flow through it, and it can also have a plunger oriented to draw fluid from the line connected to the stopcock. One example of an inline syringe that can be used is the SafeSet™ blood sampling syringe, produced by ICU Medical.

The syringe 630 can then connect to an on/off device 640 capable of restricting the flow of fluid through the flow line 670, such as a two-way stopcock, a roller clamp, or other device. The on/off device can then connect to a fluid source 650, such as an IV drip, pressure bag, or other source. In an alternative embodiment, as illustrated, an additional on/off device 660 can be positioned between the stopcock with needleless connector 620 and the inline syringe 630. In some embodiments, other system elements can be positioned within the fluid flow system. For example, in some embodiments additional stopcocks can be included within the system to provide additional points of access into the line. In some embodiments, pressure measurement or monitoring systems can be connected to the line. This can include, for example, a Transpac® IV disposable pressure transducer, produced by ICU Medical.

Figure 26:
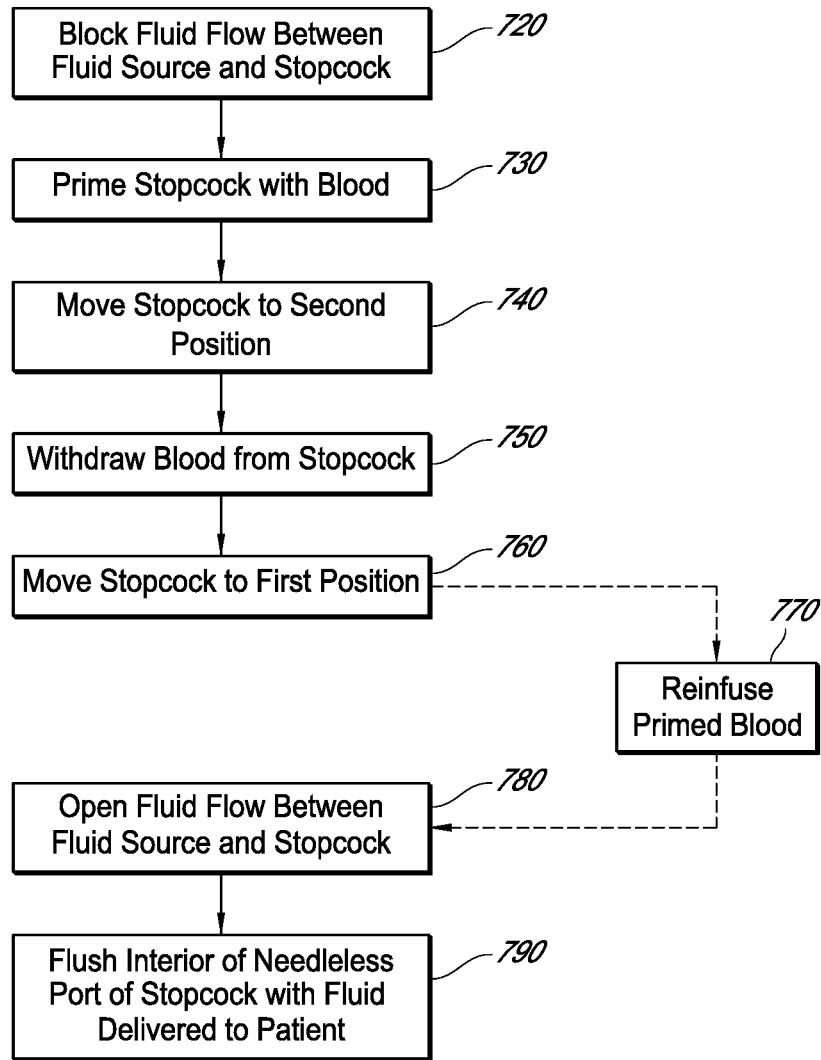
FIG. 26 is a block diagram of one embodiment of a method using a medical connector.

FIG. 26 is a block diagram illustrating a method used with the system illustrated in FIG. 25 to withdraw a sample of blood. The stopcock with a fluid diverter and needleless connector 620 is first primed with whatever fluid is within the fluid source 650 and a line is introduced into or connected to a line into a patient. The stopcock can be in a first position such that all ports are in fluid communication, and the available volume of the stopcock and needleless connector 620 is filled with the fluid of the fluid source as the fluid is delivered to a patient 610. In a first step 720, fluid flow is blocked between the fluid source 650 and the stopcock with needleless connector 620. This can be achieved, for example, by closing an on/off device 640, preferably one that is positioned upstream of the inline syringe 630.

In a second step 730, the stopcock and needleless connector 620 are primed with blood. In some embodiments, this can be achieved with an inline syringe 630, which can be drawn to create a negative pressure, pulling the fluid from the patient into the syringe, or a mixture of blood and fluid into the syringe. In some embodiments this can be done with a syringe attached to the line through other means, such as an additional stopcock. The negative pressure of the syringe will also draw blood from the patient 610 into the stopcock with needleless connector 620, from where a blood sample can be drawn.

In order to obtain a clean and accurate blood sample, the stopcock and needleless connector is preferably filled only with the patient's blood and does not have any residual fluid from the fluid source 650. A number of features described herein can help ensure that the blood in the stopcock with needleless connector is not mixed with fluid. For example, a fluid diverter as described herein can ensure that any fluid in the needleless connector is properly flushed with blood. Additionally, the minimal priming volume of the needleless connector can help ensure that the syringe 630 is able to draw enough fluid to pull blood from the patient all the way through the needleless connector.

Once the stopcock and needleless connector 620 have been filled with blood, in a third step 740, the stopcock can be moved to a second position that blocks fluid communication between the stopcock and the inline syringe. For example, the stopcock can be moved from a first position to a second position such as the position illustrated in FIG. 4B. In some embodiments, a separate on/off device, such as the device 660, can be used to block fluid communication between the stopcock and the syringe. Once communication has been blocked between the syringe and the stopcock, in a fourth step 750 a medical implement can connect to the needleless connector of the stopcock and withdraw a blood sample.

Once a sample has been drawn, in a fifth step 760 a fluid connection can be resumed between the stopcock and the inline connector. This can be done, for example, by returning the stopcock to the first position. In an optional sixth step 770, the syringe can be plunged to reinfuse the drawn fluid and/or blood into the fluid flow system. In a seventh step 780, fluid flow be can reopened between the fluid source 650 and the stopcock with needleless connector 620. In an eighth step 790, the stopcock with needleless connector can be flushed with the fluid from the fluid source, which flushes out any blood remaining in the stopcock with needleless connector. In some embodiments, once fluid flow has been reopened between the fluid source and the stopcock, the stopcock can be flushed with fluid from the fluid source in less than about 5 seconds. In some embodiments, the stopcock can be flushed in less than about 10 seconds.

Figure 27:
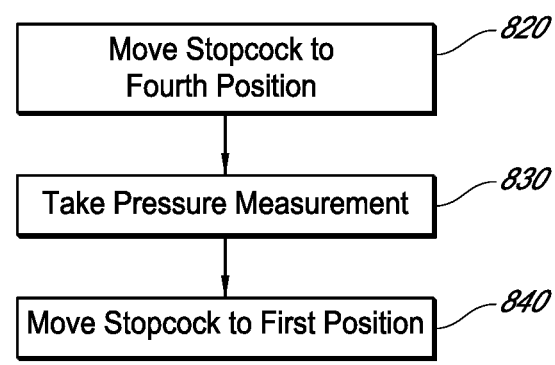
FIG. 27 is a block diagram of one embodiment of a method using a medical connector.

FIG. 27 is a block diagram illustrating a method used with a medical fluid flow system. The method can be used with any fluid flow system that has a stopcock and a pressure measurement device. This can include but is not limited to the system of FIG. 23 and the system of FIG. 25 with a pressure measurement device attached to the fluid flow line. The stopcock can be in a first position with all ports in fluid communication and a fluid can flow through the stopcock to a patient. In a first step 820, the stopcock can be moved from a first position to a fourth position, such as the position illustrated in FIG. 4D. This can create a generally straight flow path through the stopcock, minimizing angles that can affect the pressure measurement. This can also limit contact of the flow path with resilient materials, such as the valve member of the stopcock, which can also affect the pressure measurement. In a second step 830, a pressure measurement is taken. In a third step 840, the stopcock is returned to the first position.

A variety of needleless connectors can be used with the devices and systems described herein. When used with a stopcock with a fluid diverter, the fluid diverter can be sized to fit within the connector as described above. For example, in some embodiments the fluid diverter can have a profile adapted to track the internal profile of the connector. In some embodiments, the fluid diverter can also have a volume designed to partially fill the connector and provide a desired priming volume for use in various systems described herein.

Figure 28:
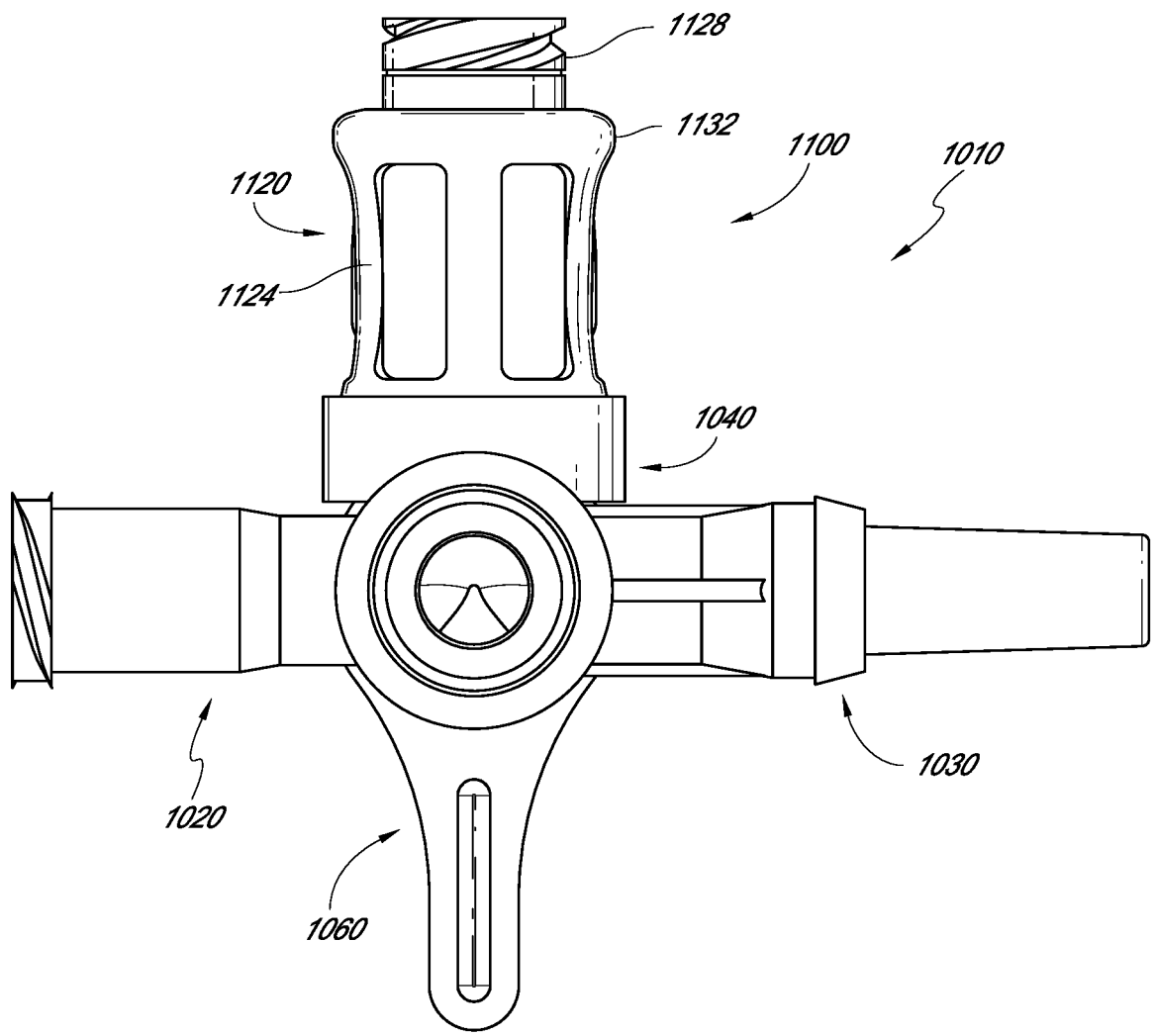
FIG. 28 is a front view of one embodiment of a medical connector positioned on a stopcock.

As an example, FIG. 28 is a side view of a stopcock assembly 1010 with a needleless connector 1100 that can have some features or characteristics similar in some regards to the Swabable Valve available from Halkey-Roberts Corporation of St. Petersburg, Fla. Some features and characteristics of the connector 1100 are described in U.S. Pat. No. 6,651,956, the entirety of which is hereby incorporated by reference herein for all that it discloses. The stopcock can function according to the various embodiments described herein, and elements similar to elements described in such embodiments are understood to be able to function as thus described, whether called out or not. For example, the second port 1030 is illustrated without a luer lock, but in some embodiments it can include a luer lock as described above.

Figure 29A:
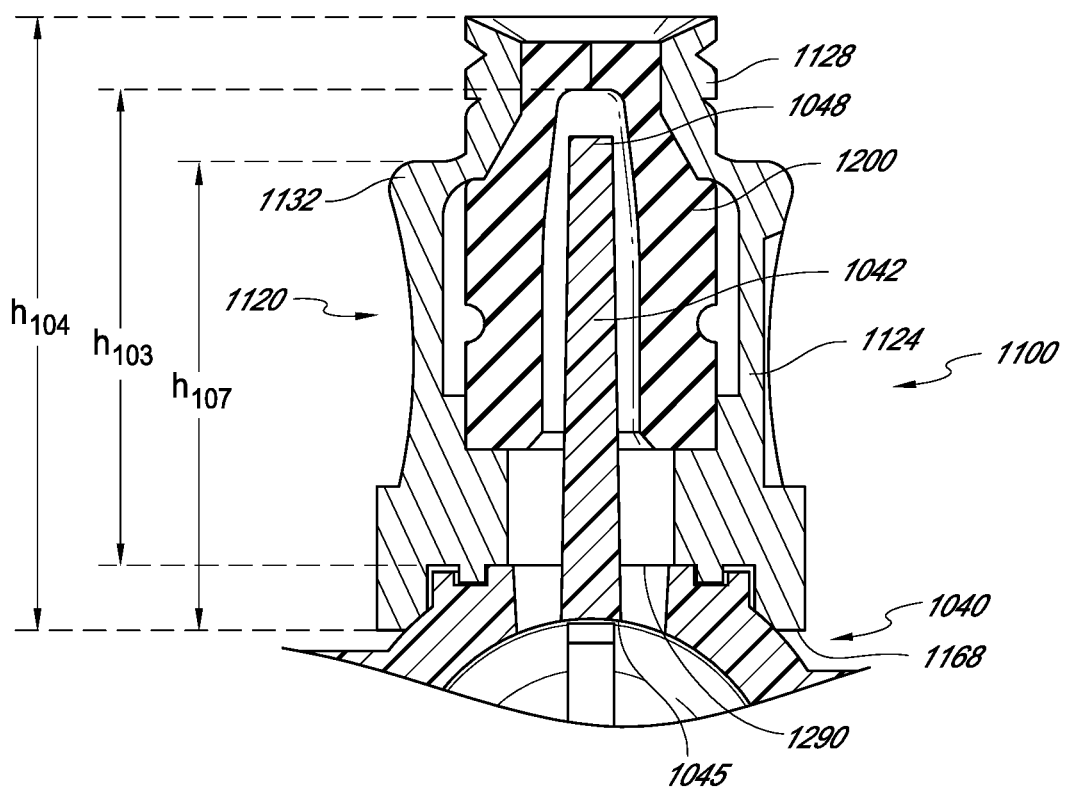
FIG. 29A is a cross section of the medical connector positioned on a stopcock of FIG. 28.
Figure 29B:
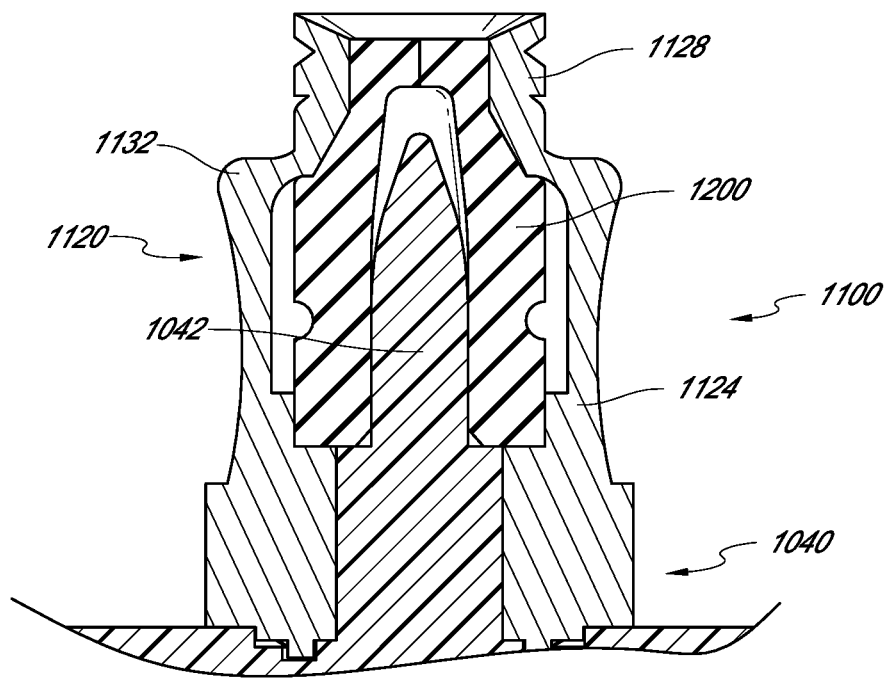
FIG. 29B is a cross section of the medical connector positioned on a stopcock of FIG. 28, rotated approximately 90 degrees from the cross section of FIG. 29A.

FIG. 29A is a sectional view of the connector 1100 shown in FIG. 28, and FIG. 29B is a sectional view rotated approximately 90 degrees from the view of FIG. 29A. In some embodiments, the connector 1100 can include a body member 1120 with a lower or proximal portion 1124 and an upper or distal portion 1128. The body can also include a shoulder 1132. The connector can further include a valve member 1200. As described above, the needleless connector can be positioned on a port 1040 of a stopcock with a fluid diverter 1042 that extends into the connector.

The fluid diverter 1042 can be positioned according to any of the various embodiments described herein. As an example, the connector 1100 can have a height $h_{104}$, which can be measured from a most proximal surface 1168 of the connector to a top or distal most surface of the connector. As a further example, the fluid diverter 1042 can direct fluid and/or the fluid diverter can extend into the distal about two thirds of the height $h_{104}$ of the connector 1100. In some embodiments, the fluid diverter directs fluid and/or the fluid diverter 1042 extends a substantial distance into the connector 1100. In some embodiments, a substantial distance can be any distance identified below. In some embodiments, the fluid diverter 1042 directs fluid and/or the fluid diverter 1042 extends into the distal about one half of the height $h_{104}$ of the connector. In some embodiments, the fluid diverter directs fluid and/or the fluid diverter 1042 extends into the distal about one third of the height $h_{104}$ of the connector. In some embodiments, the fluid diverter directs fluid and/or the fluid diverter 1042 extends into the distal about one quarter of the height $h_{104}$ of the connector. In some embodiments, the fluid diverter directs fluid and/or the fluid diverter 1042 extends into the distal about three sixteenths of the height $h_{104}$ of the connector. In some embodiments, the fluid diverter directs fluid and/or the fluid diverter 1042 extends into the distal about one eighth of the height $h_{104}$ of the connector. In some embodiments, the fluid diverter directs fluid and/or the fluid diverter 1042 extends into the distal about one sixteenth of the height $h_{104}$ of the connector.

Similarly, the connector 1100 can have a shoulder height $h_{107}$ measured from the most proximal surface 1168 of the connector to the shoulder 1132. In some embodiments, as illustrated, a distal tip 1048 of the fluid diverter 1042 can extend distal to the shoulder 1132. In some embodiments, the distal tip can be at or proximal to the shoulder. In some embodiments, the fluid diverter can direct fluid into and/or extend into the distal about two thirds of the shoulder height $h_{107}$. In some embodiments, the fluid diverter can direct fluid into and/or extend into the distal about one half of the shoulder height $h_{107}$. In some embodiments, the fluid diverter can direct fluid into and/or extend into the distal about one third of the shoulder height $h_{107}$. In some embodiments, the fluid diverter can direct fluid into and/or extend into the distal about one quarter of the shoulder height $h_{107}$. In some embodiments, the fluid diverter can direct fluid into and/or extend into the distal about three sixteenths of the shoulder height $h_{107}$. In some embodiments, the fluid diverter can direct fluid into and/or extend into the distal about one eighth of the shoulder height $h_{107}$. In some embodiments, the fluid diverter can direct fluid into and/or extend into the distal about one sixteenth of the shoulder height $h_{107}$. In some embodiments, as illustrated, the distal tip 1048 of the fluid diverter 1042 can extend beyond the shoulder height.

The fluid diverter 1042 can also be sized according to any of the various embodiments described herein. Thus, for example, the diverter can be sized such that the connector 1100 has a desired available volume that receives fluid when flushed. This can be achieved by adjusting the width of the diverter in the plane of FIG. 29A, adjusting the width in the plane of FIG. 29B, and/or by adjusting the height of the diverter. In some embodiments, the volume of available space that receives fluid when flushed can be greater than or equal to approximately 0.005 mL and/or less than or equal to approximately 0.03 mL. In some embodiments, the available volume can be greater than or equal to approximately 0.01 mL and/or less than or equal to approximately 0.02 mL. In some embodiments, the available volume can be greater than or equal to approximately 0.013 mL and/or less than or equal to approximately 0.017 mL. In some embodiments, the available volume can be approximately 0.015 mL.

As a further example, the diverter 1042 can be configured to bifurcate and/or substantially bifurcate at least a portion of an interior of the connector and/or at least a portion of the valve member 1200. The amount of the connector that is bifurcated or substantially bifurcated can be defined according to various heights as described herein. For example, in some embodiments the diverter can bifurcate and/or substantially bifurcate at least about one half of the height $h_{103}$ of the interior of the connector, which can be measured from an opening 1290 at the bottom of the connector to the distal most surface of the interior of the valve member 1200. In some embodiments the diverter 1042 can bifurcate and/or substantially bifurcate at least about two thirds of the height $h_{103}$. In some embodiments the diverter 1042 can bifurcate and/or substantially bifurcate at least about three quarters of the height $h_{103}$. In some embodiments the diverter 1042 can bifurcate and/or substantially bifurcate at least about seven eighths of the height $h_{103}$.

Similarly, the diverter 1042 can bifurcate and/or substantially bifurcate at least about one half of the height $h_{107}$. In some embodiments, the diverter 1042 can bifurcate and/or substantially bifurcate at least about 60 percent of the height $h_{107}$. In some embodiments, the diverter 1042 can bifurcate and/or substantially bifurcate at least about 70 percent of the height $h_{107}$. In some embodiments, the diverter 1042 can bifurcate and/or substantially bifurcate at least about 80 percent of the height $h_{107}$. In some embodiments, the diverter 1042 can bifurcate and/or substantially bifurcate at least about 90 percent of the height $h_{107}$. In some embodiments, the diverter 1042 can bifurcate and/or substantially bifurcate at least about 95 percent of the height $h_{107}$. In some embodiments the entire height of the shoulder or collar can be bifurcated or substantially bifurcated, and in some embodiments bifurcation can extend distal to the shoulder or collar 1132, as illustrated.

Figure 30:
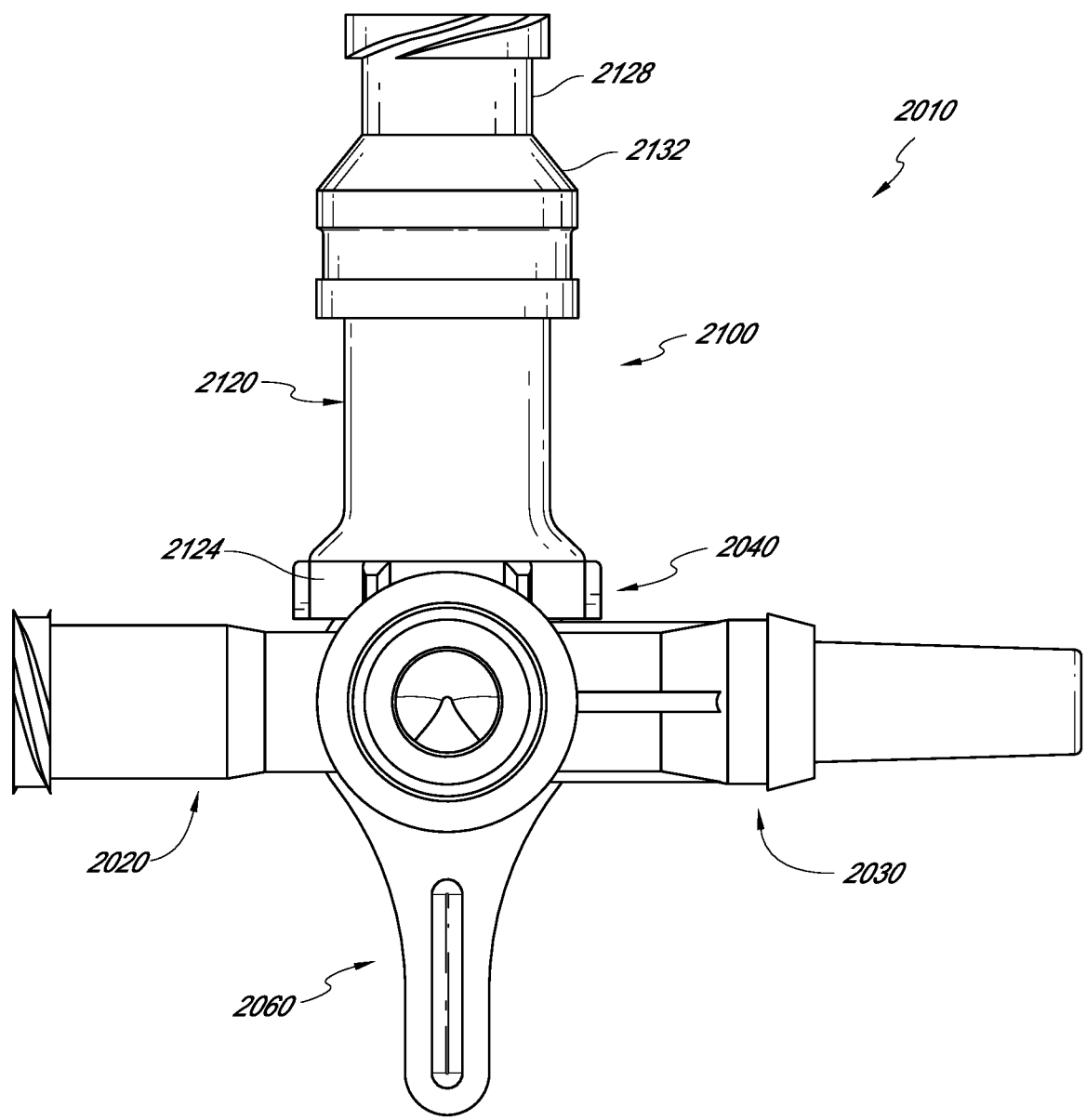
FIG. 30 is a front view of one embodiment of a medical connector positioned on a stopcock.

FIG. 30 is a side view of a stopcock assembly 2010 with a needleless connector 2100 that can have some features or characteristics similar in some regards to the SmartSite™ connector available from Cardinal Health, Inc. of Dublin, Ohio. Some features and characteristics of the connector 2100 are described in U.S. Pat. No. 5,676,346, the entirety of which is hereby incorporated by reference herein for all that it discloses. The stopcock can function according to the various embodiments described herein, and elements similar to elements described in such embodiments are understood to be able to function as thus described, whether called out or not.

Figure 31A:
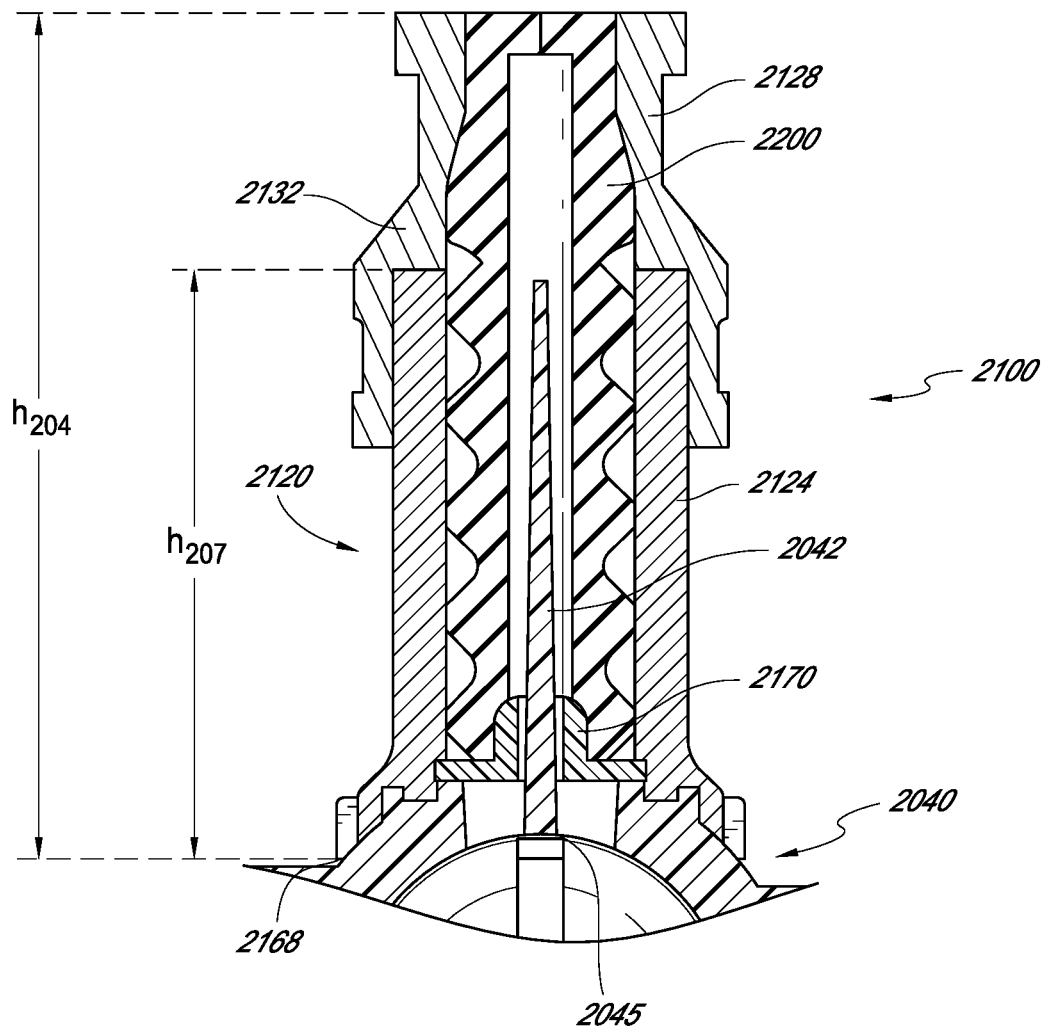
FIG. 31A is a cross section of the medical connector positioned on a stopcock of FIG. 30.
Figure 31B:
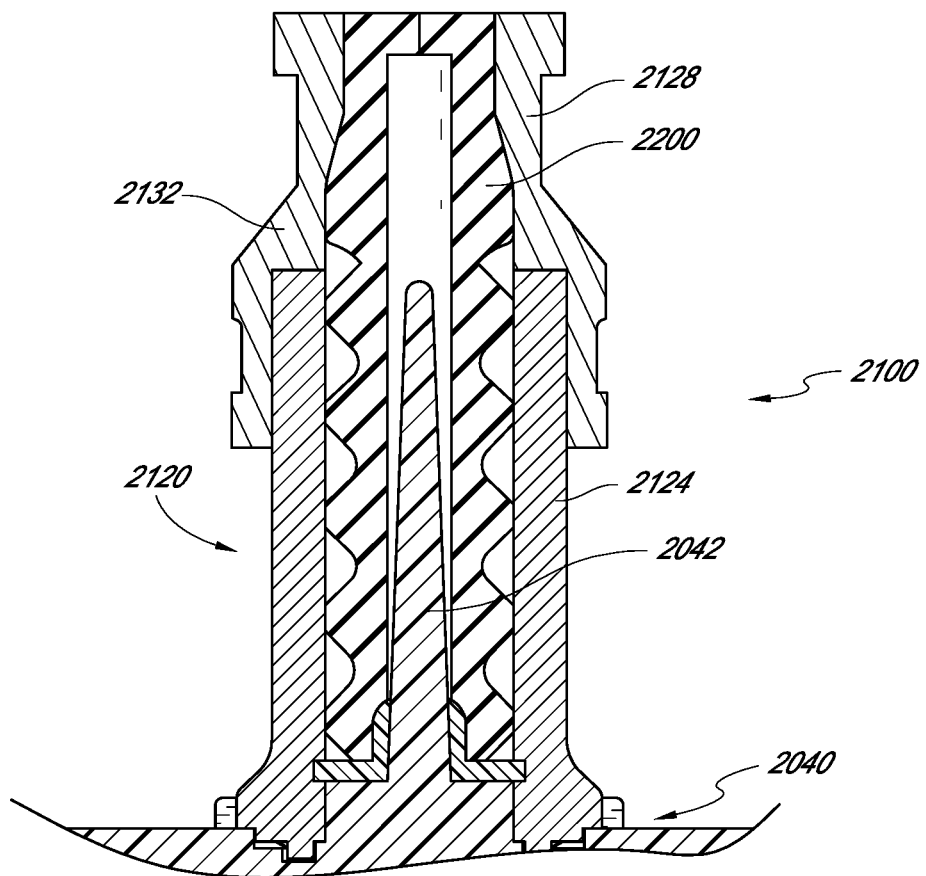
FIG. 31B is a cross section of the medical connector positioned on a stopcock of FIG. 30, rotated approximately 90 degrees from the cross section of FIG. 31A.

FIG. 31A is a sectional view of the connector 2100 shown in FIG. 30, and FIG. 31B is a sectional view rotated approximately 90 degrees from the view of FIG. 31A. In some embodiments, the connector 2100 can include a body 2120 with a lower member 2124, an upper member 2128, and a shoulder 2132. The connector can further include a valve member 2200. In some embodiments the valve member can be positioned over a cannula 2170. As described above, the needleless connector can be positioned on a port 2040 of a stopcock with a fluid diverter 2042 that extends into the connector.

The fluid diverter 2042 can be positioned according to any of the various embodiments described herein. As an example, the connector 2100 can have a height $h_{204}$, which can be measured from a most proximal surface 2168 of the connector to a top or distal most surface of the connector body 2120. The fluid diverter can also be positioned with respect to a shoulder height $h_{207}$, measured from the most proximal surface 2168 of the connector to the shoulder 2132. In some embodiments the fluid diverter 2042 can direct fluid and/or the fluid diverter extends a substantial distance into the connector 2100. In some embodiments, a substantial distance can be any distance identified below. In some embodiments, the fluid diverter 2042 directs fluid and/or the fluid diverter 2042 extends into the distal about two thirds of the height $h_{204}$ of the connector 2100. In some embodiments, the fluid diverter directs fluid and/or the fluid diverter 2042 extends into the distal about one half of the height $h_{204}$ of the connector. In some embodiments, the fluid diverter directs fluid and/or the fluid diverter 2042 extends into the distal about one third of the height $h_{204}$ of the connector. In some embodiments, the fluid diverter directs fluid and/or the fluid diverter 2042 extends into the distal about one quarter of the height $h_{204}$ of the connector. In some embodiments, the fluid diverter directs fluid and/or the fluid diverter 2042 extends into the distal about three sixteenths of the height $h_{204}$ of the connector. In some embodiments, the fluid diverter directs fluid and/or the fluid diverter 2042 extends into the distal about one eighth of the height $h_{204}$ of the connector. In some embodiments, the fluid diverter directs fluid and/or the fluid diverter 2042 extends into the distal about one sixteenth of the height $h_{204}$ of the connector.

As a further example of fluid diverter 2042 being positioned according to various embodiments described herein, in some embodiments, the fluid diverter can direct fluid into and/or extend into the distal about two thirds of the shoulder height $h_{207}$. In some embodiments, the fluid diverter can direct fluid into and/or extend into the distal about one half of the shoulder height $h_{207}$. In some embodiments, the fluid diverter can direct fluid into and/or extend into the distal about one third of the shoulder height $h_{207}$. In some embodiments, the fluid diverter can direct fluid into and/or extend into the distal about one quarter of the shoulder height $h_{207}$. In some embodiments, the fluid diverter can direct fluid into and/or extend into the distal about three sixteenths of the shoulder height $h_{207}$. In some embodiments, the fluid diverter can direct fluid into and/or extend into the distal about one eighth of the shoulder height $h_{207}$. In some embodiments, the fluid diverter can direct fluid into and/or extend into the distal about one sixteenth of the shoulder height $h_{207}$. In some embodiments, the fluid diverter 1042 can extend to approximately the shoulder 2132 or beyond the shoulder.

The fluid diverter 2042 can also be sized according to any of the various embodiments described herein. Thus, for example, the diverter can be sized such that the connector 2100 has a desired available volume that receives fluid when flushed, as described above, such as by adjusting the diverter width in the plane of FIG. 31A, adjusting the diverter width in the plane of FIG. 31B, and/or by adjusting the height of the diverter. In some embodiments, the volume of available space that receives fluid when flushed can be greater than or equal to approximately 0.005 mL and/or less than or equal to approximately 0.03 mL. In some embodiments, the available volume can be greater than or equal to approximately 0.01 mL and/or less than or equal to approximately 0.02 mL. In some embodiments, the available volume can be greater than or equal to approximately 0.013 mL and/or less than or equal to approximately 0.017 mL. In some embodiments, the available volume can be approximately 0.015 mL.

In some embodiments, the diverter 2042 can be configured to bifurcate and/or substantially bifurcate at least a portion of an interior of the connector 2100 and/or at least a portion of the valve member 2200. The amount of the connector that is bifurcated or substantially bifurcated can be defined according to various heights as described herein. For example, in some embodiments the diverter can bifurcate and/or substantially bifurcate at least about one half of the height $h_{204}$ of the connector. In some embodiments the diverter 2042 can bifurcate and/or substantially bifurcate at least about two thirds of the height $h_{204}$ of the connector. In some embodiments the diverter 2042 can bifurcate and/or substantially bifurcate at least about three quarters of the height $h_{204}$ of the connector. In some embodiments the diverter 2042 can bifurcate and/or substantially bifurcate at least about seven eighths of the height $h_{204}$ of the connector.

Similarly, in some embodiments the diverter 2042 can bifurcate and/or substantially bifurcate at least about one half of the height $h_{207}$. In some embodiments, the diverter 2042 can bifurcate and/or substantially bifurcate at least about 60 percent of the height $h_{207}$. In some embodiments, the diverter 2042 can bifurcate and/or substantially bifurcate at least about 70 percent of the height $h_{207}$. In some embodiments, the diverter 2042 can bifurcate and/or substantially bifurcate at least about 80 percent of the height $h_{207}$. In some embodiments, the diverter 2042 can bifurcate and/or substantially bifurcate at least about 90 percent of the height $h_{207}$. In some embodiments, the diverter 2042 can bifurcate and/or substantially bifurcate at least about 95 percent of the height $h_{207}$. In some embodiments the entire height of the shoulder or collar can be bifurcated or substantially bifurcated, and in some embodiments bifurcation can extend distal to the shoulder or collar 2132.

Figure 32:
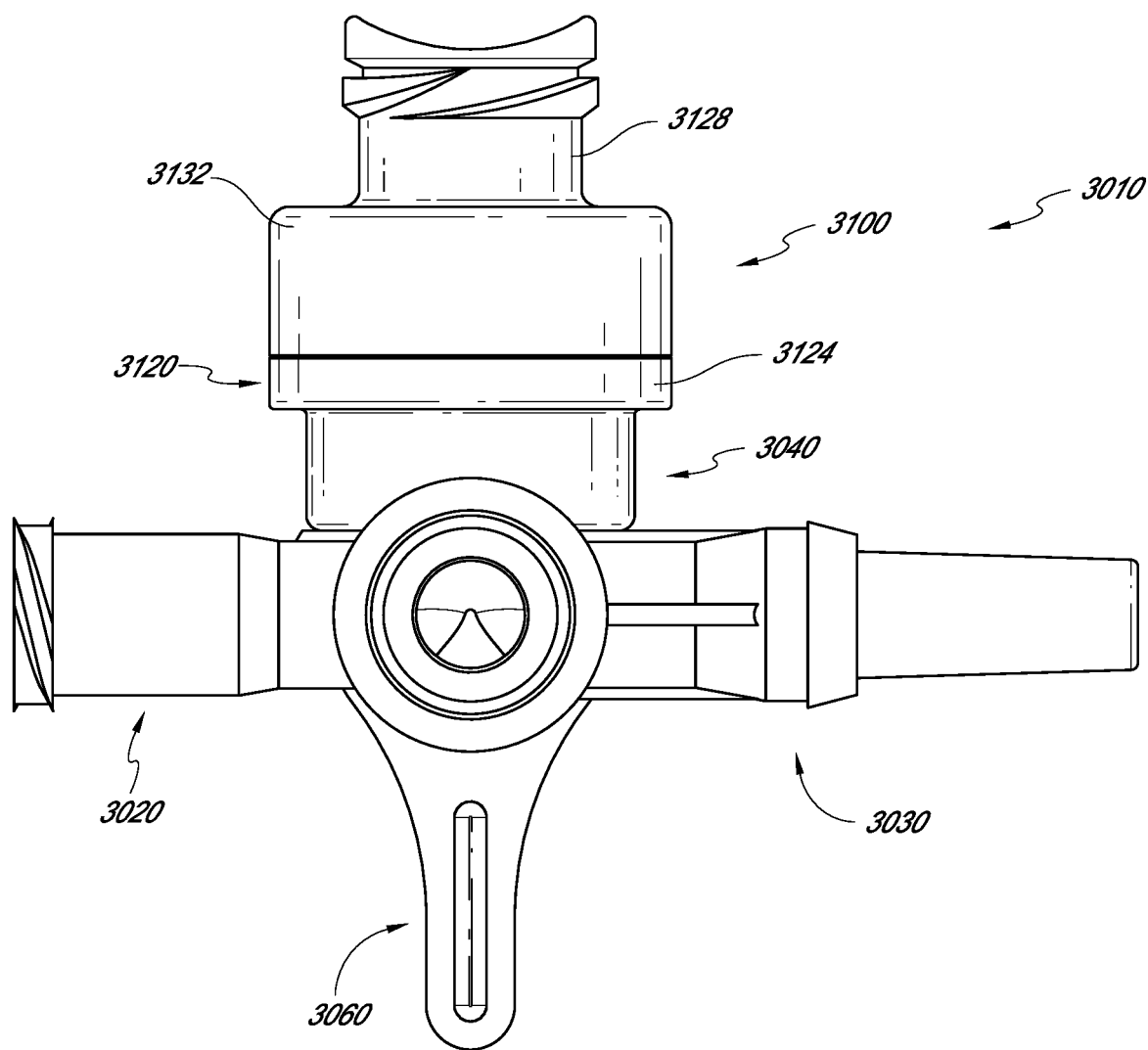
FIG. 32 is a front view of one embodiment of a medical connector positioned on a stopcock.

FIG. 32 is a side view of a stopcock assembly 3010 with a needleless connector 3100 that can have some features or characteristics similar in some regards to the Q-Syte™ connector available from Becton, Dickinson and Company, of Franklin Lakes, N.J. Some features and characteristics of the connector 3100 are described in U.S. Pat. No. 8,366,676, the entirety of which is hereby incorporated by reference herein for all that it discloses. The stopcock can function according to the various embodiments described herein, and elements similar to elements described in such embodiments are understood to be able to function as thus described, whether called out or not.

Figure 33A:
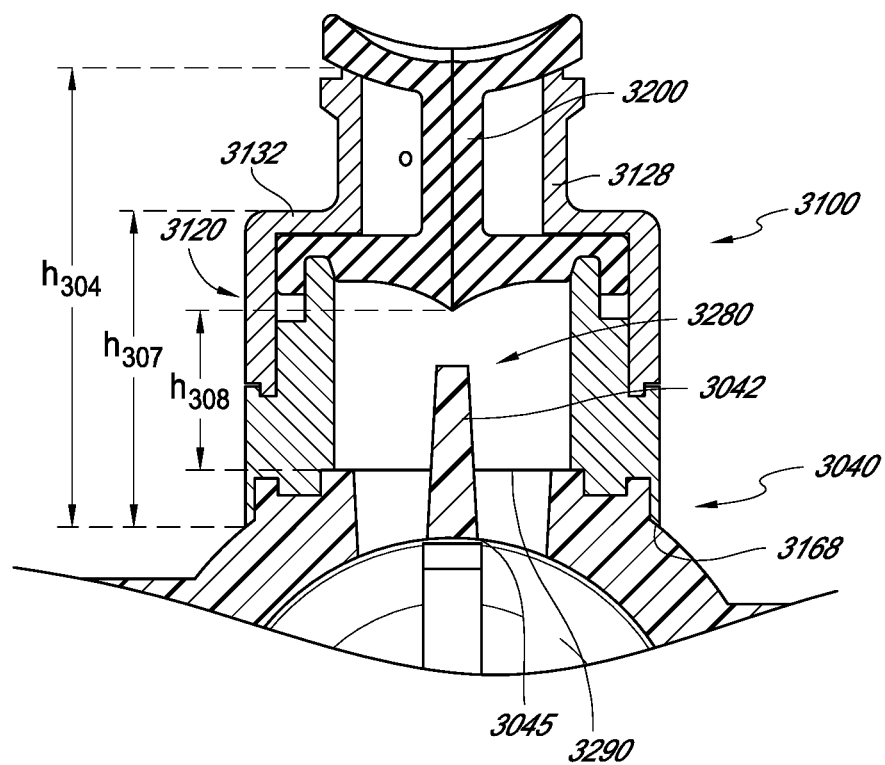
FIG. 33A is a cross section of the medical connector positioned on a stopcock of FIG. 32.
Figure 33B:
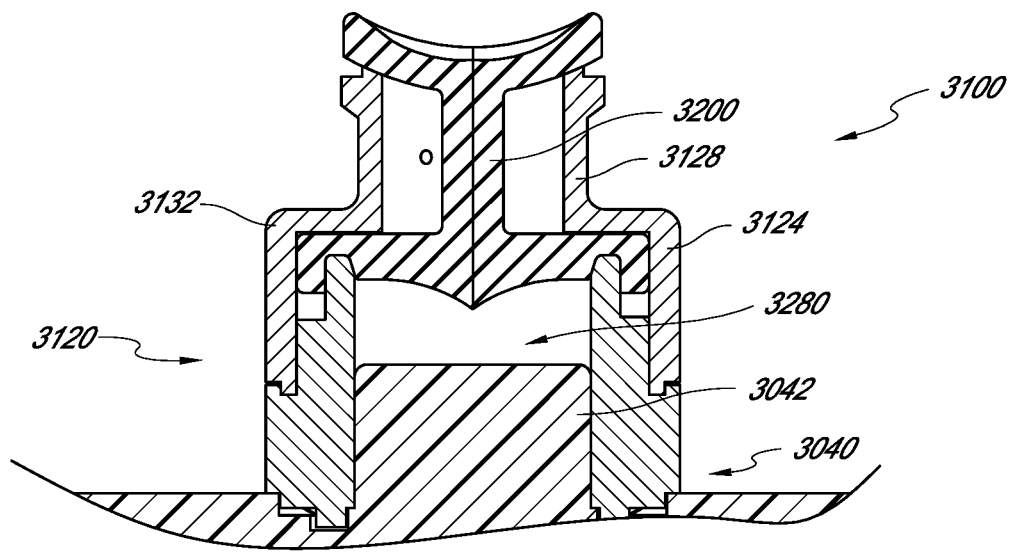
FIG. 33B is a cross section of the medical connector positioned on a stopcock of FIG. 32, rotated approximately 90 degrees from the cross section of FIG. 33A.

FIG. 33A is a sectional view of the connector 3100 shown in FIG. 32, and FIG. 33B is a sectional view rotated approximately 90 degrees from the view of FIG. 33A. In some embodiments, the connector 3100 can include a body member 3120 with a lower or proximal portion 3124 and an upper or distal portion 3128. The body can also include a shoulder 3132. The connector can further include a valve member 3200. As described above, the needleless connector can be positioned on a port 3040 of a stopcock with a fluid diverter 3042 that extends into the connector.

The fluid diverter 3042 can be positioned according to any of the various embodiments described herein. As an example, the connector 3100 can have a height $h_{304}$, which can be measured from a most proximal surface 3168 of the connector to a top or distal most surface of the connector body 3120.

As a further example, the fluid diverter 3042 can direct fluid and/or the fluid diverter extends into the distal about three quarters of the height $h_{304}$ of the connector 3100. In some embodiments, the fluid diverter directs fluid and/or the fluid diverter 3042 extends a substantial distance into the connector 3100. In some embodiments, a substantial distance can be any distance identified below. In some embodiments, the fluid diverter 3042 directs fluid and/or the fluid diverter 3042 extends into the distal about two thirds of the height $h_{304}$ of the connector. In some embodiments, the fluid diverter directs fluid and/or the fluid diverter 3042 extends into the distal about one half of the height $h_{304}$ of the connector. In some embodiments, the fluid diverter directs fluid and/or the fluid diverter 3042 extends into the distal about one third of the height $h_{304}$ of the connector.

The fluid diverter 3042 can be defined with respect to other heights, such as a shoulder height $h_{307}$, measured from a most proximal surface 3168 of the connector to the top of a shoulder 3132. In some embodiments, as illustrated, where the diverter does not extend all the way to or into the valve member, the fluid diverter can also be defined with respect to a valve height $h_{308}$. The valve height $h_{308}$ can be defined from an opening 3290 at the bottom of the connector to a most proximal surface of the valve member 3200 or to a most proximal surface of the valve member along a longitudinal axis of the connector 3100. In the illustrated embodiment these two locations are the same, though in some embodiments they are not.

In some embodiments, the diverter can be sized with respect to the shoulder height $h_{307}$ as described according to various embodiments described above. In some embodiments, the fluid diverter can be configured to direct fluid and/or the fluid diverter extends into the distal about fifty percent of the height $h_{308}$. In some embodiments, the fluid diverter can direct fluid and/or can extend into the distal about 75 percent of the valve height $h_{308}$. In some embodiments, the fluid diverter can direct fluid and/or can extend into the distal about 80 percent of the valve height $h_{308}$. In some embodiments, the fluid diverter can direct fluid and/or can extend into the distal about 85 percent of the valve height $h_{308}$. In some embodiments, the fluid diverter can direct fluid and/or can extend into the distal about 90 percent of the valve height $h_{308}$. In some embodiments, the fluid diverter can direct fluid and/or can extend into the distal about 95 percent of the valve height $h_{308}$.

The fluid diverter 3042 can also be sized according to any of the various embodiments described herein. Thus, for example, the diverter can be sized such that the connector 3100 has a desired available volume that receives fluid when flushed. For example, this can be done by adjusting the width of the diverter in the plane of FIG. 33A, adjusting the width of the diverter in the plane of FIG. 33B, and/or adjusting the height of the diverter. In some embodiments, the volume of available space that receives fluid when flushed can be greater than or equal to approximately 0.005 mL and/or less than or equal to approximately 0.03 mL. In some embodiments, the volume of available space that receives fluid when flushed can be greater than or equal to approximately 0.01 mL and/or less than or equal to approximately 0.02 mL. In some embodiments, the volume of available space that receives fluid when flushed can be greater than or equal to approximately 0.013 mL and/or less than or equal to approximately 0.017 mL. In some embodiments, the volume of available space that receives fluid when flushed can be approximately 0.015 mL.

In some embodiments the diverter can bifurcate and/or substantially bifurcate at least about one half of the height $h_{307}$. In some embodiments the diverter 3042 can bifurcate and/or substantially bifurcate at least about two thirds of the height $h_{307}$. In some embodiments the diverter 3042 can bifurcate and/or substantially bifurcate at least about three quarters of the height $h_{307}$. In some embodiments the diverter 3042 can bifurcate and/or substantially bifurcate at least about seven eighths of the height $h_{307}$.

Similarly, in some embodiments the diverter 3042 can bifurcate and/or substantially bifurcate at least about two thirds of the height $h_{308}$. In some embodiments, the diverter 3042 can bifurcate and/or substantially bifurcate at least about 50 percent of the height $h_{308}$. In some embodiments, the diverter 3042 can bifurcate and/or substantially bifurcate at least about 60 percent of the height $h_{308}$. In some embodiments, the diverter 3042 can bifurcate and/or substantially bifurcate at least about 70 percent of the height $h_{308}$. In some embodiments, the diverter 3042 can bifurcate and/or substantially bifurcate at least about 80 percent of the height $h_{308}$. In some embodiments, the diverter 3042 can bifurcate and/or substantially bifurcate at least about 90 percent of the height $h_{308}$. In some embodiments, the diverter 3042 can bifurcate and/or substantially bifurcate at least about 95 percent of the height $h_{308}$.

In some embodiments, the diverter 3042 can be configured to bifurcate and/or substantially bifurcate at least a portion of the interior space 3280 of the connector 3100. In some embodiments, in order to bifurcate and/or substantially bifurcate a portion of the interior space, the diverter 3042 can be wider than it is tall. In some embodiments, the entire height of the diverter can bifurcate and/or substantially bifurcate the interior space. In some embodiments, as described above, the proximal about 50 percent of the fluid diverter can bifurcate and/or substantially bifurcate the interior space 3280. In some embodiments, the proximal about 60 percent of the fluid diverter can bifurcate and/or substantially bifurcate the interior space 3280. In some embodiments, the proximal about 70 percent of the fluid diverter can bifurcate and/or substantially bifurcate the interior space 3280. In some embodiments, the proximal about 80 percent of the fluid diverter can bifurcate and/or substantially bifurcate the interior space 3280. In some embodiments, the proximal about 90 percent of the fluid diverter can bifurcate and/or substantially bifurcate the interior space 3280. In some embodiments, the proximal about 95 percent of the fluid diverter can bifurcate and/or substantially bifurcate the interior space 3280. In some embodiments, the proximal about 98 percent of the fluid diverter can bifurcate and/or substantially bifurcate the interior space 3280.

Figure 34:
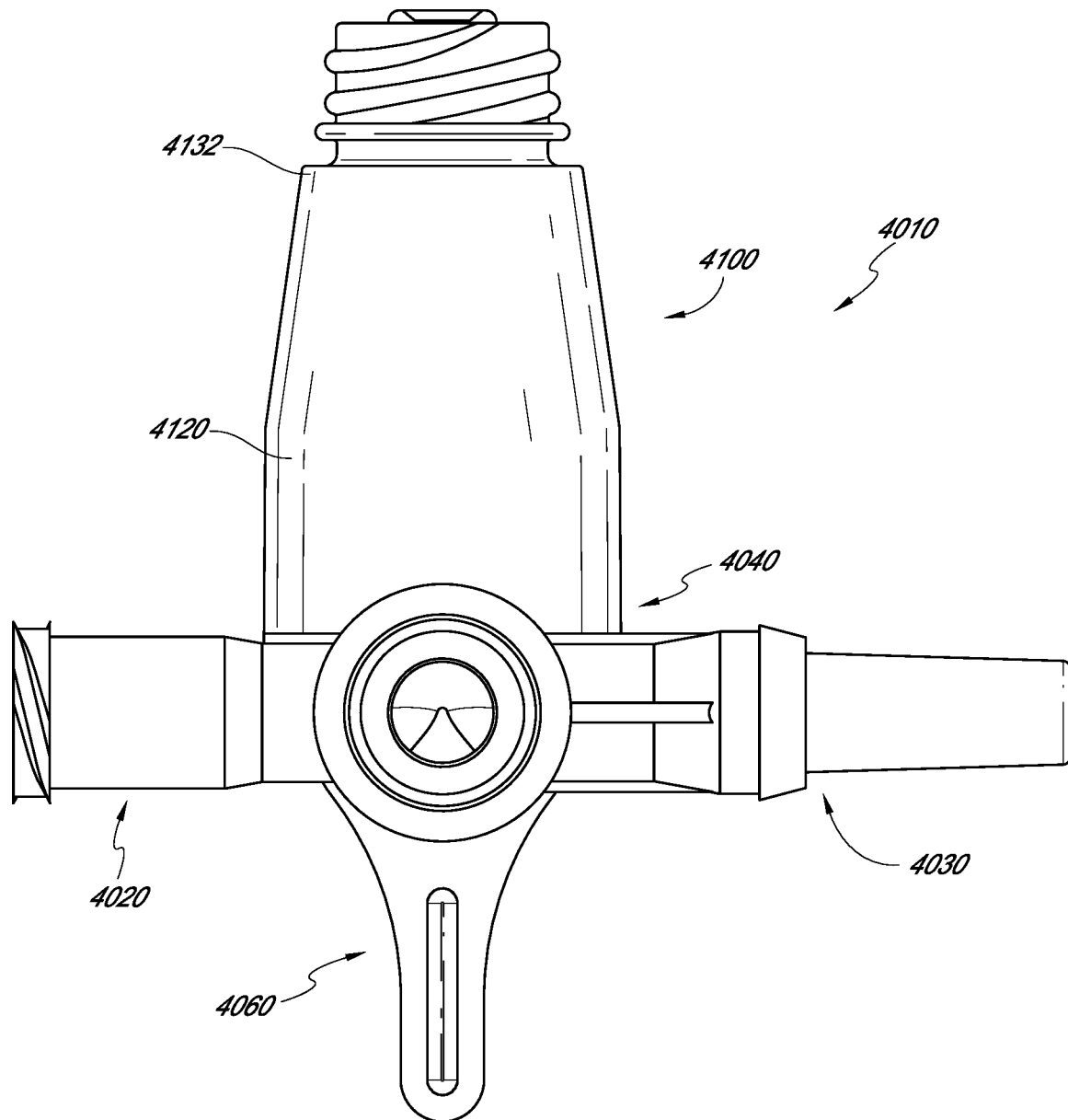
FIG. 34 is a front view of one embodiment of a medical connector positioned on a stopcock.

FIG. 34 is a side view of a stopcock assembly 4010 with a needleless connector 4100 that can have some features or characteristics similar in some regards to the Posiflow™ connector available from Becton, Dickinson and Company, of Franklin Lakes, N.J. Some features and characteristics of the connector 4100 are described in U.S. Pat. No. 6,152,900, the entirety of which is hereby incorporated by reference herein for all that it discloses. The stopcock can function according to the various embodiments described herein, and elements similar to elements described in such embodiments are understood to be able to function as thus described, whether called out or not.

Figure 35A:
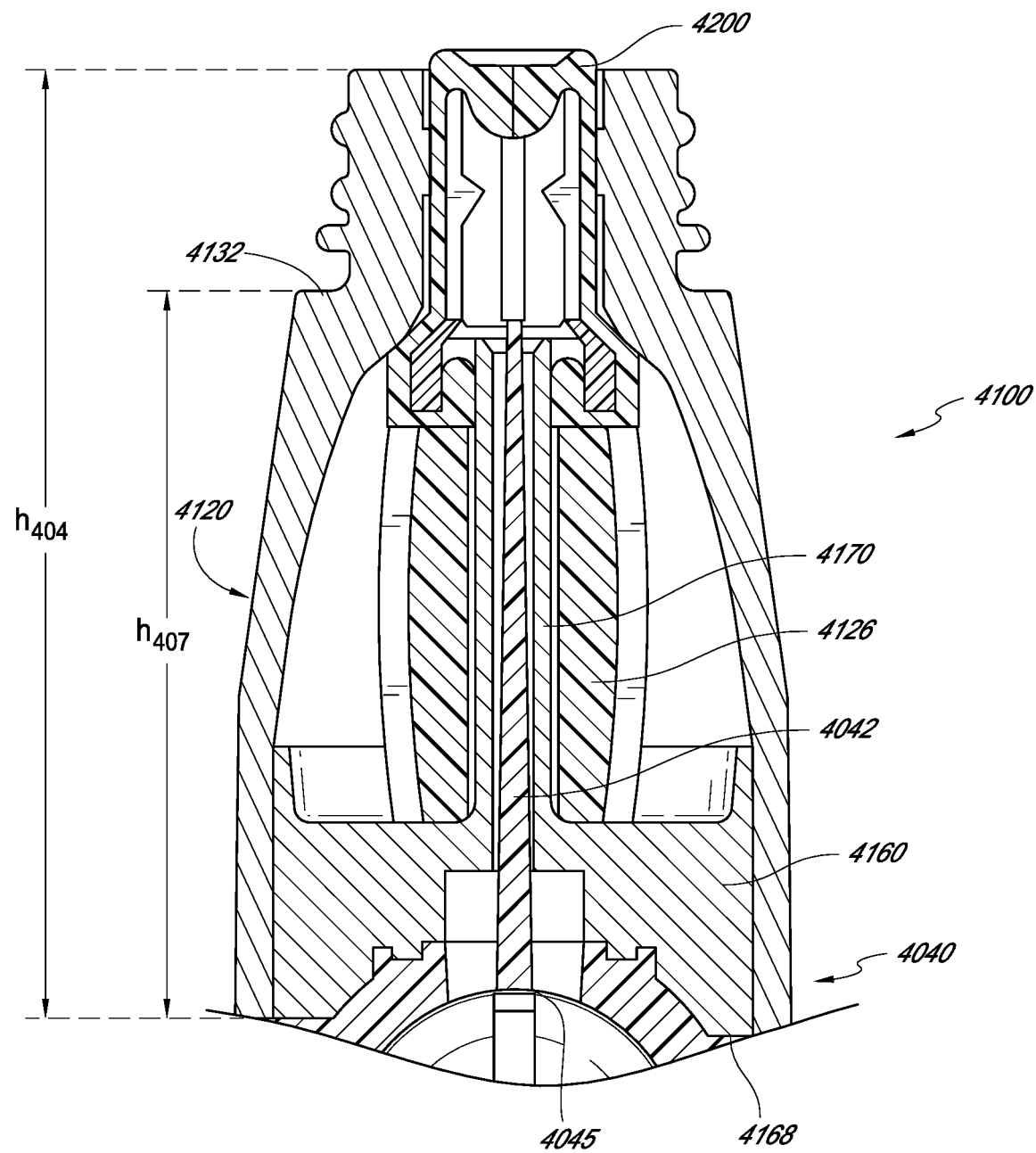
FIG. 35A is a cross section of the medical connector positioned on a stopcock of FIG. 34.
Figure 35B:
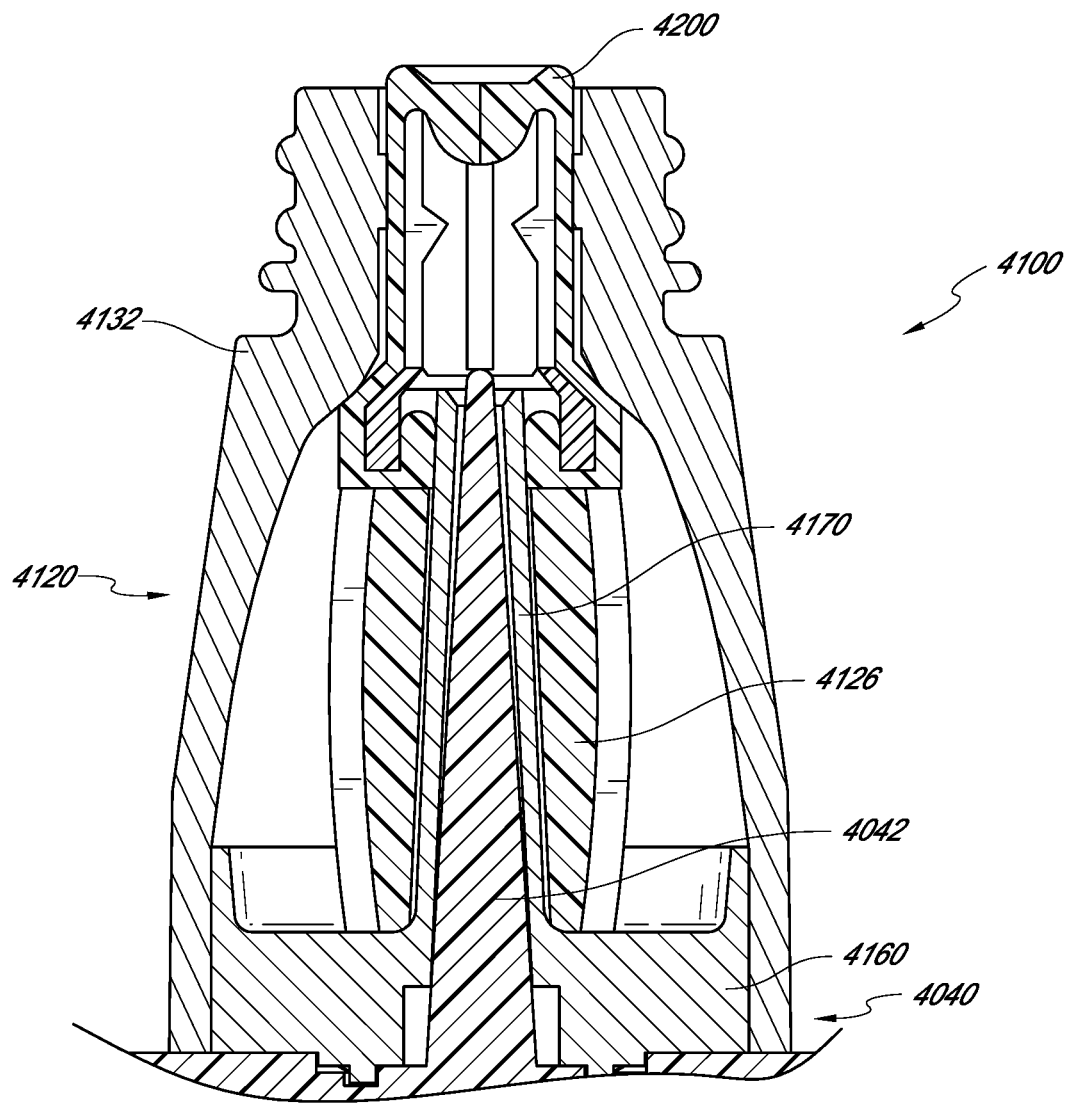
FIG. 35B is a cross section of the medical connector positioned on a stopcock of FIG. 34, rotated approximately 90 degrees from the cross section of FIG. 35A.

FIG. 35A is a sectional view of the connector 4100 shown in FIG. 34, and FIG. 35B is a sectional view rotated approximately 90 degrees from the view of FIG. 35A. In some embodiments, the connector 4100 can include a body member 4120 with a shoulder 4132. The connector can also include a base section 4160 with an internal projection member 4170, a resilient member 4126, and a valve member 4200. As described above, the needleless connector can be positioned on a port 4040 of a stopcock with a fluid diverter 4042 that extends into the connector. In some embodiments, as illustrated, the projection member 4170 can have an open distal end. In some embodiments, the fluid diverter can extend to a position distal to the internal projection member 4170.

The fluid diverter 4042 can be positioned according to any of the various embodiments described herein. Thus, it can be positioned as described above with respect to a connector height $h_{404}$, measured from a most proximal surface 4168 of the connector to a top or distal most surface of the connector body 4120. For example, in some embodiments the fluid diverter 4042 can direct fluid and/or the fluid diverter extends a substantial distance into the connector 4100. FIG. 35A illustrates one embodiment where a substantial distance is further into the connector than a base section 4160 extends from the connecting portion. In some embodiments, a substantial distance can be any distance identified below. In some embodiments, the fluid diverter 4042 directs fluid and/or the fluid diverter 4042 extends into the distal about two thirds of the height $h_{404}$ of the connector 4100. In some embodiments, the fluid diverter directs fluid and/or the fluid diverter 4042 extends into the distal about one half of the height $h_{404}$ of the connector. In some embodiments, the fluid diverter directs fluid and/or the fluid diverter 4042 extends into the distal about one third of the height $h_{404}$ of the connector. In some embodiments, the fluid diverter directs fluid and/or the fluid diverter 4042 extends into the distal about one quarter of the height $h_{404}$ of the connector. In some embodiments, the fluid diverter directs fluid and/or the fluid diverter 4042 extends into the distal about three sixteenths of the height $h_{404}$ of the connector. In some embodiments, the fluid diverter directs fluid and/or the fluid diverter 4042 extends into the distal about one eighth of the height $h_{404}$ of the connector. In some embodiments, the fluid diverter directs fluid and/or the fluid diverter 4042 extends into the distal about one sixteenth of the height $h_{404}$ of the connector.

The fluid diverter can also be positioned as described above with respect to a shoulder height $h_{407}$, measured from a most proximal surface 4168 of the connector to a shoulder 4132. Thus, for example, in some embodiments, the fluid diverter 4042 can direct fluid into and/or extend into the distal about two thirds of the shoulder height $h_{407}$. In some embodiments, the fluid diverter can direct fluid into and/or extend into the distal about one half of the shoulder height $h_{407}$. In some embodiments, the fluid diverter can direct fluid into and/or extend into the distal about one third of the shoulder height $h_{407}$. In some embodiments, the fluid diverter can direct fluid into and/or extend into the distal about one quarter of the shoulder height $h_{407}$. In some embodiments, the fluid diverter can direct fluid into and/or extend into the distal about three sixteenths of the shoulder height $h_{407}$. In some embodiments, the fluid diverter can direct fluid into and/or extend into the distal about one eighth of the shoulder height $h_{407}$. In some embodiments, the fluid diverter can direct fluid into and/or extend into the distal about one sixteenth of the shoulder height $h_{407}$. In some embodiments, the fluid diverter 4042 can extend to approximately the shoulder 4132 or beyond the shoulder.

The fluid diverter 4042 can also be sized according to any of the various embodiments described herein, to displace a desired volume and/or to bifurcate and/or substantially bifurcate a desired portion of the projection member 4170. Thus, for example, the diverter can be sized such that the connector 4100 has a desired available volume that receives fluid when flushed. For example, this can be done by adjusting the width of the diverter in the plane of FIG. 35A, adjusting the width of the diverter in the plane of FIG. 35B, and/or adjusting the height of the diverter. In some embodiments, the volume of available space that receives fluid when flushed can be greater than or equal to approximately 0.005 mL and/or less than or equal to approximately 0.03 mL. In some embodiments, the volume of available space that receives fluid when flushed can be greater than or equal to approximately 0.01 mL and/or less than or equal to approximately 0.02 mL. In some embodiments, the volume of available space that receives fluid when flushed can be greater than or equal to approximately 0.013 mL and/or less than or equal to approximately 0.017 mL. In some embodiments, the volume of available space that receives fluid when flushed can be approximately 0.015 mL.

In some embodiments, the diverter 4042 can be configured to bifurcate and/or substantially bifurcate at least a portion of an interior of the connector 4100. The amount of the connector that is bifurcated or substantially bifurcated can be defined according to various heights as described herein. For example, in some embodiments the diverter can bifurcate and/or substantially bifurcate at least about one half of the height $h_{404}$ of the connector. In some embodiments the diverter 4042 can bifurcate and/or substantially bifurcate at least about two thirds of the height $h_{404}$ of the connector. In some embodiments the diverter 4042 can bifurcate and/or substantially bifurcate at least about three quarters of the height $h_{404}$ of the connector. In some embodiments the diverter 4042 can bifurcate and/or substantially bifurcate at least about seven eighths of the height $h_{404}$ of the connector.

Similarly, in some embodiments the diverter 4042 can bifurcate and/or substantially bifurcate at least about one half of the height $h_{407}$. In some embodiments, the diverter 4042 can bifurcate and/or substantially bifurcate at least about 60 percent of the height $h_{407}$. In some embodiments, the diverter 4042 can bifurcate and/or substantially bifurcate at least about 70 percent of the height $h_{407}$. In some embodiments, the diverter 4042 can bifurcate and/or substantially bifurcate at least about 80 percent of the height $h_{407}$. In some embodiments, the diverter 4042 can bifurcate and/or substantially bifurcate at least about 90 percent of the height $h_{407}$. In some embodiments, the diverter 4042 can bifurcate and/or substantially bifurcate at least about 95 percent of the height $h_{407}$. In some embodiments the entire height of the shoulder or collar 4132 can be bifurcated or substantially bifurcated, and in some embodiments bifurcation can extend distal to the shoulder or collar. In some embodiments, the diverter can bifurcate and/or substantially bifurcate the entire projection member 4170.

Figure 36:
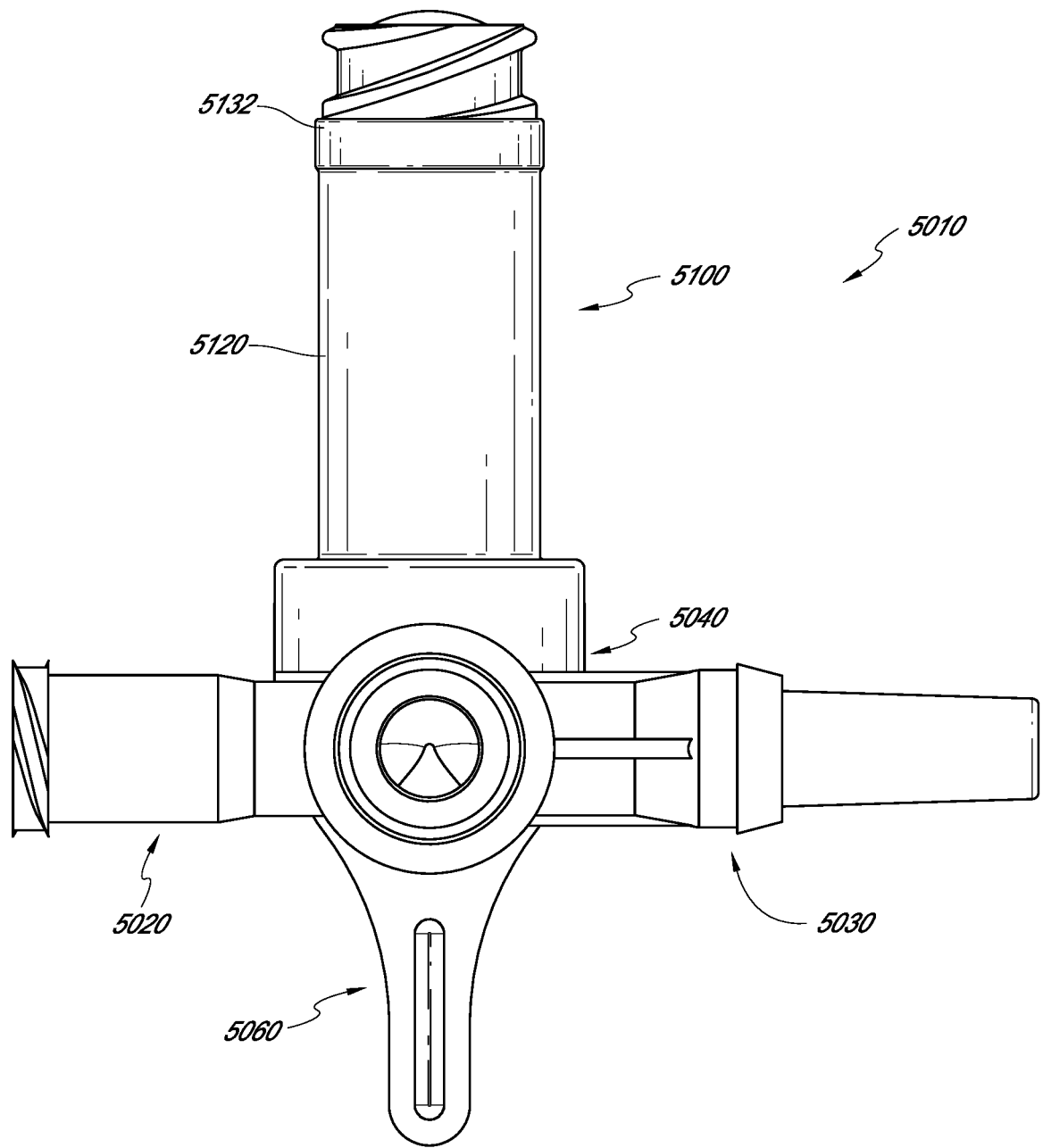
FIG. 36 is a front view of one embodiment of a medical connector positioned on a stopcock.

FIG. 36 is a side view of a stopcock assembly 5010 with a needleless connector 5100 that can have some features or characteristics similar in some regards to the InVision-Plus™ connector available from RyMed Technologies, Inc., of Franklin, Tenn. Some features and characteristics of the connector 5100 are described in U.S. Pat. No. 6,994,315, the entirety of which is hereby incorporated by reference herein for all that it discloses. The stopcock can function according to the various embodiments described herein, and elements similar to elements described in such embodiments are understood to be able to function as thus described, whether called out or not.

Figure 37A:
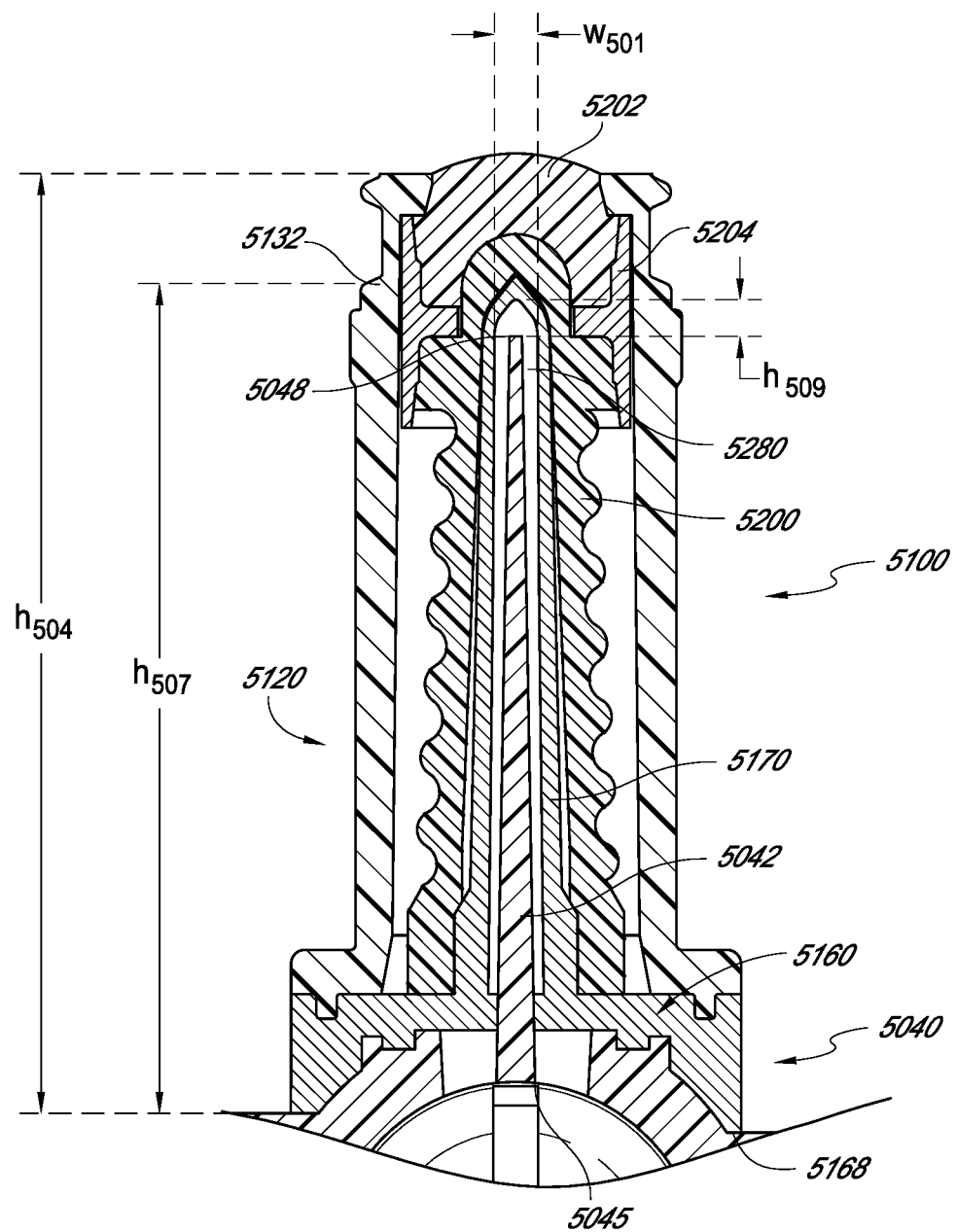
FIG. 37A is a cross section of the medical connector positioned on a stopcock of FIG. 36.
Figure 37B:
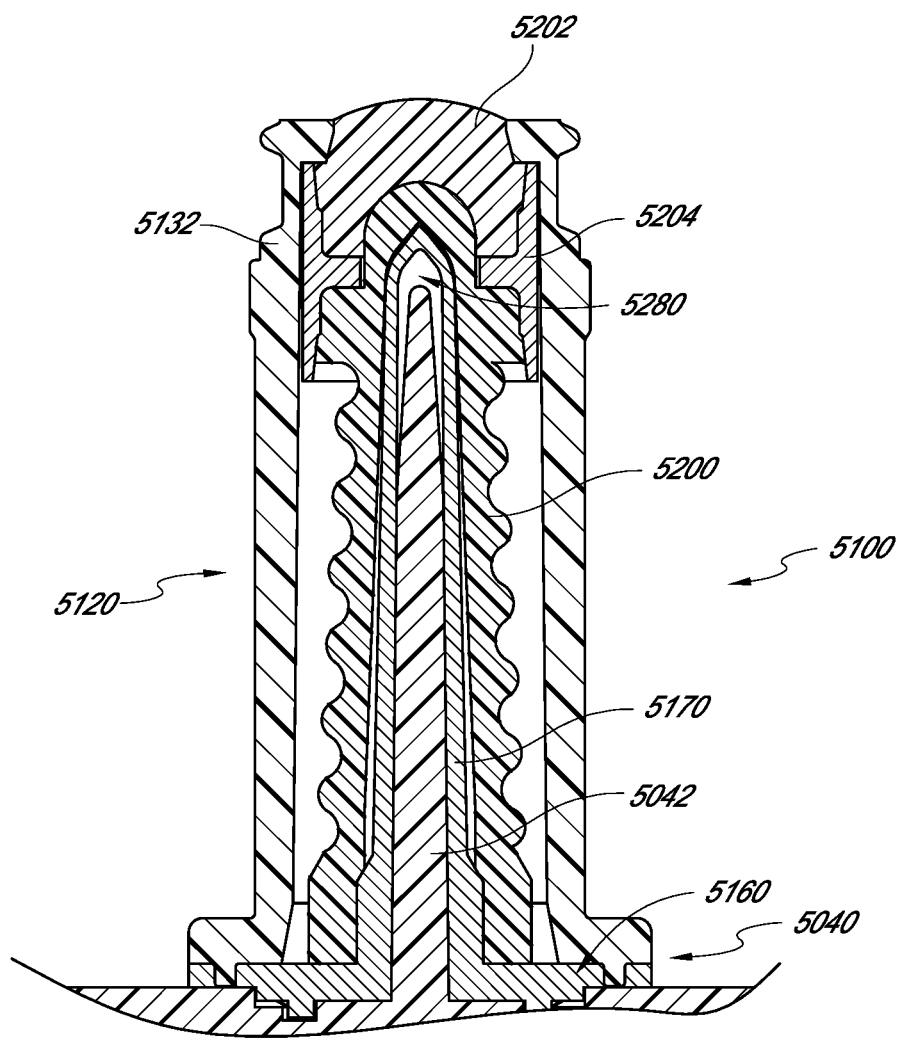
FIG. 37B is a cross section of the medical connector positioned on a stopcock of FIG. 36, rotated approximately 90 degrees from the cross section of FIG. 37A.

FIG. 37A is a sectional view of the connector 5100 shown in FIG. 36, and FIG. 37B is a sectional view rotated approximately 90 degrees from the view of FIG. 37A. In some embodiments, the connector 5100 can include a body member 5120, a base member 5160 with an internal projection member 5170, a valve member 5200 around the internal projection, a guide member 5204, and a septum member 5202. As described above, the needleless connector 5100 can be positioned on a port 5040 of a stopcock with a fluid diverter 5042 that extends into the connector. In some embodiments, a distal most surface defining an interior 5280 of the projection member 5170 can be below the shoulder 5132.

The fluid diverter 5042 can be positioned according to any of the various embodiments described herein. Thus, it can be positioned as described above with respect to a connector height $h_{504}$, measured from a most proximal surface 5168 of the connector to a top or distal most surface of the connector body 5120. For example, in some embodiments the fluid diverter 5042 can direct fluid and/or the fluid diverter extends a substantial distance into the connector 5100. In some embodiments, a substantial distance can be any distance identified below. In some embodiments, the fluid diverter 5042 directs fluid and/or the fluid diverter 5042 extends into the distal about two thirds of the height $h_{504}$ of the connector 5100. In some embodiments, the fluid diverter directs fluid and/or the fluid diverter 5042 extends into the distal about one half of the height $h_{504}$ of the connector. In some embodiments, the fluid diverter directs fluid and/or the fluid diverter 5042 extends into the distal about one third of the height $h_{504}$ of the connector. In some embodiments, the fluid diverter directs fluid and/or the fluid diverter 5042 extends into the distal about one quarter of the height $h_{504}$ of the connector. In some embodiments, the fluid diverter directs fluid and/or the fluid diverter 5042 extends into the distal about three sixteenths of the height $h_{504}$ of the connector. In some embodiments, the fluid diverter directs fluid and/or the fluid diverter 5042 extends into the distal about one eighth of the height $h_{504}$ of the connector. In some embodiments, the fluid diverter directs fluid and/or the fluid diverter 5042 extends into the distal about one sixteenth of the height $h_{504}$ of the connector.

The fluid diverter can also be positioned as described above with respect to a shoulder height $h_{507}$, measured from a most proximal surface 5168 of the connector to a shoulder 5132. Thus, for example, in some embodiments, the fluid diverter 5042 can direct fluid into and/or extend into the distal about two thirds of the shoulder height $h_{507}$. In some embodiments, the fluid diverter can direct fluid into and/or extend into the distal about one half of the shoulder height $h_{507}$. In some embodiments, the fluid diverter can direct fluid into and/or extend into the distal about one third of the shoulder height $h_{507}$. In some embodiments, the fluid diverter can direct fluid into and/or extend into the distal about one quarter of the shoulder height $h_{507}$. In some embodiments, the fluid diverter can direct fluid into and/or extend into the distal about three sixteenths of the shoulder height $h_{507}$. In some embodiments, the fluid diverter can direct fluid into and/or extend into the distal about one eighth of the shoulder height $h_{507}$. In some embodiments, the fluid diverter can direct fluid into and/or extend into the distal about one sixteenth of the shoulder height $h_{507}$. In some embodiments, the fluid diverter 5042 can extend to approximately the shoulder 5132 or beyond the shoulder.

In some embodiments, the fluid diverter 5042 can extend far enough into the internal projection 5170 such that the height $h_{509}$ from a distal tip of the diverter to a distal most surface defining an interior 5280 of the projection member is less than a width $w_{501}$ of the interior 5280 at the distal tip 5048 of the fluid diverter. In some embodiments, the interior can have a generally circular cross-section and the width $w_{501}$ can be approximately equal to a diameter of the cross-section. In some embodiments, the interior can have varying cross-sections and the width can be defined as the width in the illustrated plane. In some embodiments, the height $h_{509}$ can be less than 100 percent of the width $w_{501}$. In some embodiments, the height $h_{509}$ can be less than about 90 percent of the width $w_{501}$. In some embodiments, the height $h_{509}$ can be less than about 80 percent of the width $w_{501}$. In some embodiments, the height $h_{509}$ can be less than about 70 percent of the width $w_{501}$. In some embodiments, the height $h_{509}$ can be less than about 60 percent of the width $w_{501}$. In some embodiments, the height $h_{509}$ can be less than about 50 percent of the width $w_{501}$.

The fluid diverter 5042 can also be sized according to any of the various embodiments described herein. Thus, for example, the diverter can be sized to create a desired available volume within the projection member 5170, as described above. Thus, for example, the diverter can be sized to displace a desired volume by adjusting the width of the diverter in the plane of FIG. 37A, adjusting the width of the diverter in the plane of FIG. 37B, and/or adjusting the height of the diverter. In some embodiments, the volume of available space within the projection member 5170 can be greater than or equal to approximately 0.005 mL and/or less than or equal to approximately 0.03 mL. In some embodiments, the available volume can be greater than or equal to approximately 0.01 mL and/or less than or equal to approximately 0.02 mL. In some embodiments, the available volume can be greater than or equal to approximately 0.013 mL and/or less than or equal to approximately 0.017 mL. In some embodiments, the available volume can be approximately 0.015 mL.

As a further example, the diverter 5042 can be configured to bifurcate and/or substantially bifurcate at least a portion of an interior of the connector 5100. The amount of the connector that is bifurcated or substantially bifurcated can be defined according to various heights as described herein. For example, in some embodiments the diverter can bifurcate and/or substantially bifurcate at least about one half of the height $h_{504}$ of the connector. In some embodiments the diverter 5042 can bifurcate and/or substantially bifurcate at least about two thirds of the height $h_{504}$ of the connector. In some embodiments the diverter 5042 can bifurcate and/or substantially bifurcate at least about three quarters of the height $h_{504}$ of the connector. In some embodiments the diverter 5042 can bifurcate and/or substantially bifurcate at least about seven eighths of the height $h_{504}$ of the connector.

Similarly, in some embodiments the diverter 5042 can bifurcate and/or substantially bifurcate at least about one half of the height $h_{507}$. In some embodiments, the diverter 5042 can bifurcate and/or substantially bifurcate at least about 60 percent of the height $h_{507}$. In some embodiments, the diverter 5042 can bifurcate and/or substantially bifurcate at least about 70 percent of the height $h_{507}$. In some embodiments, the diverter 5042 can bifurcate and/or substantially bifurcate at least about 80 percent of the height $h_{507}$. In some embodiments, the diverter 5042 can bifurcate and/or substantially bifurcate at least about 90 percent of the height $h_{507}$. In some embodiments, the diverter 5042 can bifurcate and/or substantially bifurcate at least about 95 percent of the height $h_{507}$.

Although some specific examples have been provided herein, it should be understood that a stopcock with a fluid diverter can be incorporated into many other connectors than those specifically disclosed herein. Additionally, it is understood that the various examples of diverter size and positioning described with respect to various connectors can be applied to any of the connectors specifically disclosed herein and connectors other than those specifically disclosed herein.

The terms "approximately", "about", and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above.

Similarly, this method of disclosure is not to be interpreted as reflecting an intention that any claim require more features than are expressly recited in that claim. Rather, inventive aspects may lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A multi-port branched medical connector adapted for flushing a needleless connector on one port of the branched connector, the branched connector comprising:

a body comprising a first port, a second port, and a third port, wherein the third port is positioned between the first and second ports;

a fluid diverter extending away from the third port; and the needleless connector at the third port and at least partially surrounding the fluid diverter, the needleless connector comprising:

a connector housing having a first end and a second end, the first end distal the second end;

a compressible seal positioned at least partially within the connector housing and configured to impede flow through the first end of the connector housing when in a first position;

an internal projection member positioned at least partially within the compressible seal, the internal projection member having walls that define an internal cavity that encompasses the fluid diverter, an opening at a proximal end of the internal projection member, and at least one distal opening to an internal cavity of the compressible seal at a distal end of the internal projection member, the at least one distal opening having a proximal surface and a distal surface and being in fluid communication with the compressible seal;

wherein the fluid diverter extends at least partially into the compressible seal, and wherein the fluid diverter has a profile, the profile of the fluid diverter adapted to track the walls of the internal cavity of the internal projection member in a distal direction a distance past the proximal surface of the at least one distal opening to effect flushing of the internal projection member at the distal end of the internal projection member.

2. The multi-port branched medical connector of claim 1, wherein the fluid diverter bifurcates the internal cavity of the internal projection member at the proximal end of the internal projection member.

3. The multi-port branched medical connector of claim 1, wherein the fluid diverter substantially bifurcates at least about half of the internal cavity of the internal projection member.

4. The multi-port branched medical connector of claim 3, wherein the fluid diverter substantially bifurcates at least about three quarters of the internal cavity of the internal projection member.

5. The multi-port branched medical connector of claim 1, wherein the fluid diverter has a distal tip that extends within the internal projection member to at least the proximal surface of the at least one distal opening.

6. The multi-port branched medical connector of claim 1, wherein the compressible seal has a plurality of sealing rings on an interior surface thereof, the plurality of sealing rings configured to contact and seal against the internal projection member.

7. The multi-port branched medical connector of claim 6, wherein at least one sealing ring of the plurality of sealing rings contacts the internal projection member above the at least one distal opening and at least one sealing ring of the plurality of sealing rings contacts the internal projection member below the at least one distal opening.

8. The multi-port branched medical connector of claim 6, wherein a height of the internal projection member from the distal surface of the at least one distal opening to an upper tip of the internal projection member is greater than or equal to a height of the internal cavity of the compressible seal from an uppermost sealing ring to an uppermost surface of the internal cavity.

9. The multi-port branched medical connector of claim 1, wherein the fluid diverter and the internal projection member are integrally formed.

10. The multi-port branched medical connector of claim 5, wherein the distal tip of the fluid diverter extends within the internal projection member to a position past the proximal surface of the at least one distal opening.

11. The multi-port branched medical connector of claim 1, wherein the fluid diverter has a distal tip, the profile of the fluid diverter being widest at a proximal end of the fluid diverter and narrower towards the distal tip.

* * * * *